US007919108B2

(12) United States Patent
Reyes et al.

(10) Patent No.: US 7,919,108 B2
(45) Date of Patent: Apr. 5, 2011

(54) TAXANE COATINGS FOR IMPLANTABLE MEDICAL DEVICES

(75) Inventors: Priscilla Reyes, Duncan, OK (US); William F. Moore, Bloomington, IN (US); Patrick H. Ruane, Haywood, CA (US); Darin G. Schaeffer, Bloomington, IN (US); Melinda S. Morrell, Vienna, VA (US)

(73) Assignees: Cook Incorporated, Bloomington, IN (US); MED Institute Inc., West Lafayette, IN (US)

( * ) Notice: Subject to any disclaimer, the term of this patent is extended or adjusted under 35 U.S.C. 154(b) by 723 days.

(21) Appl. No.: 11/715,975

(22) Filed: Mar. 8, 2007

(65) Prior Publication Data
US 2007/0212394 A1 Sep. 13, 2007

Related U.S. Application Data

(60) Provisional application No. 60/781,264, filed on Mar. 10, 2006, provisional application No. 60/830,726, filed on Jul. 13, 2006, provisional application No. 60/830,660, filed on Jul. 13, 2006.

(51) Int. Cl.
*A61F 2/00* (2006.01)
*A61F 2/06* (2006.01)
*A01N 43/02* (2006.01)

(52) U.S. Cl. .................. 424/423; 514/449; 623/1.3
(58) Field of Classification Search .................. None
See application file for complete search history.

(56) References Cited

U.S. PATENT DOCUMENTS

| 4,739,762 | A | 4/1988 | Palmaz | 128/343 |
|---|---|---|---|---|
| 5,133,732 | A | 7/1992 | Wiktor | 606/195 |
| 5,292,331 | A | 3/1994 | Boneau | 606/198 |
| 5,380,299 | A | 1/1995 | Fearnot et al. | 604/265 |
| 5,421,955 | A | 6/1995 | Lau et al. | 216/48 |
| 5,440,056 | A | 8/1995 | Klein et al. | 549/510 |
| 5,609,629 | A | 3/1997 | Fearnot et al. | 623/1 |
| 5,824,049 | A | 10/1998 | Ragheb et al. | 623/1 |
| 5,873,904 | A | 2/1999 | Ragheb et al. | 623/1 |
| 6,090,127 | A | 7/2000 | Globerman | 606/194 |
| 6,096,070 | A | 8/2000 | Ragheb et al. | 623/1 |
| 6,221,153 | B1 | 4/2001 | Castor et al. | 117/11 |
| 6,299,604 | B1 | 10/2001 | Ragheb et al. | 604/265 |
| 6,306,166 | B1 | 10/2001 | Barry et al. | 623/1.46 |
| 6,530,951 | B1 | 3/2003 | Bates et al. | 623/1.45 |
| 6,589,546 | B2 | 7/2003 | Kamath et al. | 424/423 |
| 6,599,275 | B1 | 7/2003 | Fischer, Jr. | 604/265 |
| 6,689,802 | B2 | 2/2004 | DiMarco et al. | 514/365 |
| 6,730,064 | B2 | 5/2004 | Ragheb et al. | 604/265 |
| 6,774,278 | B1 | 8/2004 | Ragheb et al. | 623/11 |
| 6,858,644 | B2 | 2/2005 | Benigni et al. | 514/449 |
| 6,878,832 | B2 | 4/2005 | Saiji | 549/510 |
| 6,918,927 | B2 | 7/2005 | Bates et al. | 623/1.15 |
| 6,977,085 | B2 | 12/2005 | Werling et al. | 424/489 |
| 6,982,276 | B2 | 1/2006 | DiMarco et al. | 514/365 |
| 7,060,285 | B2 | 6/2006 | Muller | 424/400 |
| RE39,251 | E | 8/2006 | Guo | 514/365 |
| 7,153,879 | B2 | 12/2006 | DiMarco et al. | 514/365 |
| 2002/0142050 | A1 | 10/2002 | Straub et al. | 424/499 |
| 2003/0028243 | A1 | 2/2003 | Bates et al. | 623/1.15 |
| 2003/0028244 | A1 | 2/2003 | Bates et al. | 623/1.15 |
| 2003/0036794 | A1 | 2/2003 | Ragheb et al. | 623/1.15 |
| 2003/0144344 | A1 | 7/2003 | Benigni et al. | 514/449 |
| 2003/0236513 | A1 | 12/2003 | Schwarz et al. | 604/890.1 |
| 2004/0039441 | A1 | 2/2004 | Rowland et al. | 623/1.42 |
| 2004/0047909 | A1 | 3/2004 | Ragheb et al. | 424/471 |
| 2004/0063977 | A1 | 4/2004 | Saiji | 549/510 |
| 2004/0068241 | A1 | 4/2004 | Fischer, Jr. | 604/265 |
| 2004/0073284 | A1 * | 4/2004 | Bates et al. | 623/1.11 |
| 2004/0243225 | A1 | 12/2004 | Ragheb et al. | 623/1.42 |
| 2006/0079526 | A1 | 4/2006 | Wrasidlo et al. | 514/242 |
| 2006/0116420 | A1 | 6/2006 | Chidambaram et al. | 514/449 |

FOREIGN PATENT DOCUMENTS

| EP | 0 717 041 A1 | 6/1996 |
|---|---|---|
| EP | 0717041 A1 * | 6/1996 |
| EP | 0734 721 A2 | 10/1996 |
| JP | 7-289630 | 11/1995 |
| WO | WO 93/10076 A1 | 5/1993 |
| WO | WO 00/32238 A1 | 6/2000 |
| WO | WO 03/006180 A1 | 1/2003 |

OTHER PUBLICATIONS

Lee, et al., Bull. Dorean Chem. Soc., vol. 22, No. 8, 2001.*
Gi, Korean J. Chem. Eng., 21 (4), 2004.*
Lee, Bull. Korean Chem. Soc., 2001.*
Chen, Int. J. Pharm., 2005.*
Kamath, K. R. et al. "The Taxus drug-eluting stent: A new paradigm in controlled delivery", Adv. Drug Delivery Reviews, vol. 58, No. 3, pp. 412-436 (2006).
International Search Report for PCT/US2007/006223.
Jeong Hoon Lee, Un-Sook Gi, Jin-Hyun Kim, Yongae Kim, Hunseung Oh and Bumchan Min, "Preparation and Characterization of Solvent Induced Dihydrated, Anhydrous, and Amorphous Paclitaxel," *Bull. Korean Chem. Soc.*, 2001, vol. 22, No. 8, 925-928.
Richard T. Liggins, W.L. Hunter, and Helen M. Burt, "Solid-State Characterization of Paclitaxel," *Journal of Pharmaceutical Sciences*, vol. 86, No. 12, Dec. 1997, 1458-1463.
Anil K. Singla, Alka Garg, Deepika Aggarwal, "Paclitaxel and its formulations," *International Journal of Pharmaceutics*, 235 (2002) 179-192.

* cited by examiner

*Primary Examiner* — Robert A Wax
*Assistant Examiner* — William Craigo
(74) *Attorney, Agent, or Firm* — Brinks Hofer Gilson & Lione

(57) ABSTRACT

This disclosure relates to implantable medical devices coated with a taxane therapeutic agent, such as paclitaxel, in one or more solid form(s) having varying dissolution rates. Particularly preferred coatings comprise amorphous and/or solvated solid forms of taxane therapeutic agents that provide durable coatings that release the taxane over a desired period of time, which can be varied in the absence of a polymer by selecting the type and amount of solid forms of the taxane therapeutic agent in the coating. Other preferred embodiments relate to methods of coating medical devices and methods of treatment. The coatings can provide a sustained release of the taxane therapeutic agent within a body vessel without containing a polymer to achieve the desired rate of paclitaxel elution.

19 Claims, 23 Drawing Sheets

TAXANE COATINGS FOR IMPLANTABLE MEDICAL DEVICES

RELATED APPLICATIONS

This application claims the benefit of following U.S. Provisional Patent Applications, all of which are incorporated herein by reference in their entirety: 60/781,264, entitled "Taxane Coatings for Implantable Medical Devices" and filed Mar. 10, 2006; 60/830,726, entitled "Controlled Release Taxane Coatings for Implantable Medical devices" and filed Jul. 13, 2006; and 60/830,660, entitled "Cyclodextrin Elution Media for Medical Device Coatings Comprising a Taxane Therapeutic Agent" and filed Jul. 13, 2006.

TECHNICAL FIELD

The present disclosure relates to releasable taxane therapeutic agent coatings for implantable medical devices, including stents.

BACKGROUND

Delivery of a therapeutic agent from an implantable medical device can be desirable for a variety of applications. Therapeutic agents can be released from a medical device, such as an expandable stent or valve, to treat or mitigate undesirable conditions including restenosis, tumor formation or thrombosis. Procedures for mitigating certain conditions can include implantation of a device comprising a therapeutic agent. For example, the implantation of stents during angioplasty procedures has substantially advanced the treatment of occluded body vessels. Angioplasty procedures such as Percutaneous Transluminal Coronary Angioplasty (PTCA) can widen a narrowing or occlusion of a blood vessel by dilation with a balloon. Occasionally, angioplasty may be followed by an abrupt closure of the vessel or by a more gradual closure of the vessel, commonly known as restenosis. Acute closure may result from an elastic rebound of the vessel wall and/or by the deposition of blood platelets and fibrin along a damaged length of the newly opened blood vessel. In addition, restenosis may result from the natural healing reaction to the injury to the vessel wall (known as intimal hyperplasia), which can involve the migration and proliferation of medial smooth muscle cells that continues until the vessel is again occluded. To prevent such vessel occlusion, stents have been implanted within a body vessel. However, restenosis may still occur over the length of the stent and/or past the ends of the stent where the inward forces of the stenosis are unopposed. To reduce this problem, one or more therapeutic agents may be administered to the patient. For example, a therapeutic agent may be administered systemically, locally administered through a catheter positioned within the body vessel near the stent, or coated on the stent itself.

A medical device can be coated with a therapeutic agent in a manner suitable to expose tissue near the implantation site of the medical device to the therapeutic agent over a desired time interval, such as by releasing the therapeutic agent from an implanted stent into surrounding tissue inside a body vessel. Various approaches can be used to control the rate and dose of release of therapeutic agents from an implantable medical device. The design configuration of an implantable device can be adapted to influence the release of therapeutic from the device. A therapeutic agent can be included in the implantable medical device in various configurations. In some devices, the therapeutic agent is contained within an implantable frame or within a coating on the surface of the implantable frame. An implantable frame coating can include a bioabsorbable material mixed with a therapeutic agent, or coated over the therapeutic agent. Some implantable medical devices comprise an implantable frame with a porous biostable material mixed with or coated over a therapeutic agent. Implantable medical devices can also comprise a biostable material containing a dissolvable material and a therapeutic agent, where dissolution of the removable material upon implantation forms pores that release the therapeutic agent.

The design of a controlled release medical device can also depend on the desired mode of implantation of the device. The device can be adapted to the appropriate biological environment in which it is used. For example, a coated medical device for percutaneous transcatheter implantation can be sized and configured for implantation from the distal portion of a catheter, and adapted for expansion at the point of treatment within the body vessel by balloon or self-expansion. An implantable medical device can also be adapted to withstand a desired amount of flexion or impact, and should provide delivery of a therapeutic agent with a desired elution rate for a desired period of time.

Paclitaxel, and taxane analogues and derivatives thereof, can be used as a therapeutic agent coated on and released from implantable devices, such as stents, to mitigate or prevent restenosis. Paclitaxel is believed to disrupt mitosis (M-phase) by binding to tubulin to form abnormal mitotic spindles (i.e., a microtubule stabilizing agent). A therapeutic compound such as paclitaxel can crystallize as more than one distinct crystalline species (i.e., having a different arrangement of molecules in a solid form) or shift from one crystalline species to another. This phenomena is known as polymorphism, and the distinct species are known as polymorphs. Polymorphs can exhibit different optical properties, melting points, solubilities, chemical reactivities, dissolution rates, and different bioavailabilities. Paclitaxel and taxane derivatives thereof can be formed in an amorphous form, or in at least two different crystalline polymorphs. Solid forms of paclitaxel at room temperature include: amorphous paclitaxel ("aPTX"), dihydrate crystalline paclitaxel ("d PTX") and anhydrous crystalline paclitaxel. These different solid forms of paclitaxel can be characterized and identified using various solid-state analytical tools, for example as described by Jeong Hoon Lee et al., "Preparation and Characterization of Solvent Induced Dihydrate, Anhydrous and Amorphous Paclitaxel," *Bull. Korean Chem. Soc.* v. 22, no. 8, pp. 925-928 (2001), incorporated herein by reference in its entirety.

U.S. Pat. No. 6,858,644, filed Nov. 26, 2002 by Benigni et al. ("Benigni"), teaches a crystalline solvate comprising paclitaxel and a solvent selected from the group consisting of dimethylsulfoxide, N,N'-dimethylformamide, N,N'-dimethylacetamide, N-methyl-2-pyrrolidone, 1,3-dimethyl-2-imidazolidinone, 1,3-dimethyl-3,4,5,6-tetrahydro-2-(1H)-pyrimidinone, and acetonitrile and combinations thereof. However, Benigni does not describe implantable device coatings comprising crystalline paclitaxel forms with different elution rates. Benigni discloses various solid forms of paclitaxel, including a first solid form reported as a highly water insoluble crystalline, granular, solvent-free form. The first solid form is substantially non-hygroscopic under normal laboratory conditions (relative humidity (RH) approximately 50-60%; 20-30° C.). However, when contacted with an atmosphere having a relative humidity greater than about 90%, or in aqueous suspensions, dispersions or emulsions, the first paclitaxel solid form reportedly converts (as a function of time, temperature, agitation, etc.) to a thermodynamically more stable second solid form. The second solid form is described as a trihydrate orthorhombic form having six water sites per two independent paclitaxel molecules (one paclitaxel "dimer"). These hydrated crystals reportedly present a fine, hair-like appearance and are even less water soluble than the first solid form. The second solid form is reportedly formed in aqueous suspensions or through crystallization from aqueous solvents in the presence of a large excess of water. This form is also disclosed in patent application EP 0 717 041, which describes the second solid form as being characterized by single crystal X-ray diffraction studies as being orthorhombic, with unit cells containing two crystallographically independent molecules of paclitaxel associated with hydrogen bonds to form a "dimer". Mastropaolo, et al. disclosed a crystalline solvate of paclitaxel obtained by evaporation of solvent from a solution of Taxol® in dioxane, water and xylene. Proc. Natl. Acad. Sci. USA 92, 6920-24 (July, 1995). This solvate is indicated as being unstable, and, in any event, has not been shown to effect purification of crude paclitaxel. The thin plate-like crystals are reported to contain five water molecules and three dioxane molecules per two molecules of paclitaxel.

Many medical device coatings adapted for controlled release of taxane therapeutic agent such as paclitaxel rely on a polymer coating that is mixed with or applied above and/or beneath the releasable therapeutic agent to regulate the release of the therapeutic agent from the medical device surface. For example, U.S. Pat. No. 6,589,546 to Kamath et al. (filed Dec. 10, 2001) and Published US Patent Application 2004/0039441 by Rowland et al. (filed May 20, 2003) describe medical device coatings comprising a therapeutic agent mixed with a polymer to provide a controlled release of the therapeutic agent. Published US Patent Application 2003/0236513 by Schwarz et al. (filed Jun. 19, 2002) describes medical device coatings comprising a polymer coating deposited over or mixed with a therapeutic agent to control the rate of release of the therapeutic agent from the device.

What is needed are medical devices that permit controlled release of a therapeutic agent as a result of the solid form of the therapeutic agent, with or without a polymer. In particular, there remains a need for intravascularly-implantable medical devices capable of releasing a therapeutic agent at a desired rate and over a desired time period upon implantation. Preferably, an implanted medical device releases a therapeutic agent at the site of medical intervention to promote a therapeutically desirable outcome, such as mitigation of restenosis. There is also a need for a medical device with a coating of a releasable therapeutic agent coating having sufficient durability to resist the undesirable premature release of the therapeutic agent from the device prior to implantation at a point of treatment within a body vessel. In addition, there is a need for sufficiently durable medical device coatings comprising or consisting of a sustained-release taxane therapeutic agent while being free from a polymer or non-biocompatible organic solvents.

SUMMARY

Medical devices comprising a releasable taxane therapeutic agent coating are provided. The taxane therapeutic agent coating includes one or more taxane therapeutic agents deposited on the device in one or more solid forms, including various polymorphs or solvated forms of the taxane therapeutic agent. For example, the taxane therapeutic agent coating can be deposited as a solvated, crystalline or amorphous solid form, or a combination thereof. These different solid forms of the taxane therapeutic agent are preferably formed from molecules with identical molecular structures arranged differently in the solid coating on the medical device. Some solid forms may further comprise water molecules. Once dissolved, taxane therapeutic agent molecules originating from different solid forms are indistinguishable after elution into solution or within the body. However, the taxane solid forms often have measurably different rates of elution from the medical device. Therefore, medical device coatings described herein can provide for desired release rates of a taxane therapeutic agent depending on the number and distribution of solid form(s) of the therapeutic agent in the coating. The coating can have one or more layers. The taxane therapeutic agent coatings can provide controlled release of the taxane therapeutic agent from the medical device from coatings in the absence of a polymer in the coating.

In a first embodiment, solid compositions comprising a taxane therapeutic agent in one, two or more solid forms are provided. The compositions preferably include a single taxane therapeutic agent in two or more solid forms, although a taxane therapeutic agent coating can optionally include multiple taxane therapeutic agents. Taxane therapeutic agent molecules preferably share a common core taxane structure, but can differ in the arrangement of the taxane molecules in the various solid forms. The various solid forms of the taxane therapeutic agent can be characterized and differentiated by one or more physical properties, including infrared and Raman vibrational spectroscopy, differing solubilities in various elution media, different melting points, X-ray Diffraction (XRD), $^{13}C$ Nuclear Magnetic Resonance (NMR), and/or Temperature Programmed Desorption (TPD). The presence of different solid forms of the taxane therapeutic agent in a medical device coating are preferably identified by contacting the coating with an elution medium that selectively dissolves one solid form more rapidly than a second solid form. In solution with an elution medium, such as porcine serum or blood, the presence of the taxane therapeutic agent can be identified, for example by using ultraviolet (UV) spectroscopy or high pressure liquid chromatography (HPLC). For example, in certain elution media such as porcine serum, the dihydrate taxane therapeutic agent structure dissolves more slowly than the amorphous solid form. Preferably, the taxane therapeutic agent is paclitaxel, although the taxane therapeutic agent may include one or more paclitaxel analog or derivative. The medical device coating can include any suitable amount(s) of one or more of the taxane solid forms that provide a desired elution rate of the taxane therapeutic agent, while also preferably having a desired durability and suitable level of surface uniformity.

In a first aspect, the first embodiment provides a medical device coating composition including a taxane therapeutic agent in a solvate crystal solid form. Preferably, the solvate structure is a dihydrate taxane structure. In a second aspect, the medical device coating composition includes an amorphous taxane solid form. In a third aspect, the medical device coating composition includes an anhydrous taxane solid form. In a fourth aspect, the medical device coating composition includes a two or more solid forms of a taxane therapeutic agent, with the different solid forms provided in the same layer of a coating or in separate coating layers. A single-layer coating can comprise a mixture of a taxane therapeutic agent in the dihydrate taxane crystalline solid form and the taxane therapeutic agent configured in the amorphous taxane solid form. Preferably, the coating is free of a polymer, or contains less than about 0.10 µg of any polymer per $mm^2$ of abluminal surface area and preferably less than a total of 1 µg of any polymer in the entire coating. Accordingly, taxane therapeutic agent coatings with desirable elution rates can be obtained without including a polymer coating component in contact with the therapeutic agent.

In a second embodiment, an implantable medical device is provided with a coating that includes one or more layers each comprising or consisting essentially of a taxane therapeutic agent in one or more solid forms. The solid forms of the taxane therapeutic agent coating can include amorphous, anhydrous or a solvated taxane therapeutic agent. Preferably, the solid form of the taxane therapeutic agent includes an amorphous taxane structure, an anhydrous taxane structure, a dihydrate solvate taxane structure, or a combination of two or more of these solid forms. In a first aspect, the second embodiment provides medical device coatings having a one or more layers comprising or consisting of a taxane therapeutic agent in a single solid form. The solid form is preferably an amorphous or anhydrous polymorph or dihydrate solvated form of the taxane therapeutic agent. In a second aspect, the second embodiment provides medical device coatings having a one or more layers comprising or consisting of a mixture of a taxane therapeutic agent in two or more solid forms. In a third aspect, the second embodiment provides medical device coatings having at least two layers, wherein the second coating consists essentially of a taxane therapeutic agent in a first solid form, and the second coating comprises or consists essentially of the taxane therapeutic agent in a second solid form. Optionally, the first layer and/or the second layer can include a mixture of two or more solid forms of the taxane therapeutic agent.

In a third embodiment, methods of coating taxane therapeutic agents on a medical device are provided. In one aspect, methods of depositing a coating comprising a solvate solid form of a taxane therapeutic agent, such as a dihydrate solid form, are provided. For example, methods for depositing a paclitaxel dihydrate or single-layer mixtures of paclitaxel dihydrate and amorphous paclitaxel are particularly preferred. The taxane therapeutic agent is preferably deposited on a medical device by spraying a solution of the therapeutic agent using a pressure, ultrasonic or electrostatic spray apparatus. Different solid forms of the taxane therapeutic agent can be deposited in one or more layers on the medical device by changing the solvent system or the spray coating parameters used in the spray deposition process.

DETAILED DESCRIPTION

Figure 1A:
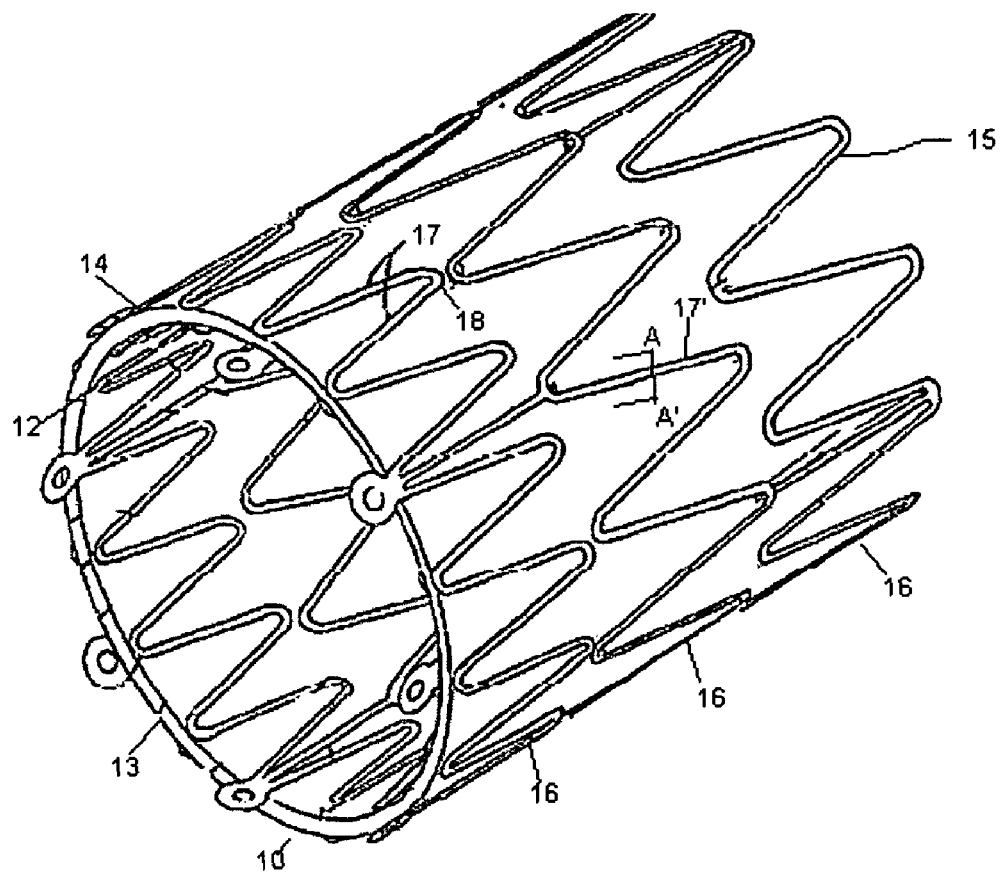
FIG. 1A shows a coated implantable medical device.

The present invention relates to medical device coatings that include a taxane therapeutic agent. Preferred compositions comprise one or more taxanes in one or more solid forms selected to provide desired properties of dissolution rate and/or durability. The coatings are preferably substantially free of a polymer, and may consist only of taxane therapeutic agent(s) in one or more solid forms. One particularly preferred taxane therapeutic agent is paclitaxel. Unless otherwise specified, description of paclitaxel coatings herein relate to a preferred embodiment of the taxane therapeutic agent, and is intended to be illustrative of all taxane therapeutic agents capable of forming the solvate and polymorph solid forms described, without limiting the scope of the therapeutic agent to paclitaxel.

Certain preferred embodiments provide an implantable medical device ("medical device") allowing for the release of a taxane therapeutic agent into the adjacent or surrounding tissue upon implantation. The taxane therapeutic agent is preferably paclitaxel, or a derivative/analog thereof, releasably coated on at least a portion of the abluminal surface of the medical device. Preferably, the coating consists essentially of the taxane therapeutic agent, and does not include a material, such as a polymer or non-polymer carrier, to modify the rate of release of the therapeutic agent. In particular, the coating is preferably free of a polymer, or contains less than about 0.50 μg, 0.10 μg or 0.05 μg of a polymer per $mm^2$ of abluminal surface area and preferably less than 10 μg, 5 μg, 1 μg or 0.5 μg of a polymer total in the coating. Most preferably, the coating is free of a polymer, or contains less than about 0.50 μg, 0.10 μg or 0.05 μg of any polymer per $mm^2$ of abluminal surface area and preferably less than 10 µg, 5 µg, 1 µg or 0.5 µg of any polymer total in the coating.

The rate of release of the paclitaxel therapeutic agent from the medical device can be altered by providing a coating including varying amounts of the one or more paclitaxel polymorph compositions releasably attached to the medical device. For example, the rate of release of paclitaxel can be extended by providing paclitaxel coatings with the dihydrate solid form of paclitaxel, alone or in combination with other paclitaxel solid forms. Optionally, one or more solid forms of paclitaxel can be included in separate coating layers on the surface of, or within holes or wells formed in, medical device. Desirably, the medical device comprises materials configured to provide for release of a paclitaxel therapeutic agent within a body vessel according to a therapeutically effective elution profile.

Definitions

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The term "hydrophobic," as used herein, refers to a substance with a solubility in water of less than 0.1 mg/mL at room temperature (about 25° C.).

A therapeutic agent is "enclosed" if the therapeutic agent is surrounded by the coating or other portions of the medical device, and does not form a portion of the surface area of the medical device prior to release of the therapeutic agent. When a medical device is initially placed in an elution medium, an enclosed therapeutic agent is preferably not initially in contact with the elution medium.

The term "elution," as used herein, refers to removal of a material from a substrate by contact with an elution medium. The elution medium can remove the material from the substrate by any process, including by acting as a solvent with respect to the removable material. For example, in medical devices adapted for introduction to the vascular system, blood can act as an elution medium that dissolves a therapeutic agent releasably associated with a portion of the surface of the medical device. The therapeutic agent can be selected to have a desired solubility in a particular elution medium. Unless otherwise indicated, the term "release" referring to the removal of the therapeutic agent from a coating in contact with an elution medium is intended to be synonymous with the term "elution" as defined above. Similarly, an "elution profile" is intended to be synonymous with a "release profile," unless otherwise indicated.

An "elution medium," as used herein, refers to a material (e.g. a fluid) or environment that releases a therapeutic agent from a coating upon contact of the coating with the elution medium for a desired period of time. A suitable elution medium is any substance or environment into which the therapeutic agent can be released. The elution medium is desirably a fluid. More desirably, the elution medium is a biological fluid such as blood or porcine serum, although any other chemical substance can be used as an elution medium. For example, alternative elution media include phosphate buffered saline, blood, a cyclodextrin such as Heptakis-(2,6-di-O-methyl)-β-cyclodextrin (HCD), Sodium Dodecyl Sulfate (SDS), aqueous solutions, reaction conditions including temperature and/or pH, or combinations thereof, that release the therapeutic agent at a desired rate. Preferably, the elution medium is a fluid that provides an elution profile that is similar to the elution profile obtained upon implantation of the medical device within a body vessel and/or a desired time period for elution. For example, porcine serum can provide an elution profile that is similar to the elution profile in blood for some coating configurations.

The term "effective amount" refers to an amount of an active ingredient sufficient to achieve a desired affect without causing an undesirable side effect. In some cases, it may be necessary to achieve a balance between obtaining a desired effect and limiting the severity of an undesired effect. It will be appreciated that the amount of active ingredient used will vary depending upon the type of active ingredient and the intended use of the composition of the present invention.

The terms "about" or "substantially" used with reference to a quantity includes variations in the recited quantity that are equivalent to the quantity recited, such as an amount that is insubstantially different from a recited quantity for an intended purpose or function.

The term "luminal surface," as used herein, refers to the portion of the surface area of a medical device defining at least a portion of an interior lumen. Conversely, the term "abluminal surface," as used herein, refers to portions of the surface area of a medical device that do not define at least a portion of an interior lumen. For example, where the medical device is a tubular frame formed from a plurality of interconnected struts and bends defining a cylindrical lumen, the abluminal surface can include the exterior surface, sides and edges of the struts and bends, while the luminal surface can include the interior surface of the struts and bends.

The term "interface," as used herein, refers to a common boundary between two structural elements, such as two coating layers in contact with each other.

The term "coating," as used herein and unless otherwise indicated, refers generally to material attached to an implantable medical device. A coating can include material covering any portion of a medical device, and can be configured as one or more coating layers. A coating can have a substantially constant or a varied thickness and composition. Coatings can be adhered to any portion of a medical device surface, including the luminal surface, the abluminal surface, or any portions or combinations thereof.

The term "coating layer," as used herein, refers to a stratified portion of a coating having a measurable composition. Coating layers may be identified by one or more measurable properties (such as rate of elution, appearance, durability, infrared spectrum, etc.), and may be differentiated from an adjacent coating layer by at least one measurable property (e.g. different elution rates). Coating layers are substantially parallel to typically oriented a substrate surface. A coating layer material can be positioned in contact with the substrate surface, or in contact with other material(s) between the substrate surface and the coating layer material. A coating layer can cover any portion of the surface of a substrate, including material positioned-in-separate discrete portions of the substrate or a continuous layer over an entire substrate surface.

The term "implantable" refers to an ability of a medical device to be positioned at a location within a body, such as within a body vessel. Furthermore, the terms "implantation" and "implanted" refer to the positioning of a medical device at a location within a body, such as within a body vessel.

The term "alloy" refers to a substance composed of two or more metals or of a metal and a nonmetal intimately united, such as by chemical or physical interaction. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

The term "mixture" refers to a combination of two or more substances in which each substance retains its own chemical identity and properties.

The terms "absorption," "bioresorption" and "bioabsorption" can be used interchangeably to refer to the ability of the polymer or its degradation products to be removed by biological events, such as by fluid transport away from the site of implantation or by cellular activity (e.g., phagocytosis). The term "bioabsorbable" will generally be used in the following description to encompass resorbable, absorbable, bioresorbable, and biodegradable.

A "biocompatible" material is a material that is compatible with living tissue or a living system by not being toxic or injurious.

A "non-bioabsorbable" or "biostable" material refers to a material, such as a polymer or copolymer, which remains in the body without substantial bioabsorption.

The phrase "controlled release" refers to an alteration of the rate of release of a therapeutic agent from a medical device coating in a given environment. A coating or configuration that alters the rate at which the therapeutic agent is released from a medical device provides for the controlled release of the therapeutic agent. A "sustained release" refers to prolonging the rate or duration of release of a therapeutic agent from a medical device. The rate of a controlled release of a therapeutic agent may be constant or vary with time. A controlled release may be described with respect to a drug elution profile, which shows the measured rate at which the therapeutic agent is removed from a drug-coated device in a given elution medium (e.g., solvent) as a function of time. A controlled release elution profile may include, for example, an initial burst release associated with the introduction of the medical device into the physiological environment, followed by a more gradual subsequent release. A controlled release can also be a gradient release in which the concentration of the therapeutic agent released varies over time or a steady state release in which the therapeutic agent is released in equal amounts over a certain period of time (with or without an initial burst release).

As used herein, the phrase "therapeutic agent" refers to any implantable pharmaceutically active agent intended to provide therapeutic effect on the body to treat or prevent conditions or diseases.

An "anti-proliferative" agent indicates any molecule that acts to inhibit cell proliferative events. Examples of anti-proliferative agents include microtubule inhibitors such as vinblastine, vincristine, colchicine and paclitaxel, or other agents such as cisplatin.

The term "pharmaceutically acceptable," as used herein, refers to those compounds of the present invention which are, within the scope of sound medical judgment, suitable for use in contact with the tissues of humans and lower mammals without undue toxicity, irritation, and allergic response, are commensurate with a reasonable benefit/risk ratio.

When naming substances that can exist in multiple enantiomeric forms, reference to the name of the substance without an enantiomeric designation, such as (d) or (l), refers herein to the genus of substances including the (d) form, the (l) form and the racemic mixture (e.g., d,l), unless otherwise specified. For example, recitation of "poly(lacetic acid)," unless otherwise indicated, refers to a compound selected from the group consisting of: poly(L-lacetic acid), poly(D-lacetic acid) and poly(D,L-lacetic acid). Similarly, generic reference to compounds that can exist in two or more polymorphs is understood to refer to the genus consisting of each individual polymorph species and any combinations or mixtures thereof.

As used herein, "derivative" refers to a chemically or biologically modified version of a chemical compound that is structurally similar to a parent compound and (actually or theoretically) derivable from that parent compound. A derivative may or may not have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group). For example, a hydrogen may be substituted with a halogen, such as fluorine or chlorine, or a hydroxyl group (—OH) may be replaced with a carboxylic acid moiety (—COOH). The term "derivative" also includes conjugates, and prodrugs of a parent compound (i.e., chemically modified derivatives which can be converted into the original compound under physiological conditions). For example, the prodrug may be an inactive form of an active agent. Under physiological conditions, the prodrug may be converted into the active form of the compound. Prodrugs may be formed, for example, by replacing one or two hydrogen atoms on nitrogen atoms by an acyl group (acyl prodrugs) or a carbamate group (carbamate prodrugs). More detailed information relating to prodrugs is found, for example, in Fleisher et al., Advanced Drug Delivery Reviews 19 (1996) 115; Design of Prodrugs, H. Bundgaard (ed.), Elsevier, 1985; or H. Bundgaard, Drugs of the Future 16 (1991) 443. The term "derivative" is also used to describe all solvates, for example hydrates or adducts (e.g., adducts with alcohols), active metabolites, and salts of the parent compound. The type of salt that may be prepared depends on the nature of the moieties within the compound. For example, acidic groups, for example carboxylic acid groups, can form alkali metal salts or alkaline earth metal salts (e.g., sodium salts, potassium salts, magnesium salts and calcium salts, as well as salts with physiologically tolerable quaternary ammonium ions and acid addition salts with ammonia and physiologically tolerable organic amines such as triethylamine, ethanolamine or tris-(2-hydroxyethyl) amine). Basic groups can form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds which simultaneously contain a basic group and an acidic group, for example a carboxyl group in addition to basic nitrogen atoms, can be present as zwitterions. Salts can be obtained by customary methods known to those skilled in the art, for example by combining a compound with an inorganic or organic acid or base in a solvent or diluent, or from other salts by cation exchange or anion exchange.

As used herein, "analog" or "analogue" refer to a chemical compound that is structurally similar to another but differs slightly in composition (as in the replacement of one atom by an atom of a different element or in the presence of a particular functional group), but may or may not be derivable from the parent compound. A "derivative" differs from an "analog" in that a parent compound may be the starting material to generate a "derivative," whereas the parent compound may not necessarily be used as the starting material to generate an "analogue."

Any concentration ranges, percentage range, or ratio range recited herein are to be understood to include concentrations, percentages or ratios of any integer within that range and fractions thereof, such as one tenth and one hundredth of an integer, unless otherwise indicated. Also, any number range recited herein relating to any physical feature, such as polymer subunits, size or thickness, are to be understood to include any integer within the recited range, unless otherwise indicated. It should be understood that the terms "a" and "an" as used above and elsewhere herein refer to "one or more" of the enumerated components. For example, "a" polymer refers to one polymer or a mixture comprising two or more polymers.

As used herein, the term "solid form" in reference to a taxane molecules refers to an arrangement of molecules comprising a core taxane structure in the solid phase, including any polymorph or solvate crystal solid structure. Solid forms can include crystalline or non-crystalline molecular arrangements. Examples of solid forms of taxane molecules include anhydrous paclitaxel, amorphous paclitaxel and dihydrate paclitaxel.

As used herein, the term "polymorph" refers to a particular solid form of a taxane therapeutic agent, having particular physical properties such as X-ray diffraction, IR spectra, melting point, and the like. Polymorphs include solvate crystalline solid forms, amorphous solid forms and anhydrous solid forms of a taxane therapeutic agent. The polymorphs may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers. In addition, the polymorphs disclosed herein may exist as tautomers and both tautomeric forms are intended to be encompassed by the scope of the invention, even though only one tautomeric structure is depicted.

Taxane Therapeutic Agents

The present invention relates to compositions comprising taxane therapeutic agents ("taxanes"), such as paclitaxel. Taxanes in general and paclitaxel in particular, are taxane therapeutic compounds considered to function as a cell cycle inhibitors by acting as an anti-microtubule agent, and more specifically as a stabilizer. As used herein, the term "paclitaxel" refers to a compound of the chemical structure shown as structure (1) below, consisting of a core structure with four fused rings ("core taxane structure," shaded in structure (1)), with several substituents.

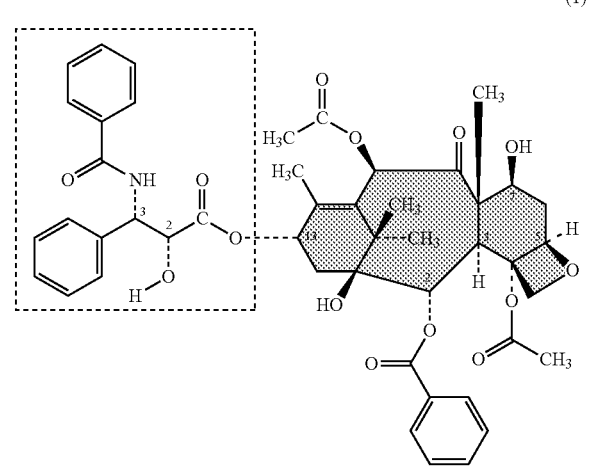

(1)

Other taxane analog or derivative compounds are characterized by variation of the paclitaxel structure (1). Preferred taxane analogs and derivatives core vary the substituents attached to the core taxane structure. In one embodiment, the therapeutic agent is a taxane analog or derivative including the core taxane structure (1) and the methyl 3-(benzamido)-2-hydroxy-3-phenylpropanoate moiety (shown in structure (2) below) at the 13-carbon position ("C13") of the core taxane structure (outlined with a dashed line in structure (1)).

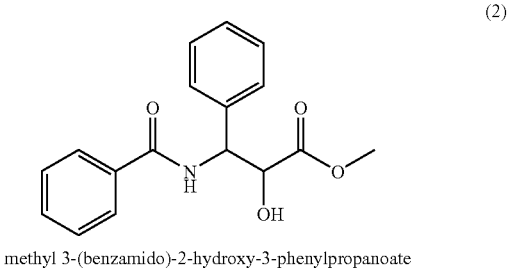

(2)

methyl 3-(benzamido)-2-hydroxy-3-phenylpropanoate

It is believed that structure (2) at the 13-carbon position of the core taxane structure plays a role in the biological activity of the molecule as a cell cycle inhibitor. Examples of therapeutic agents having structure (2) include paclitaxel (Merck Index entry 7117), docetaxol (TAXOTERE, Merck Index entry 3458), and 3'-desphenyl-3'-(4-ntirophenyl)-N-debenzoyl-N-(t-butoxycarbonyl)-10-deacetyltaxol.

Representative examples of paclitaxel derivatives or analogues that can be used as therapeutic agents include 7-deoxy-docetaxol, 7,8-cyclopropataxanes, N-substituted 2-azetidones, 6,7-epoxy paclitaxels, 6,7-modified paclitaxels, 10-desacetoxytaxol, 10-deacetyltaxol (from 10-deacetyl-baccatin III), phosphonooxy and carbonate derivatives of taxol, taxol 2',7-di(sodium 1,2-benzenedicarboxylate, 10-desacetoxy-11,12-dihydrotaxol-10,12(18)-diene derivatives, 10-desacetoxytaxol, Protaxol (2'- and/or 7-O-ester derivatives), (2'-and/or 7-O-carbonate derivatives), asymmetric synthesis of taxol side chain, fluoro taxols, 9-deoxotaxane, (13-acetyl-9-deoxobaccatine III, 9-deoxotaxol, 7-deoxy-9-deoxotaxol, 10-desacetoxy-7-deoxy-9-deoxotaxol), derivatives containing hydrogen or acetyl group and a hydroxy and tert-butoxycarbonylamino, sulfonated 2'-acryloyltaxol and sulfonated 2'-O-acyl acid taxol derivatives, succinyltaxol, 2'-γ-aminobutyryltaxol formate, 2'-acetyl taxol, 7-acetyl taxol, 7-glycine carbamate taxol, 2'-OH-7-PEG(5000) carbamate taxol, 2'-benzoyl and 2',7-dibenzoyl taxol derivatives, other prodrugs (2'-acetyltaxol; 2',7-diacetyltaxol; 2'succinyl-taxol; 2'-(beta-alanyl)-taxol); 2'gamma-aminobutyryltaxol formate; ethylene glycol derivatives of 2'-succinyltaxol; 2'-glutaryltaxol; 2'-(N,N-dimethylglycyl)taxol; 2'-(2-(N,N-dimethylamino)propionyl)taxol; 2'orthocarboxybenzoyl taxol; 2'aliphatic carboxylic acid derivatives of taxol, Prodrugs {2'(N,N-diethylaminopropionyl)taxol, 2'(N,N-dimethylglycyl)taxol, 7(N,N-dimethylglycyl)taxol, 2',7-di-(N,N-dimethylglycyl)taxol, 7(N,N-diethylaminopropionyl)taxol, 2',7-di(N,N-diethylaminopropionyl)taxol, 2'-(L-glycyl) taxol, 7-(L-glycyl)taxol, 2',7-di(L-glycyl)taxol, 2'-(L-alanyl) taxol, 7-(L-alanyl)taxol, 2',7-di(L-alanyl)taxol, 2'-(L-leucyl) taxol, 7-(L-leucyl)taxol, 2',7-di(L-leucyl)taxol, 2'-(L-isoleucyl)taxol, 7-(L-isoleucyl)taxol, 2',7-di(L-isoleucyl) taxol, 2'-(L-valyl)taxol, 7-(L-valyl)taxol, 2'7-di(L-valyl) taxol, 2'-(L-phenylalanyl)taxol, 7-(L-phenylalanyl)taxol, 2',7-di(L-phenylalanyl)taxol, 2'-(L-prolyl)taxol, 7-(L-prolyl) taxol, 2',7-di(L-prolyl)taxol, 2'-(L-lysyl)taxol, 7-(L-lysyl) taxol, 2',7-di(L-lysyl)taxol, 2'-(L-glutamyl)taxol, 7-(L-glutamyl)taxol, 2',7-di(L-glutamyl)taxol, 2'-(L-arginyl) taxol, 7-(L-arginyl)taxol, 2',7-di(L-arginyl)taxol}, taxol analogues with modified phenylisoserine side chains, TAXOTERE, (N-debenzoyl-N-tert-(butoxycaronyl)-10-deacetyltaxol, and taxanes (e.g., baccatin III, cephalomannine, 10-deacetylbaccatin III, brevifoliol, yunantaxusin and taxusin); and other taxane analogues and derivatives, including 14-beta-hydroxy-10 deacetybaccatin III, debenzoyl-2-acyl paclitaxel derivatives, benzoate paclitaxel derivatives, phosphonooxy and carbonate paclitaxel derivatives, sulfonated 2'-acryloyltaxol; sulfonated 2'-O-acyl acid paclitaxel derivatives, 18-site-substituted paclitaxel derivatives, chlorinated paclitaxel analogues, C4 methoxy ether paclitaxel derivatives, sulfenamide taxane derivatives, brominated paclitaxel analogues, Girard taxane derivatives, nitrophenyl paclitaxel, 10-deacetylated substituted paclitaxel derivatives, 14-beta-hydroxy-10 deacetylbaccatin III taxane derivatives, C7 taxane derivatives, C10 taxane derivatives, 2-debenzoyl-2-acyl taxane derivatives, 2-debenzoyl and -2-acyl paclitaxel derivatives, taxane and baccatin III analogues bearing new C2 and C4 functional groups, n-acyl paclitaxel analogues, 10-deacetylbaccatin III and 7-protected-10-deacetylbaccatin III derivatives from 10-deacetyl taxol A, 10-deacetyl taxol B, and 10-deacetyl taxol, benzoate derivatives of taxol, 2-aroyl-4-acyl paclitaxel analogues, orthro-ester paclitaxel analogues, 2-aroyl-4-acyl paclitaxel analogues and 1-deoxy paclitaxel and 1-deoxy paclitaxel analogues.

A composition comprising a taxane compound can include formulations, prodrugs, analogues and derivatives of paclitaxel such as, for example, TAXOL (Bristol Myers Squibb, New York, N.Y.), TAXOTERE (Aventis Pharmaceuticals, France), docetaxel, 10-desacetyl analogues of paclitaxel and 3'N-desbenzoyl-3'N-t-butoxy carbonyl analogues of paclitaxel. Paclitaxel has a molecular weight of about 853 amu, and may be readily prepared utilizing techniques known to those skilled in the art (see, e.g., Schiff et al., Nature 277: 665-667, 1979; Long and Fairchild, Cancer Research 54: 4355-4361, 1994; Ringel and Horwitz, J. Nat'l Cancer Inst. 83 (4): 288-291, 1991; Pazdur et al., Cancer Treat. Rev. 19 (4): 351-386, 1993; WO 94/07882; WO 94/07881; WO 94/07880; WO 94/07876; WO 93/23555; WO 93/10076; WO94/00156; WO 93/24476; EP 590267; WO 94/20089; U.S. Pat. Nos. 5,294,637; 5,283,253; 5,279,949; 5,274,137; 5,202,448; 5,200,534; 5,229,529; 5,254,580; 5,412,092; 5,395,850; 5,380,751; 5,350,866; 4,857,653; 5,272,171; 5,411,984; 5,248,796; 5,248,796; 5,422,364; 5,300,638; 5,294,637; 5,362,831; 5,440,056; 4,814,470; 5,278,324; 5,352,805; 5,411,984; 5,059,699; 4,942,184; Tetrahedron Letters 35 (52): 9709-9712, 1994; J. Med. Chem. 35: 4230-4237, 1992; J. Med. Chem. 34: 992-998, 1991; J. Natural Prod. 57 (10): 1404-1410, 1994; and J. Natural Prod. 57 (11): 1580-1583, 1994; J. Am. Chem. Soc. 110: 6558-6560, 1988), or obtained from a variety of commercial sources, including for example, Sigma Chemical Co., St. Louis, Mo. (T7402—from *Taxus brevifolia*).

In one aspect, the therapeutic agent is selected from the taxane analogues and derivatives disclosed in U.S. Pat. No. 5,440,056 as having the structure (3):

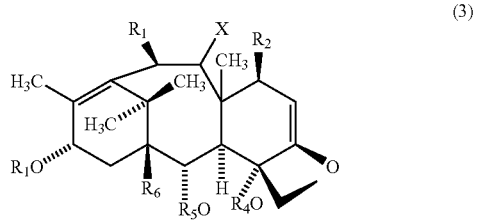

wherein X may be oxygen (paclitaxel), hydrogen (9-deoxy derivatives), thioacyl, or dihydroxyl precursors; $R_1$ is selected from paclitaxel or TAXOTERE side chains or alkanoyl of the formula (4):

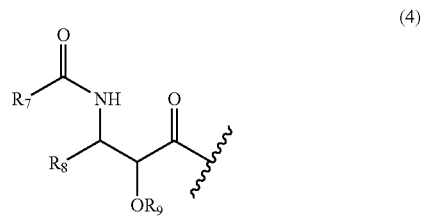

wherein $R_7$ is selected from hydrogen, alkyl, phenyl, alkoxy, amino, phenoxy (substituted or unsubstituted); $R_8$ is selected from hydrogen, alkyl, hydroxyalkyl, alkoxyalkyl, aminoalkyl, phenyl (substituted or unsubstituted), alpha or beta-naphthyl; and $R_9$ is selected from hydrogen, alkanoyl, substituted alkanoyl, and aminoalkanoyl; where substitutions refer to hydroxyl, sulfhydryl, allalkoxyl, carboxyl, halogen, thioalkoxyl, N,N-dimethylamino, alkylamino, dialkylamino, nitro, and —$OSO_3H$, and/or may refer to groups containing such substitutions; $R_2$ is selected from hydrogen or oxygen-containing groups, such as hydrogen, hydroxyl, alkoyl, alkanoyloxy, aminoalkanoyloxy, and peptidyalkanoyloxy; $R_3$ is selected from hydrogen or oxygen-containing groups, such as hydrogen, hydroxyl, alkoyl, alkanoyloxy, aminoalkanoyloxy, and peptidyalkanoyloxy, and may further be a silyl containing group or a sulphur containing group; $R_4$ is selected from acyl, alkyl, alkanoyl, aminoalkanoyl, peptidyalkanoyl and aroyl; $R_5$ is selected from acyl, alkyl, alkanoyl, aminoalkanoyl, peptidylalkanoyl and aroyl; $R_6$ is selected from hydrogen or oxygen-containing groups, such as hydrogen, hydroxyl alkoyl, alkanoyloxy, aminoalkanoyloxy, and peptidyalkanoyloxy.

In one aspect, the therapeutic agent is selected from the paclitaxel analogues and derivatives disclosed in PCT International Patent Application No. WO 93/10076 as cell cycle inhibitors. The analogue or derivative may have a side chain attached to the taxane nucleus at C13, as shown in the structure below (formula 5), in order to confer antitumor activity to the taxane.

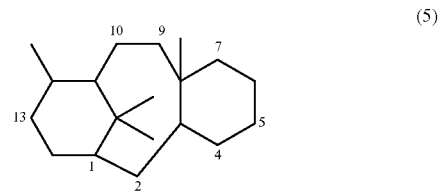

WO 93/10076 discloses that the taxane nucleus may be substituted at any position with the exception of the existing methyl groups. The substitutions may include, for example, hydrogen, alkanoyloxy, alkenoyloxy, aryloyloxy. In addition, oxo groups may be attached to carbons labeled 2, 4, 9, and/or 10. As well, an oxetane ring may be attached at carbons 4 and 5. As well, an oxirane ring may be attached to the carbon labeled 4. In one aspect, the taxane-based cell cycle inhibitor useful in the present invention is disclosed in U.S. Pat. No. 5,440,056, which discloses 9-deoxo taxanes. These are compounds lacking an oxo group at the carbon labeled 9 in the taxane structure shown above in formula (5). The taxane ring may also be substituted at the carbons labeled 1, 7 and 10 (independently) with H, OH, O—R, or O—CO—R where R is an alkyl or an aminoalkyl. As well, it may be substituted at carbons labeled 2 and 4 (independently) with aryol, alkanoyl, aminoalkanoyl or alkyl groups. The side chain of formula (4) may be substituted at $R_7$ and $R_8$ (independently) with phenyl rings, substituted phenyl rings, linear alkanes/alkenes, and groups containing H, O or N. $R_9$ may be substituted with H, or a substituted or unsubstituted alkanoyl group.

Taxane Therapeutic Agent Coating Configurations

Various medical devices having a coating comprising a taxane therapeutic agent are provided. The medical device preferably comprises a coating having one or more layers. Preferably, the coating includes one or more solid forms of a taxane therapeutic agent described with respect to the first embodiment.

Figure 1B:
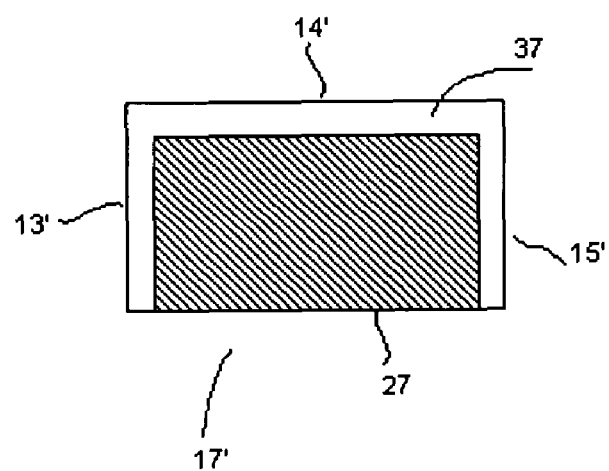
FIG. 1B shows a cross sectional view of a portion of the medical device of FIG. 1A.

FIG. 1A shows a coated medical device comprising a self-expanding vascular stent 10 having a luminal surface 12 and a coating 37 applied to the abluminal surface 14. The vascular stent 10 extends from a proximal end 13 to a distal end 15. The vascular stent 10 has a tubular shape formed from a series of joined hoops 16 formed from interconnected struts 17 and bends 18, and defines the interior lumen. FIG. 1B shows a cross section along line A-A' of coated strut 17' from the vascular stent 10 shown in FIG. 1A. Referring to FIG. 1B, the strut 17' can have any suitable cross sectional configuration, such as a rectangular cross section, and can be formed from any suitable material 27 such as a nickel titanium alloy, stainless steel or a cobalt chromium alloy. The abluminal surface 14', including the proximal edge 13' and distal edge 15', are coated with the coating 37 adhered to the abluminal surface of the vascular stent 10. Preferably, the coating 37 includes one or more solid forms of a taxane therapeutic agent, such as paclitaxel. In one aspect, the coating 37 can consist essentially of a single solid form of the taxane therapeutic agent, such as a dihydrate solvated paclitaxel. In another aspect, the coating 37 includes a single layer comprising a mixture of two or more solid forms of the taxane therapeutic agent, such as a mixture of dihydrate solvated paclitaxel and amorphous paclitaxel. In yet another aspect, the coating 37 can include two or more coating layers each comprising one or more solid forms of the taxane therapeutic agent. Each coating layer may be distinguished, for example, by different elution rates resulting from different solid form structure(s) in each layer. The coating 37 can also include non-taxane components, such as biostable or bioabsorbable polymers, in separate layers from or combined with a taxane therapeutic agent.

The coating is preferably a single-layer of a therapeutically effective amount of the taxane therapeutic agent. Preferably, the single-layer consists of the taxane therapeutic agent in one or more solid forms. The therapeutically effective amount can depend upon the type and severity of the condition to be treated; the type and activity of the specific therapeutic agent employed; the method by which the medical device is administered to the patient; the age, body weight, general health, gender and diet of the patient; the time of administration, route of administration, and rate of excretion of the specific compound employed; the duration of the treatment; drugs used in combination or coincidental with the specific compound employed; and like factors well known in the medical arts.

To obtain the desired dosage of therapeutic agent, the solid form of the taxane therapeutic agent in the coating may be varied. In one embodiment, the coating contains from about 0.01 µg to about 10 µg of the taxane therapeutic agent per mm² of the surface area of the structure, preferably about 0.05 µg to about 5 µg, about 0.03 µg to about 3 µg, about 0.05 µg to about 3 µg, about 0.5 µg to about 4.0 µg, most preferably between about 0.5 and 3.0 µg, of the taxane therapeutic agent per mm2 of the abluminal surface area of the structure. Desirably, a total of about 1-500 µg of a taxane therapeutic agent (such as paclitaxel) is coated on one or more surface of a medical device.

The thickness of the coating layer comprising the taxane therapeutic agent is between 0.1 µm and 20 µm, between 0.1 µm and 10 µm, or between 0.1 µm and 5 µm. For the purposes of local delivery from a stent, the daily dose that a patient will receive depends at least on the length of the stent. The total coating thickness is preferably about 50 µm or less, preferably less than about 20 µm and most preferably about 0.1-10 µm.

For example, a 6×20 mm stent may be coated with about 0.05-5 µg/mm² of paclitaxel, more preferably about 0.5-3 µg/mm², can be applied to the abluminal surface of the stent. Particularly preferred doses of a taxane therapeutic agent on the abluminal surface of a stent include: 0.06, 0.30, 1.00 and 3.00 µg/mm². In another embodiment, the abluminal side of a 6×20 mm stent (surface area of about 73 mm²) is coated with about 20-220 µg of paclitaxel. Examples of particularly preferred coating for a 6×20 mm vascular stent having an abluminal surface area of about 73 mm², and a compressed diameter of about 7F are listed in Table 5 below. Preferred spray solutions for obtaining durable coating are also listed in Table 5, along with the preferred resulting minimum ratio of dihydrate to amorphous solid forms obtained by ultrasonic spray coating of the preferred solution.

In another aspect of the first embodiment, a coating may include two or more coating layers each comprising or consisting essentially of a taxane therapeutic agent in one or more solid forms. Preferred multilayer coatings include an outer layer comprising an amorphous solid form of a taxane therapeutic agent. The outer layer preferably covers the exposed surface of the underlying coating layer(s). The outer layer can optionally include a mixture of other solid forms of the taxane therapeutic agent with the amorphous solid form. Multilayer coatings can include any number of coating layers beneath the outer coating, including 2, 3, 4, 5, 6, 7, and 8 layer coatings. One preferred two-layer coating configuration includes a first layer consisting essentially of a dihydrate paclitaxel solid form, and a second layer comprising an amorphous paclitaxel solid form. The second layer can be a mixture of the amorphous and the dihydrate solid forms of paclitaxel.

The coated medical device may also include a taxane therapeutic agent at least partially contained within the medical device 10 frame material 27. The medical device may have pores, holes, wells, slots, grooves, or the like for containing the therapeutic agent and/or other materials such as a polymer (see, e.g., co-pending U.S. patent application Ser. No. 10/870,079, filed Jun. 17, 2004 and incorporated herein by reference). Alternatively, the therapeutic agent and/or polymer may be incorporated into a biodegradable medical device that releases the agent as the device degrades, or the therapeutic agent and/or polymer may be incorporated into or placed on the medical device in any other known manner. A medical device containing a therapeutic agent within the device itself may also have deposited on the device a therapeutic layer, a polymer layer, a layer containing both a therapeutic agent and a polymer, or any combination of these.

Optionally, a polymer may also be deposited on the surface of the medical device prior to during or after deposition of a therapeutic agent. The polymer may comprise, for example, silane, acrylate polymer/copolymer, acrylate carboxyl and/or hydroxyl copolymer, polyvinylpyrrolidone/vinylacetate copolymer (PVPNA), olefin acrylic acid copolymer, ethylene acrylic acid copolymer, epoxy polymer, polyethylene glycol, parylene or a parylene derivative, polyethylene oxide, polyvinylpyridine copolymers, polyamide polymers/copolymers polyimide polymers/copolymers, ethylene vinylacetate copolymer and/or polyether sulfones the polymer(s) may be mixed with or in a separate layer(s) from the therapeutic agent.

Solid Forms of Taxane Therapeutic Agent Compositions

Figure 2:
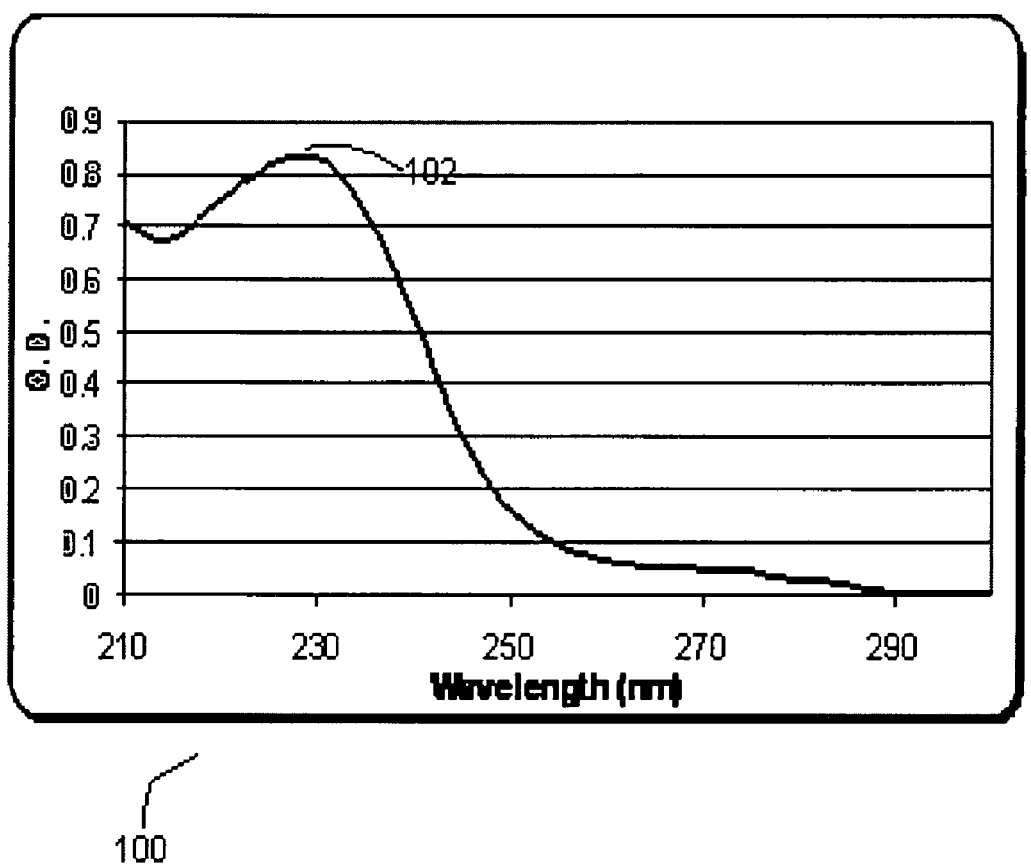
FIG. 2 shows an ultraviolet (UV) absorption spectrum of paclitaxel in ethanol.

The different solid forms of the taxane therapeutic agent preferably contain one or more types of taxane molecules sharing a common core taxane structure. The core taxane structure can be identified from an ultraviolet (UV) spectrum of the taxane therapeutic agent in any suitable elution medium that permits measurement of a characteristic peak of the taxane therapeutic agent in solution. Methanol and ethanol are preferred examples of suitable solvents. FIG. 2 shows an ultraviolet (UV) spectrum 100 (Agilent In-line UV Spectrophotometer) of paclitaxel in ethanol, obtained from a 25.67 µM solution of paclitaxel in ethanol. Paclitaxel provides a characteristic peak at 227 nm (102) indicative of the presence of the core taxane structure of paclitaxel in the solution. Taxane therapeutic agent in solution can be identified from a UV spectrum of the elution medium comprising the characteristic peak at about 227 nm, which can be correlated to the presence of the taxane therapeutic agent in the solution, regardless of the solid form from which the taxane molecule originated.

A first embodiment provides compositions comprising one or more taxane therapeutic agents in one or more solid forms. Preferably, the taxane solid forms are selected from the group consisting of: amorphous taxane therapeutic agent, anhydrous taxane therapeutic agent and dihydrate therapeutic agent. The taxane therapeutic agent is preferably paclitaxel. Solid forms of taxane therapeutic agents in medical device coatings can have identical molecular structures, but differ in the arrangement of the taxane molecules in the coating. Various solid forms of the taxane therapeutic agent can be identified and differentiated on the basis of one or more physical properties including melting point, solubility and appearance. In addition, various other analytical methods can be used to identify different solid forms of the taxane therapeutic agents, including vibrational spectroscopy (e.g., Raman or Infrared Spectra), solubilities, melting points, X-ray Diffraction (XRD), $^{13}$C Nuclear Magnetic Resonance (NMR), and Temperature Programmed Desorption (TPD)).

Three different solid forms of the taxane therapeutic agent (amorphous, anhydrous or dihydrate) can be formed by dissolving the solid taxane therapeutic agent, typically obtained in the anhydrous form, in different solvents, as described below. These three solid forms of paclitaxel can be prepared and identified by the methods described in J. H. Lee et al., "Preparation and Characterization of Solvent Induced Dihydrated, Anhydrous and Amorphous Paclitaxel," *Bull. Korean Chem. Soc.*, v. 22, no. 8, pp. 925-928 (2001), which is incorporated herein by reference in its entirety.

Figure 3A:
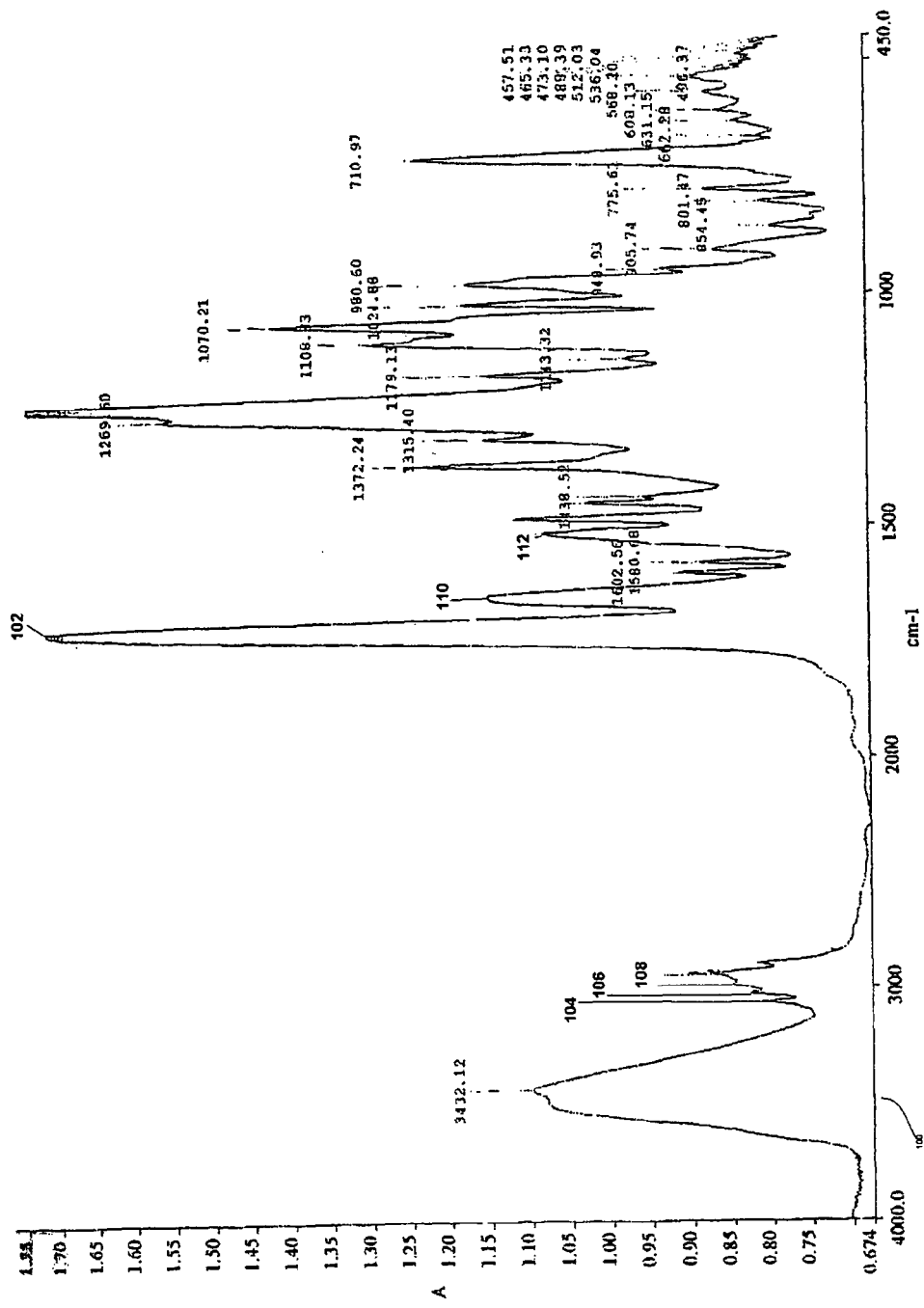
FIG. 3A shows an infrared spectrum of a first solid form of paclitaxel.

In a first aspect of the first embodiment, the composition comprises an amorphous taxane therapeutic agent, such as amorphous paclitaxel ("aPTX"). Bulk amorphous paclitaxel can be prepared by dissolving the taxane therapeutic agent in any suitable aprotic organic solvent, preferably in methylene chloride (dichloromethane), followed by removal of the solvent to leave an amorphous solid. Chloroform can also be used as the organic solvent. For example, amorphous taxane therapeutic agent can be formed by first dissolving the solid taxane therapeutic agent in dichloromethane, followed by crystallization at and evaporation of the dichloromethane and subsequent vacuum drying of the sample. Desirably, the synthesis method is carried out in a low humidity environment (preferably below about 40% relative humidity, more preferably below about 30% and most preferably below about 20% relative humidity or less), and at about 23° C. FIG. 3A shows an infrared vibrational spectrum of an amorphous paclitaxel prepared according the method of Example 1. The spectrum of amorphous paclitaxel 100 includes a single broad peak at about 1723 cm$^{-1}$ (102), as well as the following other characteristic peaks: 3064 cm$^{-1}$ (104), 3029 cm$^{-1}$ (106), 2942 cm$^{-1}$ (108), 1650 cm$^{-1}$ (110), and 1517 cm$^{-1}$ (112). The melting points of the amorphous paclitaxel samples prepared according to Example 1 were about 190° C.-210° C. An amorphous taxane therapeutic agent can be identified by the presence of a single broad peak between about 1700-1740 cm$^{-1}$ in the infrared spectrum, typically at about 1723 cm$^{-1}$. The amorphous taxane therapeutic agent was found to be more soluble in porcine serum than the dihydrate taxane therapeutic agent, but less soluble than the anhydrous taxane therapeutic agent.

Figure 3B:
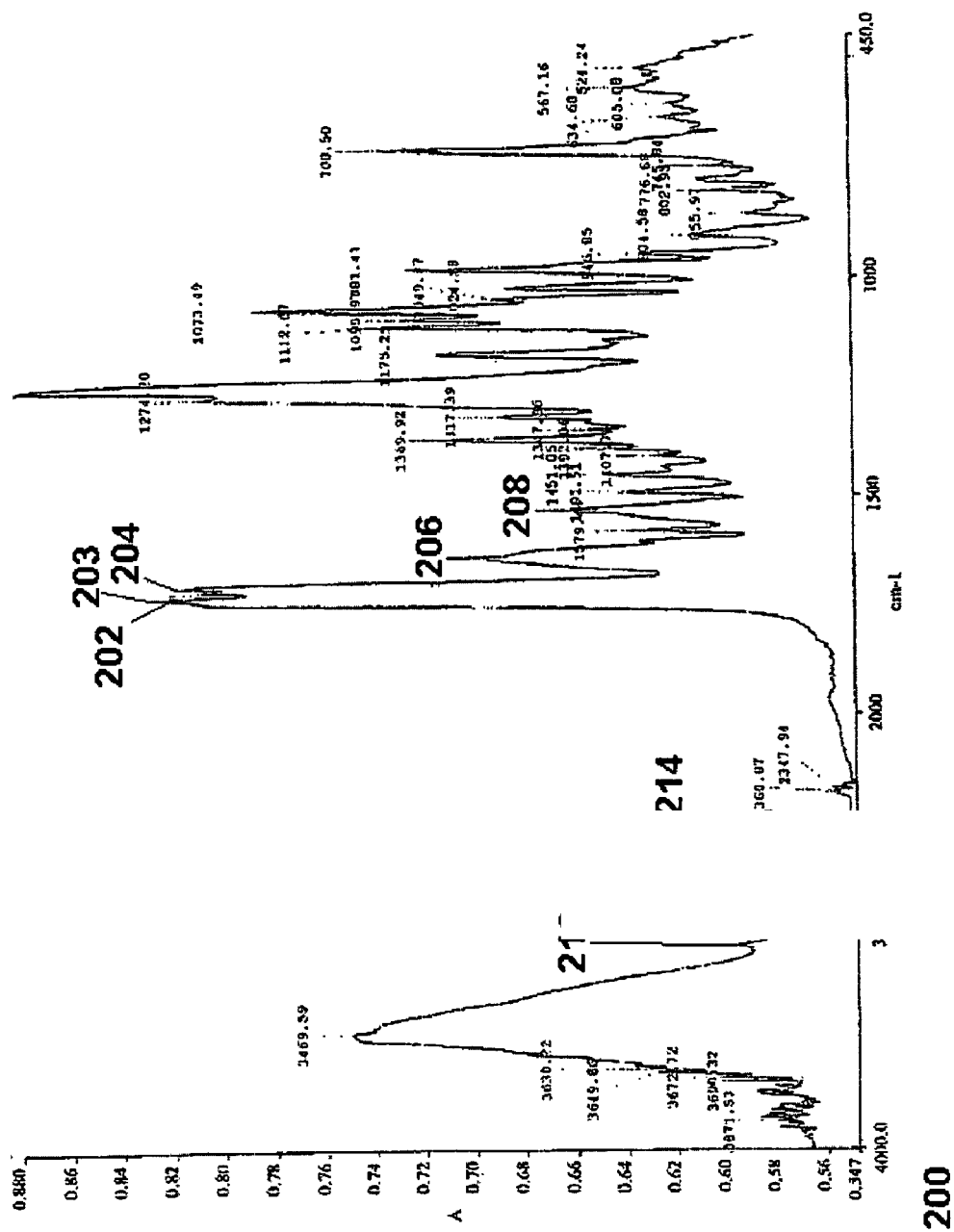
FIG. 3B shows an infrared spectrum of a second solid form of paclitaxel.

In a second aspect of the first embodiment, the composition comprises a solvated taxane therapeutic agent, such as dihydrate paclitaxel ("dPTX"). Bulk samples of dihydrate paclitaxel can be prepared by dissolving the taxane therapeutic agent in any suitable alcohol-based solvent, followed by evaporation of the solvent to leave a crystalline solid. Typically, the taxane therapeutic agent is first dissolved in a methanol solvent, followed by the gradual addition of water to the solution. Dihydrate taxane therapeutic agent is preferably formed by a multi-step process: (1) first, dissolving a solid anhydrous taxane therapeutic agent in methanol to form a solution, followed by (2) adding water to the solution in a step-wise manner, followed by (3) crystallization. The water is preferably added very slowly, in a drop-by-drop manner, waiting for solution to become clear before the addition of the next drop of water, until the solution includes 80% v/v methanol and 20% v/v water. The dihydrate taxane therapeutic agent can be collected by filtration and vacuum evaporation of the methanol and water. Desirably, the synthesis method is carried out in a high humidity environment (preferably at least about 20% relative humidity, more preferably about 40% or greater relative humidity), and at temperatures of about 23° C., or higher. Alternatively, studies have reported formation of paclitaxel dihydrate by incubation of anhydrous paclitaxel in water for 24 hours at 25° C. See, e.g., R. T. Liggins et al., "Solid-State Characterization of Paclitaxel," *Journal of Pharmaceutical Sciences*, v. 86, No. 12, p. 1461 (December 1997). The dihydrate paclitaxel prepared according to Example 1 was characterized by Infrared Spectrophotometry. FIG. 3B shows an infrared vibrational spectrum of an dihydrate paclitaxel prepared according the method of Example 1. The spectrum of dihydrate paclitaxel 200 includes three or more peaks between about 1700-1740 cm$^{-1}$, typically three peaks at about 1705 cm$^{-1}$ (204), about 1716 cm$^{-1}$ (203) and about 1731 cm$^{-1}$ (202), as well as the following other characteristic peaks: 3067 cm$^{-1}$ (210), 3017 cm$^{-1}$ (212), 2963 cm$^{-1}$ (214), 1639 cm$^{-1}$ (206), and 1532 cm$^{-1}$ (208). The melting points of the dihydrate paclitaxel samples prepared according to Example 1 were about 209° C.-215° C. Dehydration of dihydrate paclitaxel has been reported during heating at a rate of 10° C./min over a temperature range of between about 35° C. and about 100° C. measured by DSC (with peaks observed at about 50° C. and about 72° C.), and between about 25° C. and about 85° C. measured by Thermogravimetric Analysis (TGA), with lower temperatures reported at slower heating rates. R. T. Liggins et al., "Solid-State Characterization of Paclitaxel," *Journal of Pharmaceutical Sciences*, v. 86, No. 12, pp. 1458-1463, 1461 (December 1997) ("Liggins"). The dihydrate paclitaxel has been reported to not show weight loss or evidence of dehydration when stored for several weeks when stored at 25° C. at 200 torr. Liggens et al., page 1461.

Figure 3C:
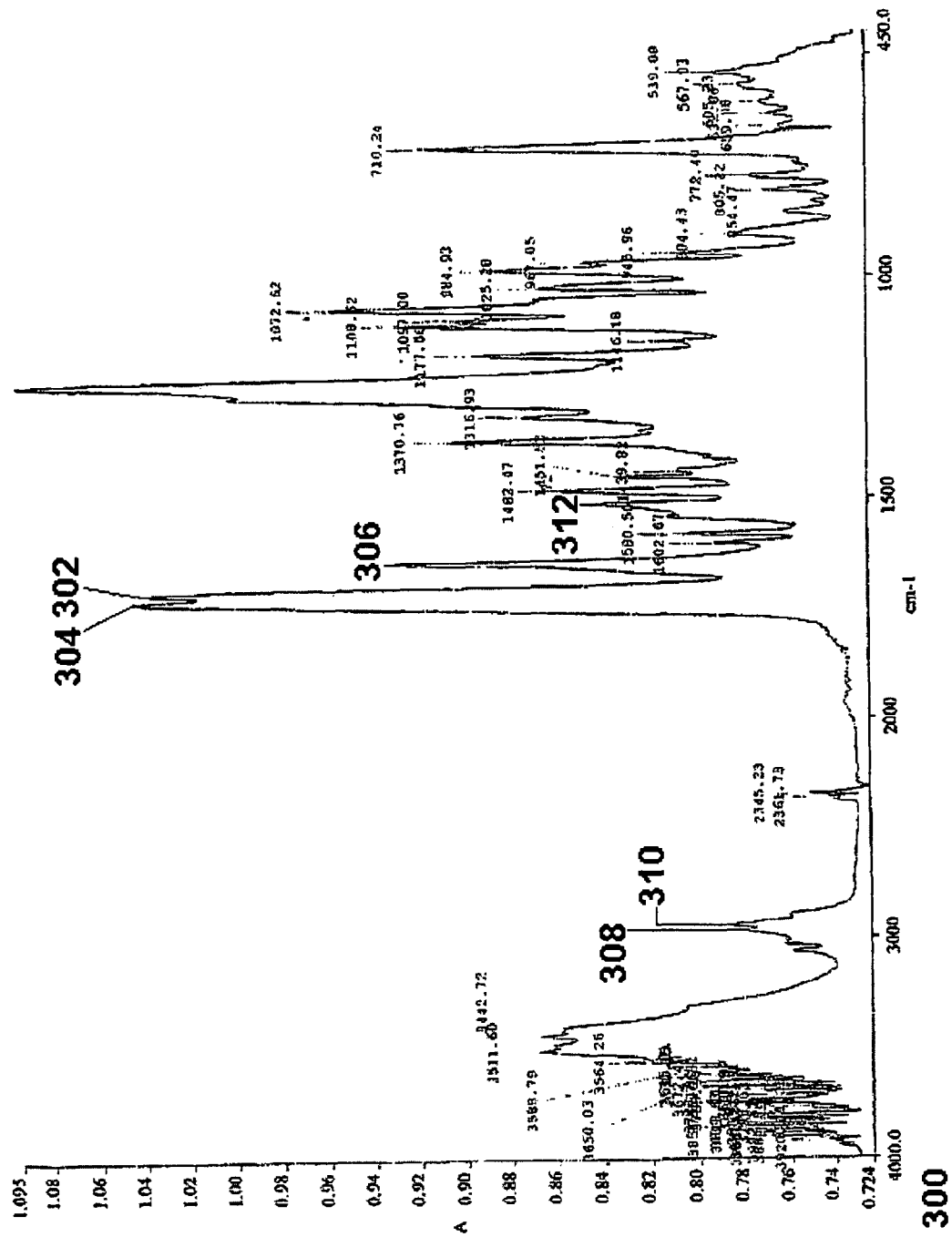
FIG. 3C shows an infrared spectrum of a third solid form of paclitaxel.

In a third aspect of the first embodiment, the composition comprises an anhydrous taxane therapeutic agent, such as anhydrous paclitaxel. Anhydrous taxane therapeutic agents preferably contain less than about 1.00% water (more preferably less than about 0.60%, 0.55% or 0.50% water), as measured by Karl Fischer analysis. Bulk samples of anhydrous taxane therapeutic agent can be prepared by dissolving a taxane therapeutic agent such as paclitaxel in any suitable alcohol-based solvent, followed by evaporation of the solvent to leave an anhydrous solid. Typically, the taxane therapeutic agent is first dissolved in a methanol solvent, followed by the gradual addition of hexane to the solution. For example, as described in more detail in Example 1, anhydrous taxane therapeutic agent can be formed by first dissolving paclitaxel in methanol to form a solution, followed by addition of hexane to the solution and subsequent evaporation of the methanol and hexane. Acetone, ethyl acetate or diethyl ether are also suitable solvents for combination with hexane in forming the anhydrous solid form of a taxane therapeutic agent. The dihydrate paclitaxel prepared according to Example 1 was characterized by Infrared Spectrophotometry. FIG. 3C shows an infrared vibrational spectrum of a anhydrous paclitaxel prepared according to the method of Example 1. The spectrum of anhydrous paclitaxel 300 includes a pair of peaks between about 1700-1740 cm$^{-1}$, typically two peaks at about 1714 cm$^{-1}$ (302) and about 1732 cm$^{-1}$ (304), as well as the following other characteristic peaks: 3065 cm$^{-1}$ (308), 2944 cm$^{-1}$ (310), 1646 cm$^{-1}$ (306), and 1514 cm$^{-1}$ (312). The melting points of the anhydrous paclitaxel samples prepared according to Example 1 were about 220° C.-221° C. The anhydrous taxane therapeutic agent was found to be more soluble in porcine serum than the amorphous taxane therapeutic agent, and significantly more soluble than the dihydrate taxane therapeutic agent.

Suitable solvent systems for the synthesis of amorphous, dihydrate and anhydrous taxane therapeutic solid forms, as well as characteristic melting point ranges and infrared spectrum peaks useful in identifying each solid form, are provided in Table 1. Other solvent systems can also be used to form one or more of the taxane solid forms described herein, and other IR peaks can be used to identify the type(s) of solid forms present in a taxane therapeutic agent solid sample.

TABLE 1

Preparation and Identification of Taxane Solid Forms

| | Desired Taxane Solid Form | | |
|---|---|---|---|
| | Amorphous | Dihydrate | Anhydrous |
| Solvent: | Dichloromethane | Methanol/Water | Methanol/Hexane |
| Melting Point: | 190-210° C. | 209-215° C. | 220-221° C. |
| Characteristic IR peaks: | Single peak between 1700-1740 cm$^{-1}$ 3064 cm$^{-1}$ (104), 3029 cm$^{-1}$ (106), 2942 cm$^{-1}$ (108) 1650 cm$^{-1}$ (110) 1517 cm$^{-1}$ (112) | Three or more peaks between 1700-1740 cm$^{-1}$ 3067 cm$^{-1}$ (210), 3017 cm$^{-1}$ (212), 2963 cm$^{-1}$ (214) 1639 cm$^{-1}$ (206) 1532 cm$^{-1}$ (208) | Two peaks between 1700-1740 cm$^{-1}$ 3065 cm$^{-1}$ (308), 2944 cm$^{-1}$ (310) 1646 cm$^{-1}$ (306) 1514 cm$^{-1}$ (312) |

Figure 4A:
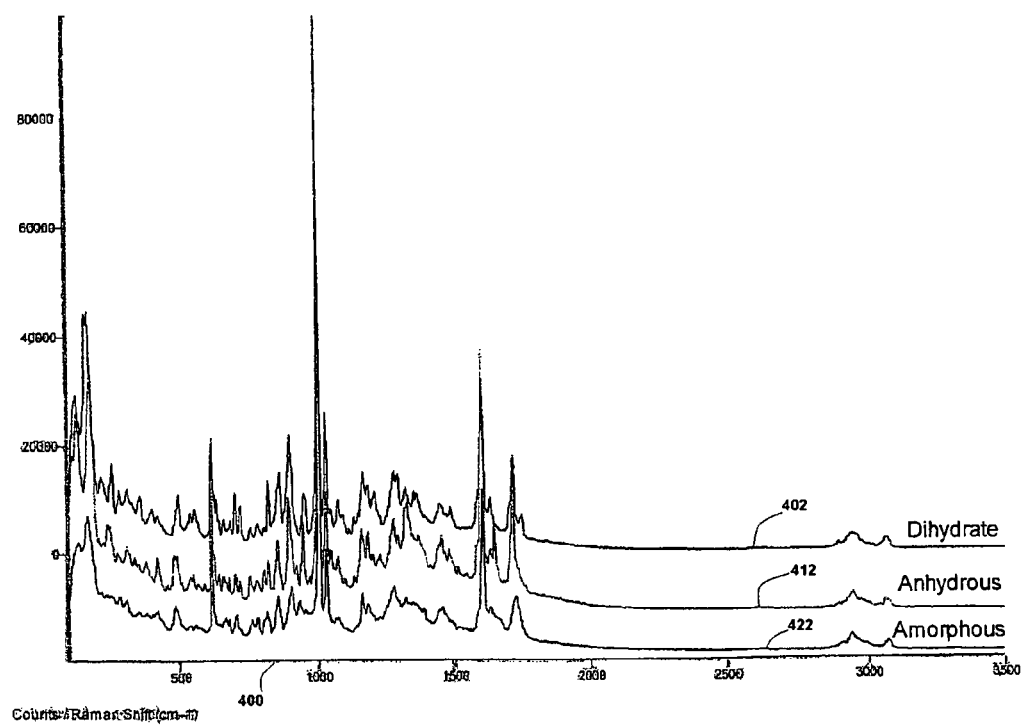
FIG. 4A shows a series of confocal Raman spectra for various solid forms of paclitaxel.

Differentiation of taxane solid states by vibrational spectroscopy can also be performed using Raman scattering. Raman scattering describes the phenomenon whereby incident light scattered by a molecule is shifted in wavelength from the incident wavelength. The magnitude of the wavelength shift depends on the vibrational motions the molecule is capable of undergoing, and this wavelength shift provides a sensitive measure of molecular structure. That portion of the scattered radiation having shorter wavelengths than the incident light is referred to as anti-Stokes scattering, and the scattered light having wavelengths longer than the incident beam as Stokes scattering. Raman scattering is a spectroscopic method useful for the detection of coatings, as the Raman spectra of different coatings or coating layers can be more distinct than the spectra obtained by direct light absorption or reflectance. FIG. 4A shows an overlay of three Raman spectral traces 400 recorded as an average of 10 spectra of three solid paclitaxel coatings on a stainless steel surface using a FT-Raman spectrometer, with excitation from a 532 nm laser with a power output of 8 mW. The three spectral traces correspond to the dihydrate (402), anhydrous (412) and amorphous (422) paclitaxel samples. Each spectral trace was collected over a 10 second integration each (total acquisition time of 100 seconds), using an air objective (100×, NA=0.9). Differences in the characteristic vibrational peaks can be used to differentiate the dihydrate, anhydrous and amorphous forms of the solid paclitaxel. The characteristic vibrational peaks correspond to the infrared characteristic peaks discussed with respect to the infrared spectra of FIGS. 3A-3C, and include the peaks listed in Table 1. Most notably, the presence of a single peak between 1700-1740 cm$^{-1}$ indicates the presence of an amorphous taxane therapeutic agent solid form, the presence of three or more peaks between 1700-1740 cm$^{-1}$ indicates the presence of the dihydrate taxane therapeutic agent solid form, and the presence of two peaks between 1700-1740 cm$^{-1}$ indicates the presence of the anhydrous taxane therapeutic agent solid form.

Figure 4B:
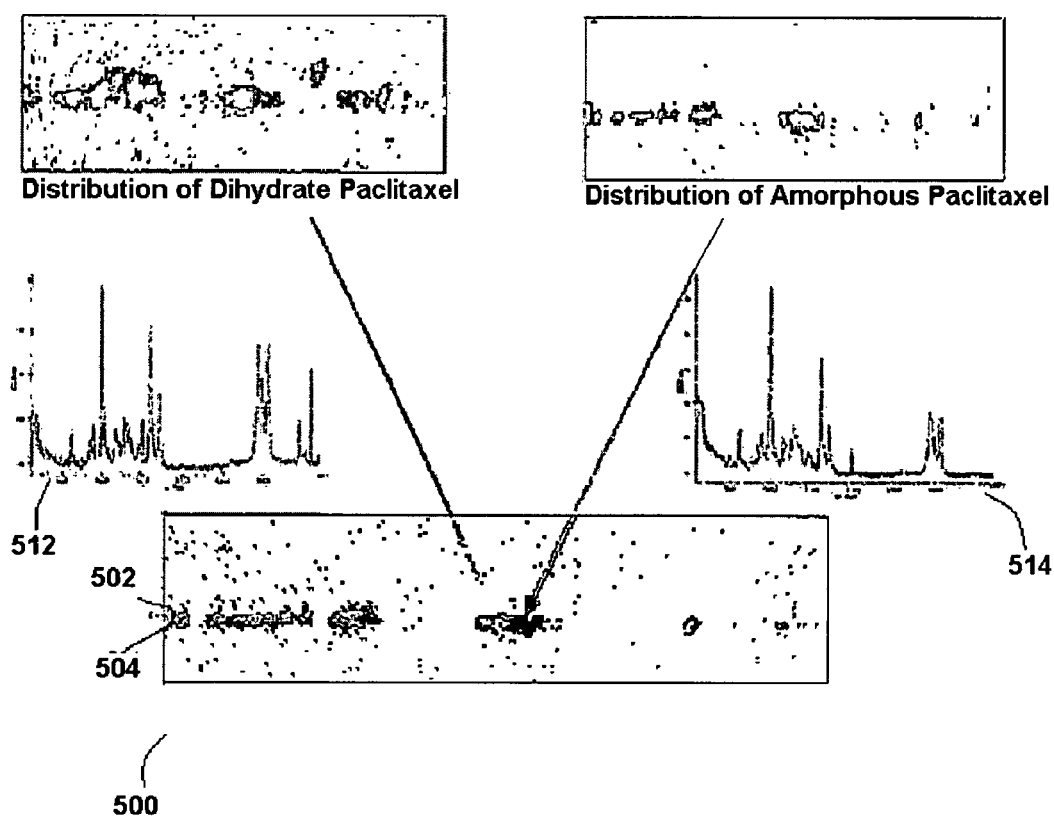
FIG. 4B shows the spatial distribution of two different solid forms of paclitaxel as a function of coating depth, obtained using confocal Raman spectroscopy.

Confocal Raman microscopy allows improved axial and lateral spatial resolution and fluorescence rejection over conventional Raman microscopy. Confocal Raman microscopy can be applied to reveal compositional or structural gradients as a function of depth within a sample. A depth profile of a coating can be obtained by confocal Raman microscopy by plotting the intensity of a component-specific vibrational band as a function of the distance from the sample surface. FIG. 4B shows a depth profile 500 of a coating comprising a mixture of dihydrate and amorphous solid forms of paclitaxel. The depth profile 500 was obtained by confocal Raman microscopy, by spatially detecting and plotting the intensity of scattered light matching a first spectrum 512 obtained from a dihydrate paclitaxel sample in a first color 502, followed by similarly detecting and plotting the intensity of scattered light matching a second spectrum 514 obtained from an amorphous paclitaxel sample. The depth profile 500 indicates that the dihydrate paclitaxel 502 is largely localized on the surface of the coating while the amorphous paclitaxel is predominantly distributed in a layer 504 below the dihydrate paclitaxel.

Figure 5A:
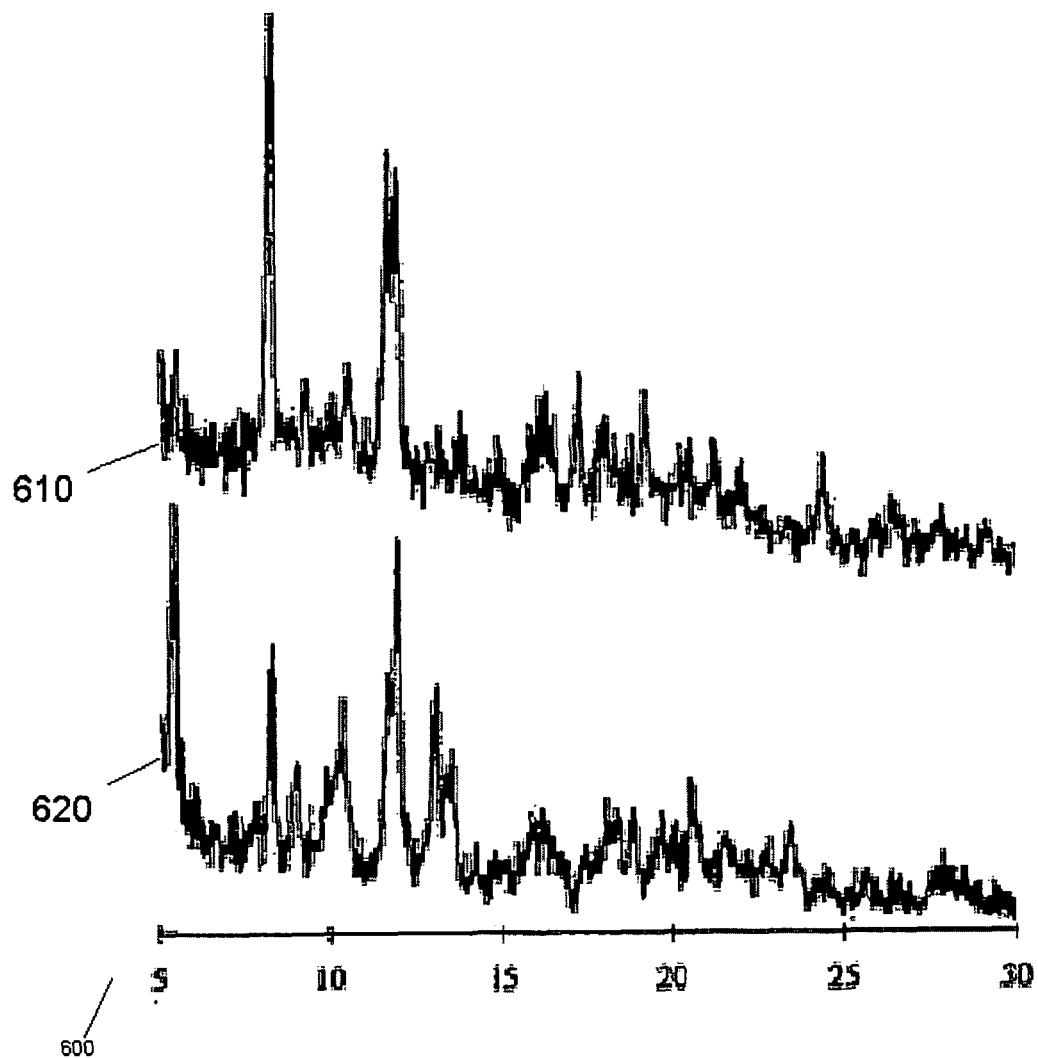
FIG. 5A shows a powder X-ray diffraction (XRPD) spectrum of two different solid forms of paclitaxel.

Powder X-ray Diffraction (XRPD) can also be used to differentiate various solid forms of taxane therapeutic agents. FIG. 5A shows the XRPD patterns 600 for amorphous 610 and dihydrate 620 solid forms of paclitaxel, with corresponding selected d-spacings of selected peaks provided in Table 2. Notably, the dihydrate paclitaxel can provide peaks different from the amorphous paclitaxel at 6.1, 9.5, 13.2 and 13.8° 2θ (obtained at 25° C.).

TABLE 2

XRPD Selected d-Spacings and Peak Intensities

| °2θ | d-spacing (Å) | Anhydrous | Dihydrate |
|---|---|---|---|
| 6.1 | 14.5 | | Strong* |
| 8.8 | 10.0 | Strong* | Strong* |
| 9.5 | 9.3 | | Medium** |
| 10.9 | 8.11 | | Medium** |
| 11.1 | 7.96 | Medium** | |
| 12.1 | 7.31 | Medium** | Strong* |
| 12.3 | 7.19 | Medium** | Strong* |
| 13.3 | 6.65 | | Medium** |
| 13.8 | 6.41 | | Medium** |
| 14.1 | 6.27 | Weak*** | |
| 19.3 | 4.59 | Weak*** | |
| 25.9 | 3.44 | Medium** | |

*= Strong Peak (relative intensity is more than 50);
**= Medium Peak (relative intensity between 20 and 50);
***= Weak Peak (relative intensity less than 20)

The data in FIG. 5A and Table 2 was obtained from R. T. Liggins et al., "Solid-State Characterization of Paclitaxel," *Journal of Pharmaceutical Sciences*, v. 86, No. 12, pp. 1458-1463 (December 1997), which is incorporated herein by reference. As described by Liggins et al., the anhydrous sample 610 can be obtained by drying paclitaxel (Hauser, Boulder, Colo.) at ambient temperature and reduced pressure (200 torr) in a vacuum oven (Precision Scientific, Chicago, Ill.). Liggins et al. report that the anhydrous sample 610 contained about 0.53% water, measured by Karl-Fischer analysis. The dihydrate sample 620 can be obtained by adding the anhydrous sample above to distilled water and stirring at ambient temperature for 24 hours, followed by filtration and collection of suspended solid paclitaxel and subsequent drying to constant weight. Liggins et al. report that the dihydrate sample 620 contained about 4.47% water (about 2.22 mol water/mol paclitaxel). Additional details relating to the spectra of FIG. 5A or the data in Table 2 are found in the Liggins et al. reference.

Figure 5B:
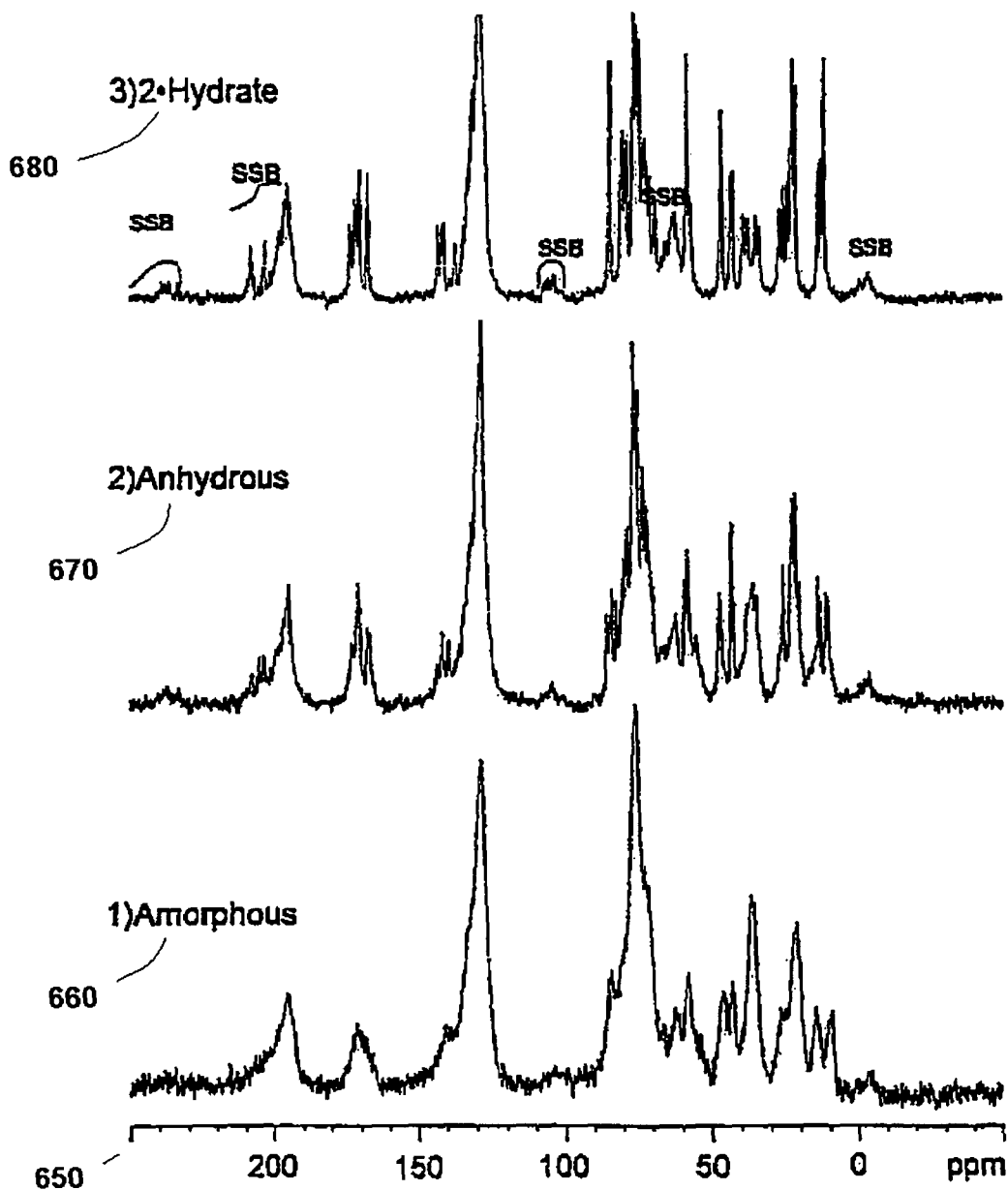
FIG. 5B shows a $^{13}C$ NMR spectrum of three different solid forms of paclitaxel.

$^{13}$C Nuclear Magnetic Resonance (NMR) can also be used to differentiate various solid forms of taxane therapeutic agents. FIG. 5B shows the $^{13}$C NMR spectra 650 for amorphous 660, anhydrous 670 and dihydrate 680 solid forms of paclitaxel. The data in FIG. 5B was obtained from Jeong Hoon Lee et al., "Preparation and Characterization of Solvent Induced Dihydrated, Anhydrous and Amorphous Paclitaxel," *Bull. Korean Chem. Soc.* v. 22, no. 8, pp. 925-928 (2001), incorporated herein by reference. As described by Lee et al., the spectra 650 in FIG. 5B can be obtained using a cross polarization/magic angle spinning (CP/MAS) $^{13}$C solid form NMR (Bruker DSX-300, Germany) experiment operating at 75.6 MHz. Standard pulse sequences and phase programs supplied by Bruker with the NMR spectrometer can be used to obtain the spectra 650. For each sample, about 250 mg sample can be spun at about 5 kHz in a 4 mm rotor, and cross polarization can be achieved with contact time of 1 ms. This process can be followed by data acquisition over 35 ms with high proton decoupling. A three-second relaxation delay can be used. The spectra 650 are referenced to adamantane, using glycine as a secondary reference (carbonyl signal of glycine was 176.04 ppm). Referring to FIG. 5B, the $^{13}$C solid form NMR spectrum of the dihydrate paclitaxel 680 shows greater sharpness and peak splitting than either of the other solid forms of paclitaxel, the spectrum of the anhydrous paclitaxel 670 shows greater sharpness and peak splitting than the spectrum from amorphous paclitaxel 660, and the spectrum from amorphous paclitaxel 660 shows less resolution and peak splitting than the spectrum from anhydrous paclitaxel 670.

The presence of different solid forms of the taxane therapeutic agent in a medical device coating can preferably be identified by contacting the coating with an elution medium that selectively dissolves one solid form more readily than a second solid form. In solution with an elution medium, such as porcine serum or blood, the presence of the taxane therapeutic agent can be identified, for example by using ultraviolet (UV) spectroscopy or high pressure liquid chromatography (HPLC).

The composition of a coating comprising a mixture of aPTX and dPTX can be determined by differential elution of each of the solid forms in series. One preferred method of determining the composition of a coating comprises a destructive testing method, whereby a medical device coated with a taxane therapeutic agent is placed in contact with a first elution media, such as porcine serum, that dissolves one solid form of the taxane therapeutic agent at a much faster rate than other solid forms of the taxane therapeutic agent. The presence of the taxane therapeutic agent can be determined by measuring the absorption of the first elution medium at 227 nm, as discussed with respect to FIG. 2. The strength of absorption of the taxane therapeutic agent in the first elution medium can be correlated to the amount of the first solid form of the taxane therapeutic agent in the original coating. Similarly, the amount of absorption in the second elution medium can be correlated to the amount of the second solid form of the taxane therapeutic agent in the original coating. In addition, two stents coated in the same manner can be independently contacted with the first medium or the second medium, and the amount of taxane therapeutic agent elution in each medium can be compared.

For example, porcine serum can be used as a first elution medium to determine the amount of aPTX in a coating. The rate constant for aPTX in porcine serum is about 100-times the rate constant for dPTX in porcine serum. Accordingly, when a medical device coated with a mixture of aPTX and dPTX is placed in a stream of flowing porcine serum, aPTX will elute more rapidly than dPTX, and the downstream absorption of paclitaxel in the elution stream can be correlated to the amount of aPTX in the original coating. Similarly, SDS can subsequently be used as a second elution medium, to rapidly elute the remaining dPTX from the medical device coating. Measuring the amount of paclitaxel in the SDS stream by absorption at 227 nm can be correlated to the amount of dPTX in the original coating.

Preferably, the coated medical device can be contacted with a modified porcine serum elution medium at a constant flow rate of 16 mL/min for a desired period of time (e.g., 6-24 hours) sufficient to elute the aPTX present on the stent. The percentage of the taxane therapeutic agent dissolved can be measured as a function of time by monitoring the optical density of the first elution medium at 227 nm after contacting the coated stent, as described above. The modified porcine serum elution medium can be prepared by adding 0.104 mL of a 6.0 g/L Heparin solution to porcine serum at 37° C. and adjusting the pH to 5.6+/−0.3 using a 20% v/v aqueous solution of acetic acid. The elution rate profile of the taxane therapeutic agent can be measured for any desired period, and correlated to the amount of aPTX in the coating. Subsequently, the coated medical device is contacted with a second elution medium comprising 0.3% sodium dodecyl sulfate (SDS) at 25° C. a constant flow rate of 16 mL/min for a suitable time period to elute the dPTX present in the coating.

The elution rate profile of the taxane therapeutic agent can be measured for any desired period, and correlated to the amount of aPTX in the coating.

Methods of Manufacturing Taxane Therapeutic Agent Coatings

A third embodiment provides methods of coating implantable medical devices ("medical devices") with the taxane therapeutic agents in one or more solid forms. Medical device coatings can comprise one or more of the solid forms of the taxane therapeutic agents described with respect to the first embodiment, formed by coating a taxane therapeutic agent spray coating solution in any suitable manner. For example, taxane therapeutic agents are preferably combined with a solvent to form a solution that can be applied to a surface of a medical device by spraying the solution onto the surface(s).

Taxane Therapeutic Agent Spray Coating Solutions

Spray coating methods are preferably used to deposit taxane therapeutic agents onto the surface(s) of a medical device in one or more different solid forms. The spray coating can be performed by any suitable coating technique, but typically includes the step of dissolving the taxane therapeutic agent in a suitable solvent and spraying the resulting solution onto the surface of the medical device. Changing the solvent(s) in the solution can change the solid forms of the resulting taxane therapeutic agent deposited on a medical device. To deposit a coating of a dihydrate taxane therapeutic agent, a recrystallized dihydrate taxane therapeutic agent from the first embodiment can be dissolved in a suitable organic alcohol solvent, such as methanol. To deposit a coating layer comprising a mixture of dihydrate and amorphous taxane solid forms, the taxane is preferably dissolved in a spray solvent comprising a mixture of water and a protic solvent such as methanol. Importantly, varying the ratio of water to methanol and/or the concentration of the taxane in the spray solvent comprising the taxane typically changes the composition of the resulting coating layer that is spray deposited. Generally, increasing the amount of methanol in the spray solution results in a coating layer with a higher proportion of amorphous taxane.

Importantly, the ratio of amorphous to dihydrate solid forms in a solid taxane solid coating may be changed by altering the methanol to water ratio and/or the concentration of the taxane therapeutic agent in the spray solution. Decreasing the concentration of the taxane in the spray solution may require a lower methanol to water ratio (i.e., less methanol and more water by volume) to obtain a given dihydrate to amorphous ratio in the solid coating formed after spraying and evaporation of the solvent. The spray solution can be made with any suitable concentration of the taxane therapeutic agent, although concentrations of about 0.5-5 mM are preferred, with concentrations of about 4.68 mM, 2.34 mM, 1.17 mM or 0.70 mM being particularly preferred. The relationship between the concentration of the taxane therapeutic agent in the spray solution, the ratio of methanol to water in the spray solution and the ratio of dihydrate to amorphous solid forms in the solid coating formed by spray coating the spray solution is illustrated with respect to paclitaxel in Tables 3a and 3b. Table 3a provides preferred spray solvent compositions for the spray deposition of a coating layer comprising a mixture of dihydrate paclitaxel and amorphous paclitaxel using a 4.68 mM paclitaxel concentration in the spray solution. Table 3a shows the ratio of methanol to water in a spray coating solution comprising about 2.4 mM paclitaxel, and the ratio of amorphous:dihydrate paclitaxel in a single coating layer deposited on a stent surface by spray coating the solutions with the specified compositions. Table 3b shows the ratio of methanol and water in a spray solution comprising either 2.4 mM paclitaxel and 0.7 mM paclitaxel.

TABLE 3a

Spray Coating Solvent Compositions for 4.68 mM Paclitaxel Solution

| dPTX:aPTX ratio | Solvent (% MeOH:$H_2O$) |
|---|---|
| >90%:<10% | 60:40%-90:10% |
| 60:40%-70:30% | 92:8%-93.5:6.5% |
| 40:60%-50:50% | 93.5:6.5%-94.55.5% |
| 30:70%-40:60% | 95:5%-97.5:2.5% |

TABLE 3b

Spray Coating Solvent Compositions at Lower Paclitaxel Concentrations

| dPTX:aPTX ratio | Solvent (% MeOH:$H_2O$) | [PTX] mM |
|---|---|---|
| 52:48% | 88:12% | 2.34 |
| 42:58% | 90:10% | |
| 25:75% | 93:7% | |
| 78:22% | 70:30% | 0.70 |
| 65:35% | 75:25% | |
| 55:45% | 80:20% | |

In addition to selecting an appropriate solvent system, other coating parameters such as the spraying apparatus, spray rate, and nozzle configuration can be selected to provide coatings comprising one or more solid forms of a taxane therapeutic agent. The coating of the medical device will now be described using three illustrative methods: spray gun coating, electrostatic deposition (ESD), and ultrasonic deposition (USD). However, the medical device may be coated using any suitable manner.

Pressure Spray Gun Coating

In a first aspect of the third embodiment, medical device coatings comprising a taxane therapeutic agent are applied to a surface of a medical device using a spray gun. Spray gun coating may be performed with a spray solution of paclitaxel in ethanol, without using methanol or water in the spray solution. The surface of the medical device can be bare, surface modified, or a primer coating previously applied to the medical device. Preferably, the coating applied to the surface consists essentially of the taxane therapeutic agent, and is substantially free of polymers or other materials. The taxane therapeutic agents described with respect to the first embodiment above can be dissolved in a solvent(s) and sprayed onto the medical device under a fume hood using a conventional spray gun, such as a spray gun manufactured by Badger (Model No. 200), or a 780 series spray dispense valve (EFD, East Providence, R.I.).

Alignment of the spray gun and stent may be achieved with the use of a laser beam, which may be used as a guide when passing the spray gun over the medical device(s) being coated. For spray gun coating, the therapeutic agent is preferably paclitaxel and the solvent is preferably ethanol. Desirably, a solution of about 0.5-5 mM paclitaxel in ethanol is used. More desirably, a solution of about 1-3 mM paclitaxel in ethanol is used. Even more desirably, a solution of about 2.4-4.7 mM paclitaxel in ethanol is used. Other therapeutic agents and solvents may also be used in the present invention. The distance between the spray nozzle and the nozzle size can be selected depending on parameters apparent to one of ordinary skill in the art, including the area being coated, the desired thickness of the coating and the rate of deposition. Any suitable distance and nozzle size can be selected. For example, for coating an 80 mm long stent, a distance of between about 1-7 inches between the nozzle and stent is preferred, depending on the size of the spray pattern desired. The nozzle diameter can be, for example, between about 0.014-inch to about 0.046-inch.

Varying parameters in the spray coating process can result in different solid forms of the taxane therapeutic agent in a deposited coating. Spray coating parameters such as solvent system, fluid pressure (i.e., tank pressure), atomization pressure, ambient temperature and humidity. The solvent is desirably volatile enough to be readily removed from the coating during or after the spray coating process, and is preferably selected from the solvents discussed with respect to the first embodiment for each solid form of a taxane therapeutic agent.

Typically, spray coating in lower humidity, higher atomization pressure and/or lower temperature (e.g., room temperature) conditions, favor the formation of the amorphous solid form of the taxane therapeutic agent. Methods of coating amorphous taxane therapeutic agents using a 780S-SS spray dispense valve (EFD, East Providence, R.I.) can comprise the steps of: dissolving solid paclitaxel in ethanol to form a spray solution of a desired concentration (e.g. 4.68 mM), and spraying the solution onto a medical device with an atomization pressure of about 5-10 psi in an environment having a relative humidity of 30% or lower. Preferably, the spraying step is performed at a temperature of between about 65° F. and 75° F., and with a fluid pressure of between about 1.00 and 5.00 psi. For example, amorphous paclitaxel (aPTX) coatings have been deposited using the EFD 780S-SS spray valve (EFD, East Providence, R.I.) under the following conditions: (1) 4.0 g/L PTX (4.68 mM) in ethanol spray solution, 20% relative humidity, 13.00 psi atomization pressure, 2.00 psi fluid (tank) pressure and 80° F. ambient temperature; and (2) 4.0 g/L PTX in ethanol spray solution, 30% relative humidity, 25.00 psi atomization pressure, 1.50 psi fluid (tank) pressure and 75° F. ambient temperature. An amorphous taxane therapeutic agent coating has a clear or transparent appearance.

Spray coating in higher humidity, lower atomization pressure and/or higher temperature conditions, favor the formation of the dihydrate solid form of the taxane therapeutic agent. Methods of coating dihydrate taxane therapeutic agents are provided which comprise the steps of: dissolving solid paclitaxel in ethanol to form a solution, and spraying the solution onto a medical device. When spray coating with the EFD 780S-SS spray valve (EFD, East Providence, R.I.), the spraying step is preferably performed at a temperature of 75° F. or greater, and with a fluid pressure of between about 1.00 and 5.00 psi. For example, dihydrate paclitaxel (dPTX) coatings have been deposited using an EFD 780S-SS spray valve (EFD, East Providence, R.I.) under the following conditions: (1) 4.0 g/L PTX in ethanol spray solution, 44% relative humidity, 12.00 psi atomization pressure, 2.50 psi fluid (tank) pressure and 80° F. ambient temperature; or (2) 4.0 g/L PTX in ethanol spray solution, 55% relative humidity, 5.00 psi atomization pressure, 1.00 psi fluid (tank) pressure and 70° F. ambient temperature.

Electrostatic Spray Coating

In a second aspect of the third embodiment, the taxane therapeutic agent is dissolved in a suitable solvent or combination of solvents and then sprayed onto the medical device using an electrostatic spray deposition (ESD) process. The ESD process generally operates on the principle that a charged particle is attracted towards a grounded target. One typical ESD process may be described as follows. The solution that is to be spray coated is typically charged to several thousand volts (typically negative) and the medical device surface held at ground potential. The charge of the spray solution is generally great enough to cause the solution to jump across an air gap of several inches before landing on the surface. As the spray solution is in transit towards the surface, the spray fans out in a conical pattern, promoting formation of a more uniform coating. In addition to the conical spray shape, electrons are further attracted towards the conducting portions of the surface, rather than towards the non-conductive base the medical device surface is mounted on, leaving the coating mainly on the surface only.

During the ESD spray coating process, the spray solution is forced through a capillary subjected to an electrical field. The spray solution leaves the capillary in the form of a fine spray, the shape of which is determined by the electrical field. The medical device is then coated by placing it in the spray and allowing the solvent to evaporate, leaving the desired coating on the surface of the device.

The ESD method allows for control of the coating composition and surface morphology of the deposited coating. In particular, the morphology of the deposited coating may be controlled by appropriate selection of the ESD parameters, as set forth in WO 03/006180 (Electrostatic Spray Deposition (ESD) of biocompatible coatings on Metallic Substrates), the contents of which are incorporated by reference. For example, a coating having a uniform thickness and grain size, as well as a smooth surface, may be obtained by controlling deposition conditions such as deposition temperature, spraying rate, precursor solution, and bias voltage between the spray nozzle and the medical device being coated. The ESD spray solution preferably includes methanol. It is believed that the addition of methanol increases the polarity of the solvent solution, thereby providing a fine spray that is ideal for use in an electrostatic coating process. For example, the spray solution can comprise about 50-80% methanol (by volume), more desirably about 65-75% methanol and most preferably up to about 70% methanol.

Ultrasonic Spray Coating

In a third and most preferred aspect of the third embodiment, the taxane therapeutic agent is spray coated onto a medical device surface using an ultrasonic spray deposition (USD) process. Ultrasonic nozzles employ high frequency sound waves generated by piezoelectric transducers which convert electrical energy into mechanical energy. The transducers receive a high frequency electrical input and convert this into vibratory motion at the same frequency. This motion is amplified to increase the vibration amplitude at an atomizing surface.

Ultrasonic nozzles are typically configured such that excitation of a piezoelectric crystals creates a longitudinal standing wave along the length of the nozzle. The ultrasonic energy originating from the transducers may undergo a step transition and amplification as the standing wave traverses the length of the nozzle. The nozzle is typically designed such that a nodal plane is located between the transducers. For ultrasonic energy to be effective for atomization, the nozzle tip must be located at an anti-node, where the vibration amplitude is greatest. To accomplish this, the nozzle's length should be a multiple of a half-wavelength. In general, high frequency nozzles are smaller, create smaller drops, and consequently have smaller maximum flow capacity than nozzles that operate at lower frequencies.

Liquid introduced onto the atomizing surface absorbs some of the vibrational energy, setting up wave motion in the liquid on the surface. For the liquid to atomize, the vibrational amplitude of the atomizing surface should be adequately controlled. Below a certain amplitude, the energy may be insufficient to produce atomized drops. If the amplitude is excessively high, cavitation may occur. The input power is preferably selected to provide an amplitude producing a desired spray having a fine, low velocity mist. Since the atomization mechanism relies largely on liquid being introduced onto the atomizing surface, the rate at which liquid is atomized depends on the rate at which it is delivered to the surface.

For example, the medical device may be coated using an ultrasonic spray nozzle, such as those available from Sono-Tek Corp., Milton, N.Y. The spray solution can be loaded into a syringe, which is mounted onto a syringe pump and connected to a tube that carries the solution to the ultrasonic nozzle. The syringe pump may then used to purge the air from the solution line and prime the line and spay nozzle with the solution. The stent may be loaded onto a stainless steel mandrel in the ultrasonic coating chamber. The stent may optionally be retained around a mandrel during coating. Alternatively, the stent may be secured and rotated on a clip or in within a steam of rapidly flowing gas such as nitrogen. Preferably, contact between the stent and the mandrel is minimized so as to prevent a "webbed" coating between struts. Typically, the luminal surface is not coated although the coating may be applied to any surface, if desired.

The medical device may be a vascular stent mounted around a mandrel. The mandrel may be fastened onto a motor, positioned below the ultrasonic nozzle. The motor rotates the mandrel at a pre-set speed and translationally moves the stent underneath the ultrasonic spray. In one aspect, the rotational speed is set to 10 rpm and the translational speed is set to 0.01 mm per second. In another aspect, the rotational speed is set to 60 rpm and the translational speed is set to 0.05 mm per second. In yet another embodiment, the rotational speed is set to 30-150, preferably about 110 rpm, and the translational speed is set to 0.19 mm per second. Other speeds and combinations may also be used in the present invention. Preferred coating parameters for USD using a Sono-tek Model 06-04372 ultrasonic nozzle are provided in Table 4 below:

TABLE 4

Ultrasonic Spray Deposition Parameters for Sono-tek Model 06-04372

| Flow rate (mL/min) | Coating velocity (in/sec) | Rotation Speed (rpm) | Nozzle Power (watts) | Process Gas (psi) | Distance (mm) |
|---|---|---|---|---|---|
| 0.01-2 | 0.01-0.5 | 30-150 | 0.9-1.2 | 0.1-2.5 | 1-25 |

Importantly, ultrasonic spray coating is preferably performed at an ambient temperature of about 85-87° F. and in a coating chamber at a pressure of less than about 0.05 psi. The temperature is preferably selected to provide a desirably uniform, solvent-free coating. Preferably, the coating is performed at a temperature of about 60-90° F., preferably about 85-87° F. The quality of the coating may be compromised if coating is performed outside the preferred temperature range. The temperature during ultrasonic spray coating should be high enough to rapidly evaporate the methanol in the spray solution before contacting the stent (i.e., at least about 80 F).

Most preferably, the ultrasonic spray coating is performed at a flow rate of about 0.03 mL/min, a coating velocity of about 0.025 in/sec, a rotation speed of about 60 rpm, a nozzle power of about 1 watt, a process gas pressure of about 2 psi, a distance of about 12 mm between the nozzle and medical device, and a temperature of about 85° F. within a coating chamber. The coating chamber is purged with nitrogen to displace oxygen in the system. During the process, the stent is kept at ambient temperature and in a closed chamber.

Taxane coatings desirably comprise at least one layer comprising a durable amorphous solid form. Preferably, coatings comprising a mixture of amorphous and dihydrate taxane solid forms preferably include a minimum amount of amorphous taxane to impart a desired level of durability to the coating. Typically, coatings with at least about 25-30% dihydrate taxane (i.e., dPTX:aPTX ratio including about 70-75% dPTX) have a desired level of durability to withstand a stent crimping procedure. Preferred spray solution compositions are selected to provide a coating having a taxane therapeutic agent with a dihydrate:amorphous solid form ratio with desired properties of elution rate, surface uniformity and durability. For example, preferred solvent systems for ultrasonic spray coating include a dihydrate:amorphous paclitaxel coating (e.g., from a SonoTek 06-04372 ultrasonic nozzle) with 60-70% w dihydrate (remainder amorphous) paclitaxel, and may be prepared by selecting paclitaxel, methanol and water concentrations according to Tables 3a-3b while spray coating at about 84-87 F within the parameters specified in Table 4 above. The coatings can also be applied (in total or in part) by a coating method described with respect to the third embodiment, or any other suitable manner. For example, the coating may also be deposited onto the medical device by spraying, dipping, pouring, pumping, brushing, wiping, vacuum deposition, vapor deposition, plasma deposition, electrostatic deposition, epitaxial growth, or any other method known to those skilled in the art. Preferably, however, the medical device coatings are applied by spraying methods, such as those described with respect to the third embodiment above.

Modification of Medical Device Surface to Promote Adhesion of Coating

Optionally, prior to spray coating of the taxane therapeutic agent, the surface of the medical device can be prepared to promote adhesion of the coating material before depositing the coating. Useful methods of surface preparation can include, but are not limited to cleaning; physical modifications such as etching, drilling, cutting, or abrasion; and chemical modifications such as solvent treatment, the application of primer coatings, the application of surfactants, plasma treatment, ion bombardment, covalent bonding and electrochemical methods such as electropolishing, striking, electroplating and electrochemical deposition. Such surface preparation may serve to activate the surface and promote the deposition or adhesion of the coating on the surface. Surface preparation can also selectively alter the release rate of the taxane therapeutic agent. Any additional coating layers can similarly be processed to promote the deposition or adhesion of another layer, to further control the release of the taxane therapeutic agent, or to otherwise improve the biocompatibility of the surface of the layers. For example, plasma treating an additional coating layer before depositing a taxane therapeutic agent thereon may improve the adhesion of the taxane therapeutic agent, increase the amount of taxane therapeutic agent that can be deposited, and allow the taxane therapeutic agent to be deposited in a more uniform layer.

Sterilization of Medical Devices

The medical devices of the present invention can be sterilized prior to implantation into the body, including before and/or after coating. Preferably, the coated medical device is sterilized using a conventional chemical vapor sterilization process that does not undesirably degrade or alter the taxane therapeutic coating. For example, a conventional ethylene oxide (ETO) sterilization process may be used, which may involve exposing the coated medical device to ETO gas at a temperature of about 120 F for a period of about 1-3 hours. Since ethylene oxide gas readily diffuses through many common packaging materials and is effective in killing microorganisms at temperatures well below those required for heat sterilization techniques, ETO sterilization can permit efficient sterilization of many items, particularly those made of thermoplastic materials, which cannot withstand heat sterilization. The process generally involves placing an item in a chamber and subjecting it to ethylene oxide vapor. When used properly, ethylene oxide is not only lethal to microorganisms, but it is also non-corrosive, readily removed by aeration.

Notably, the ratio of dihydrate to amorphous solid forms of the taxane therapeutic agent may increase during ETO sterilization. For example, increases of up to about 5% in the proportion of dihydrate paclitaxel were observed in coatings consisting of paclitaxel in both the dihydrate and amorphous solid forms prior to sterilization. Typically, coated medical devices can be sterilized within suitable packaging, such as a bag, pouch, tube or mold.

Alternatively, the medical device may be loaded into final packaging, and gamma irradiated in a gamma chamber. In one embodiment, the implantable medical device is irradiated with between 1 and 100 kGy. In another embodiment, the implantable medical device is irradiated with between 5 and 50 kGy, and in yet another embodiment, the implantable medical device is irradiated with between 25 and 28 kGy.

Therapeutic Agent Elution Profile

Local administration of therapeutic agents may be more effective when carried out over an extended period of time, such as a time period at least matching the normal reaction time of the body to an angioplasty procedure, for example. At the same time, it may be desirable to provide an initial high dose of the therapeutic agent over an initial period. For example, local administration of a therapeutic agent over a period of days or even months may be most effective in treating or inhibiting conditions such as restenosis. The coating may be configured to provide a delayed release of the taxane therapeutic agent when the medical device is implanted, permitting the coatings to be configured to provide for the coated taxane therapeutic agent(s) to be released for desirable periods of time. For example, a coating consisting essentially of the taxane therapeutic agent in one or more solid forms can be configured to release less than 90 percent of the coated taxane therapeutic agent into an aqueous environment (such as blood or porcine serum) over a period of at least about 6 months, two months, one month, one week, or one day. In particular, a coating can have an outer layer of more than 50% rapidly-dissolving amorphous paclitaxel over a layer of more than 50% slow-dissolving dihydrate paclitaxel.

The release characteristics of a coated taxane therapeutic agent can be described by an elution profile. The elution profile of a medical device comprising a taxane therapeutic agent shows the percentage of the taxane therapeutic agent that dissolves as a function of time in a given elution medium. The rate of dissolution of the taxane therapeutic agent can vary based on the elution medium being used and the solid form of the taxane therapeutic agent before dissolution. An elution profile can be obtained by any suitable method that allows for measurement of the release of the taxane therapeutic agent from the coating in a manner that can be measured with a desired level of accuracy and precision. In one embodiment, the elution profile of the release of a taxane therapeutic agent is obtained by contacting the medical device with a suitable elution medium. The elution medium can be formulated to simulate conditions present at a particular point of treatment within a body vessel. For example, an elution medium comprising porcine serum can be used to simulate implantation within a blood vessel. The release of taxane therapeutic agent from the medical device can be measured by any suitable spectrographic method, such as measurement of a UV absorption spectrum of the test fluid after contacting the medical device. Typically, the intensity of absorption at characteristic UV absorption peak, such as about 227 nm, can be correlated to the presence and amount of a taxane therapeutic agent in a sample. The amount of taxane therapeutic agent on the medical device can be determined by contacting the medical device with a suitable elution medium and detecting the amount of taxane therapeutic agent released from the medical device into the elution medium.

An elution medium can be selected to solubilize one solid form of a taxane therapeutic agent more rapidly than other solid forms of the taxane therapeutic agent, while allowing for subsequent measurement of the solubilized taxane therapeutic agent in a manner that can be correlated to the amount of the more soluble solid form of the taxane therapeutic agent released from the medical device. Subsequently, a second elution medium can be selected to quickly solubilize one or more other solid forms of the taxane therapeutic agent that did not dissolve in the first elution medium. Preferably, substantially all the taxane therapeutic agent of at least one solid form is removed from the medical device after contact with an elution medium for a desired period of time. The taxane therapeutic agent is subsequently detected in the elution medium. The detection of the taxane therapeutic agent is correlated to the amount of a particular solid form of the taxane therapeutic agent that was present on the medical device surface prior to contacting the medical device with the elution medium.

In one embodiment, the elution profile of a paclitaxel coating on a medical device is determined by first contacting the medical device with a first elution medium that readily dissolves the amorphous paclitaxel at least about 10-times more rapidly than the dihydrate paclitaxel, and then subsequently detecting the amount of taxane therapeutic agent within the elution medium. The medical device is exposed to the first elution medium and the rate of release of the taxane therapeutic agent from the medical device is determined by detecting the taxane therapeutic agent in the first elution medium for a first desired period of time. After the first desired period of time, the amount of taxane therapeutic agent remaining on the medical device can be determined by contacting the medical device with a second elution medium that readily dissolves the dihydrate paclitaxel, and subsequently detecting the amount of taxane therapeutic agent leaving the medical device in the second elution medium.

Any suitable analytical technique(s) may be used to detect a taxane therapeutic agent in an elution medium. Suitable detection methods, such as a spectrographic technique, permit measurement of a property of the elution medium that can be correlated to the presence or concentration of the taxane therapeutic agent with a desired level of accuracy and precision. In one embodiment, absorption spectroscopy (e.g., UV) can be used to detect the presence of a taxane therapeutic agent, such as in an elution medium. Accordingly, the Beer-Lambert Correlation may be used to determine the concentration of a taxane therapeutic agent in a solution. This correlation is readily apparent to one of ordinary skill in the art, and involves determining the linear relationship between absorbance and concentration of an absorbing species (the taxane therapeutic agent in the elution medium). Using a set of standard samples with known concentrations, the correlation can be used to measure the absorbance of the sample. A plot of concentration versus absorbance can then be used to determine the concentration of an unknown solution from its absorbance. UV absorbance of the taxane therapeutic agent at 227 nm can be measured (see FIG. 2), and the absorbance at this wave length can be correlated to concentration of the taxane in the test solution.

Figure 6A:
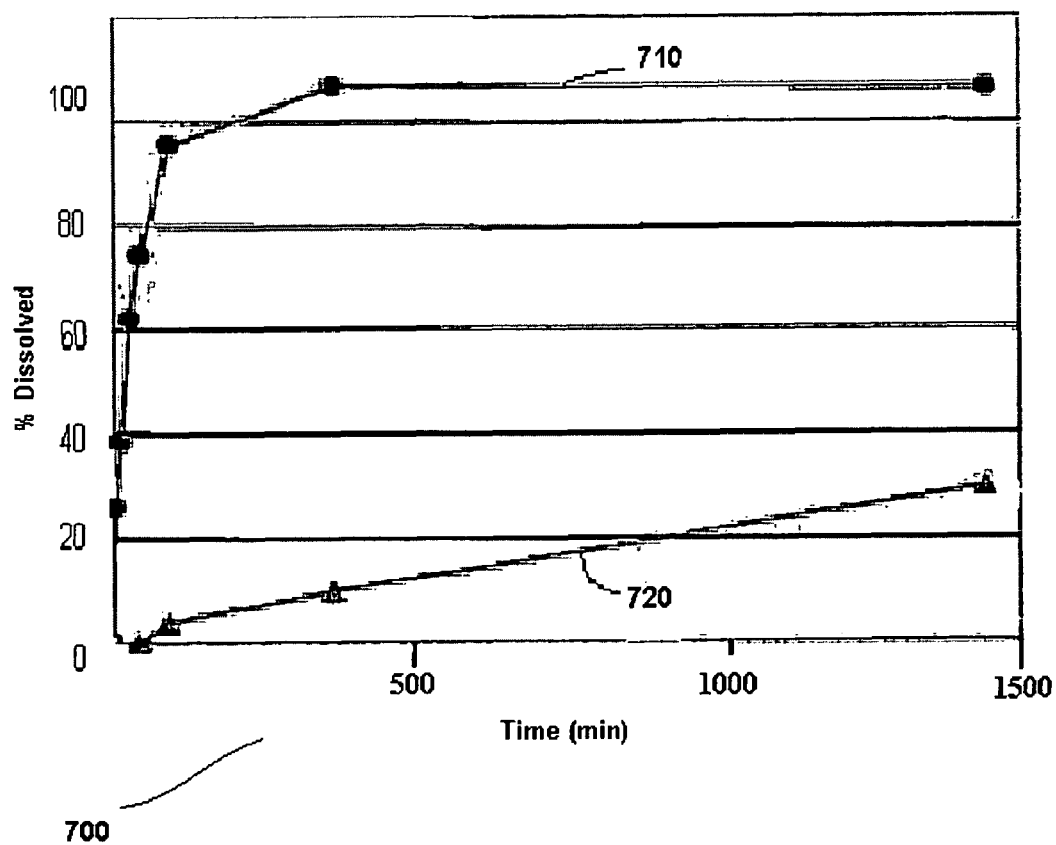
FIG. 6A shows elution profiles for two different coatings of amorphous paclitaxel and solvated paclitaxel eluting in porcine serum.

FIG. 6A shows elution profiles 700 for two medical devices in porcine serum elution media at 25° C. The first elution profile 710 was obtained from a first coated vascular stent coated with a single layer of amorphous paclitaxel. The second elution profile 720 was obtained from a second coated vascular stent coated with a single layer of dihydrate paclitaxel. The amorphous paclitaxel coating on the first vascular stent had a clear, transparent visual appearance, while the dihydrate paclitaxel coating on the second vascular stent had an opaque, white and cloudy visual appearance. Referring to the first elution profile 710, obtained from the amorphous paclitaxel coating, 100% of the amorphous paclitaxel dissolved within about 6.5 hours (400 minutes), while less than 40% of the second (dihydrate) coating eluted under the same conditions after about 24 hours.

A preferred first elution medium is an aqueous solution comprising 0.1% to about 10% of a cyclodextrin. In one aspect, an elution profile may be obtained by contacting a coated medical device comprising a taxane therapeutic agent with an elution medium comprising a cyclodextrin. A cyclodextrin is a cyclic oligosaccharide formed from covalently-linked glucopyranose rings defining an internal cavity. The diameter of the internal axial cavity of cyclodextrins increases with the number of glucopyranose units in the ring. The size of the glucopyranose ring can be selected to provide an axial cavity selected to match the molecular dimensions of a taxane therapeutic agent. The cyclodextrin is preferably a modified β-cyclodextrin, such as Heptakis-(2,6-di-O-methyl)-β-cyclodextrin (HCD). Suitable cyclodedtrin molecules include other β-cyclodextrin molecules, as well as γ-cyclodextrin structures.

The elution medium comprising a cyclodextrin can dissolve a taxane therapeutic agent so as to elute the taxane therapeutic agent from a medical device coating over a desired time interval, typically about 24 hours or less (less than comparable elution times in porcine serum). Preferably, the cyclodextrin elution medium is formulated to provide distinguishable elution rates for different coating configurations, providing different elution profiles for different solid forms of a taxane therapeutic agent in the coating, or different types or amounts of polymers incorporated with the taxane therapeutic agent within a coating. The elution medium may be contacted with a medical device comprising a taxane therapeutic agent, such as paclitaxel, in any manner providing an elution profile indicative of the arrangement of the taxane therapeutic agent molecules in the coating. For example, the elution medium may contact a medical device coating in a continuous flow configuration, or in a batch testing configuration.

Figure 6B:
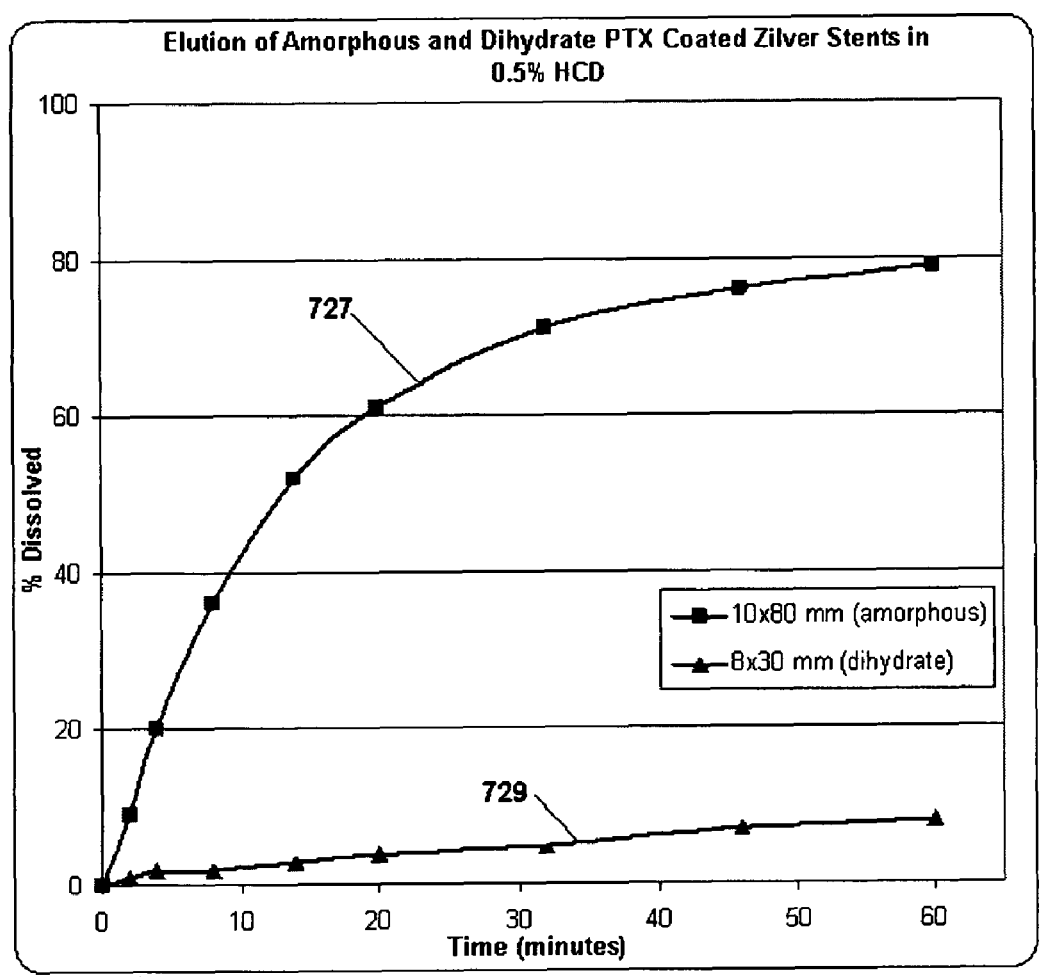
FIG. 6B shows elution profiles for two different coatings each comprising different amounts of the amorphous and dihydrate solid forms of paclitaxel eluting in porcine serum.

Taxane therapeutic agents typically have different elution profiles in different elution media. FIG. 6B shows elution profiles 725 for the first and second vascular stents in a 0.5% w/v aqueous solution of Heptakis-(2,6-di-O-methyl)-β-cyclodextrin (HCD) elution medium at 25° C. The first elution profile 727 was obtained from the first coated vascular stent coated with a single layer of amorphous paclitaxel. The second elution profile 729 was obtained from the second coated vascular stent coated with a single layer of dihydrate paclitaxel. Referring to the first elution profile 727, obtained from the amorphous paclitaxel coating, about 80% of the amorphous paclitaxel dissolved within about 1 hour, while less than 20% of the dihydrate paclitaxel was released within 1 hour in the second elution profile 729. Accordingly, comparing FIGS. 6A and 6B, both the HCD and porcine serum elution media selectively dissolved the amorphous paclitaxel distinguishably more rapidly than the dihydrate paclitaxel, however the HCD elution medium dissolved the amorphous paclitaxel much more quickly (727) than the porcine serum (710).

Figure 6C:
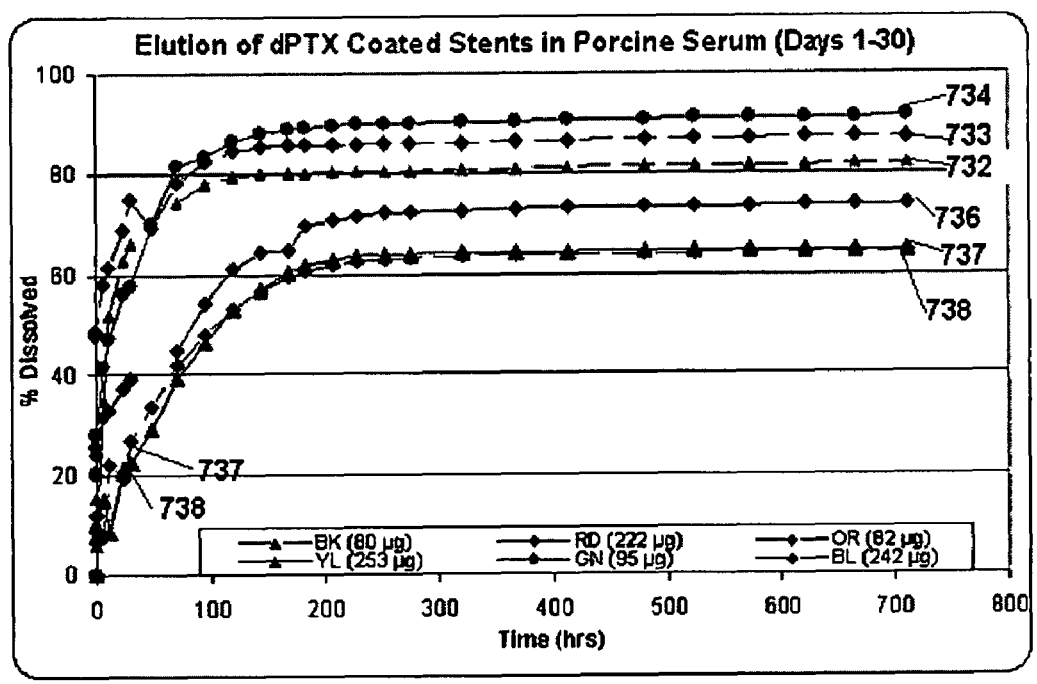
FIG. 6C shows elution profiles for several different coatings having different amounts of the amorphous paclitaxel and dihydrate solid forms of paclitaxel eluting in an aqueous solution comprising Heptakis-(2,6-di-O-methyl)-β-cyclodextrin (HCD).

FIG. 6C shows elution profiles 730 for six medical devices in porcine serum elution media at 25° C. for 30 days. All six medical devices were coated with a single layer of paclitaxel in various solid forms, without a polymer or any release-rate-modifying substance. A first elution profile 732, a second elution profile 733 and a third elution profile 734 were obtained coated vascular stents coated with a single layer of about 1 μg/mm² (±15%) paclitaxel layer with about 70% of the paclitaxel in the less soluble dihydrate solid form and about 30% of the paclitaxel in the more soluble amorphous solid form. Notably, increasing the total amount of paclitaxel in the single-layer coating from 80 μg in the first elution profile 732 to 82 μg in the second elution profile 733 to 95 μg in the third elution profile 734 resulted in a steady increase in the elution rate. A third elution profile 736, a fifth elution profile 737 and a sixth elution profile 738 were obtained coated vascular stents coated with a single layer of about 3 μg/mm² (±15%) paclitaxel layer with about 80% of the paclitaxel in the dihydrate solid form and about 20% of the paclitaxel in the amorphous solid form. Again, increasing the total amount of paclitaxel in the single-layer coating from 222 μg in the fourth elution profile 736 to 242 μg in the sixth elution profile 738 to 253 μg in the fifth elution profile 737 resulted in a steady increase in the elution rate. The rate of elution from the 3 μg/mm² paclitaxel coatings was slower than the rate of elution from the 1 μg/mm² coatings because the amount of the paclitaxel in the less soluble dihydrate solid form was increased from 70% in the 31 g/mm² paclitaxel coatings to 80% in the 1 μg/mm² paclitaxel coatings. Accordingly, the rate of release of a paclitaxel coating can be varied by changing the amount of each solid form of the paclitaxel present in a coating. Thus, by varying the solid form of a taxane therapeutic agent, a lower dose of paclitaxel can be used to provide a more sustained release than a higher dose of paclitaxel, without introducing a polymer to the coating.

Figure 7A:
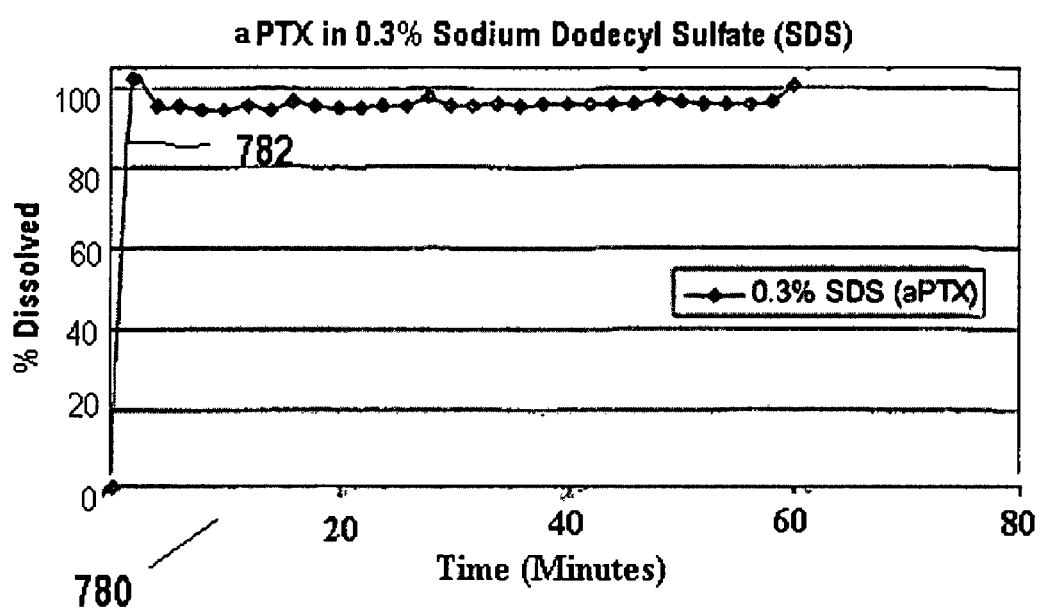
FIG. 7A shows an elution profile for a coating of the amorphous solid form of paclitaxel eluting in sodium dodecyl sulfate (SDS).
Figure 7B:
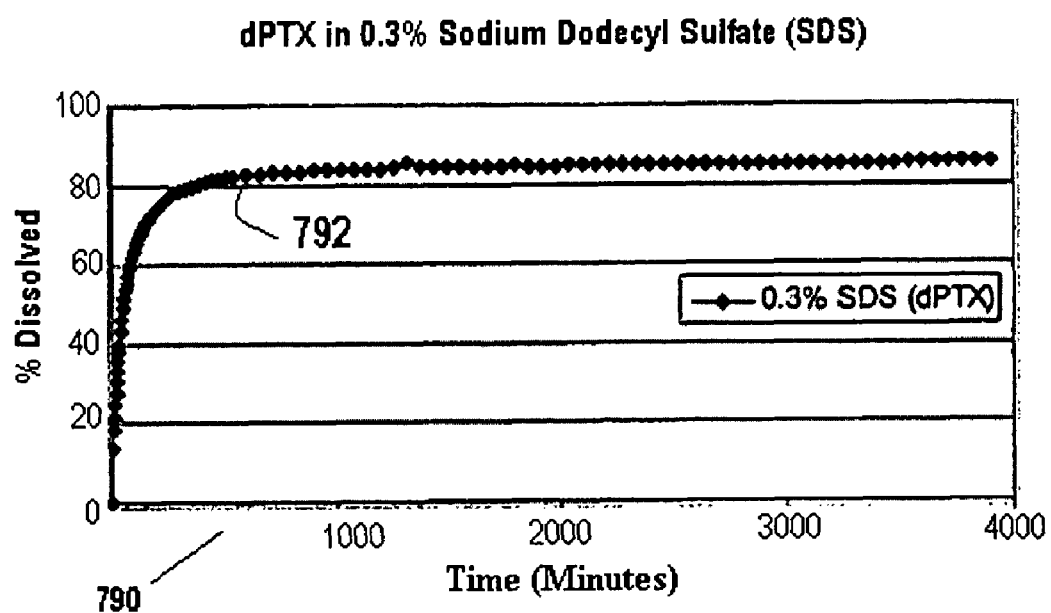
FIG. 7B shows the elution profile for a coating of the dihydrate solid form of paclitaxel eluting in sodium dodecyl sulfate (SDS).

Another suitable elution medium for taxane therapeutic agent is sodium dodecyl sulfate (SDS). FIG. 7A shows the solubility of amorphous paclitaxel in sodium dodecyl sulfate (SDS). FIG. 7A is a graph 780 showing a first elution profile 782 obtained from a first coated vascular stent coated with a single layer of amorphous paclitaxel (aPTX) in 0.3% SDS elution medium at 25° C. FIG. 7B shows the solubility of dihydrate paclitaxel in sodium dodecyl sulfate (SDS). FIG. 7B is a graph 790 showing a second elution profile 792 obtained from a second coated vascular stent coated with a single layer of dihydrate paclitaxel (dPTX) in the same 0.3% SDS elution medium at 25° C. The rate of elution of amorphous paclitaxel in the first elution profile 782 is more rapid than the rate of elution of the dihydrate paclitaxel in the second elution profile 792. However, both solid forms of paclitaxel are significantly more soluble in the 0.3% SDS elution medium than in the porcine serum elution media (e.g., compare FIG. 6A and FIGS. 7A-7B).

Figure 8A:
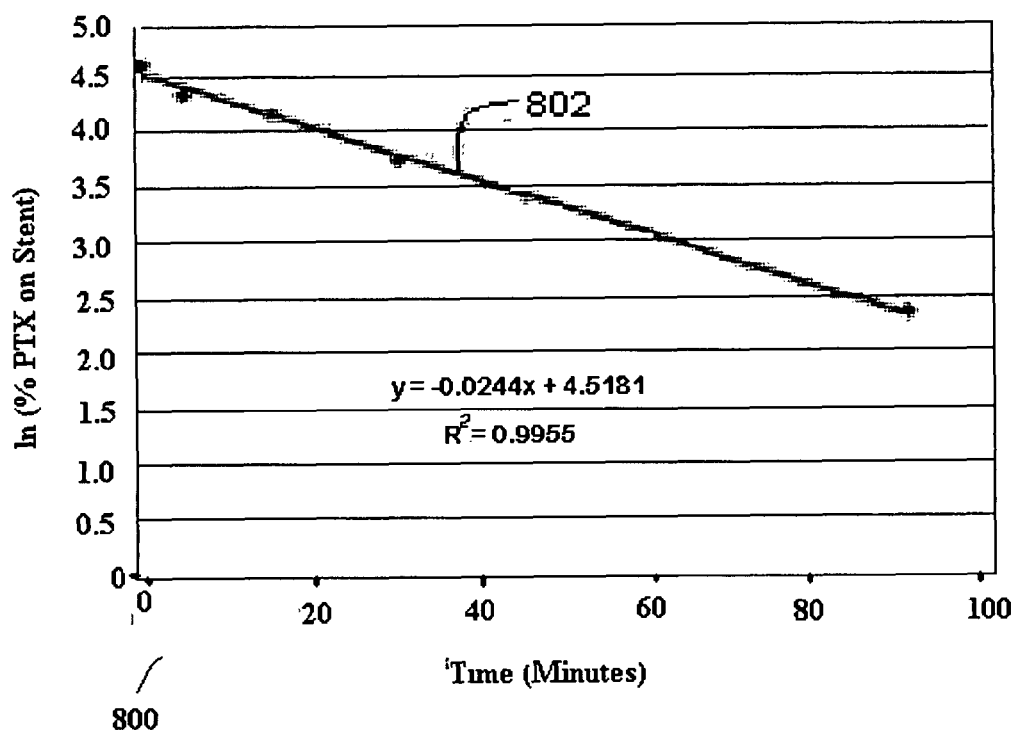
FIG. 8A is a kinetic plot for the dissolution of amorphous paclitaxel in porcine serum.

FIG. 8A shows a first-order kinetic plot 800 of the data from the first elution profile 710 in FIG. 6A. The first kinetic plot 800 plots the natural log of the percent of the amorphous paclitaxel (710) coating remaining on the first vascular stent as a function of time (minutes) from data obtained for FIG. 6A. The data in the first kinetic plot 800 closely fits to straight line 802 ($R^2$=0.9955), indicating that the elution of amorphous paclitaxel in porcine serum at 25° C. follows first order kinetics. Based on the slope of the line 802, the first order rate constant of amorphous paclitaxel in porcine serum (25° C.) is about 0.0244 $min^{-1}$, with a half life of about 30 minutes.

Figure 8B:
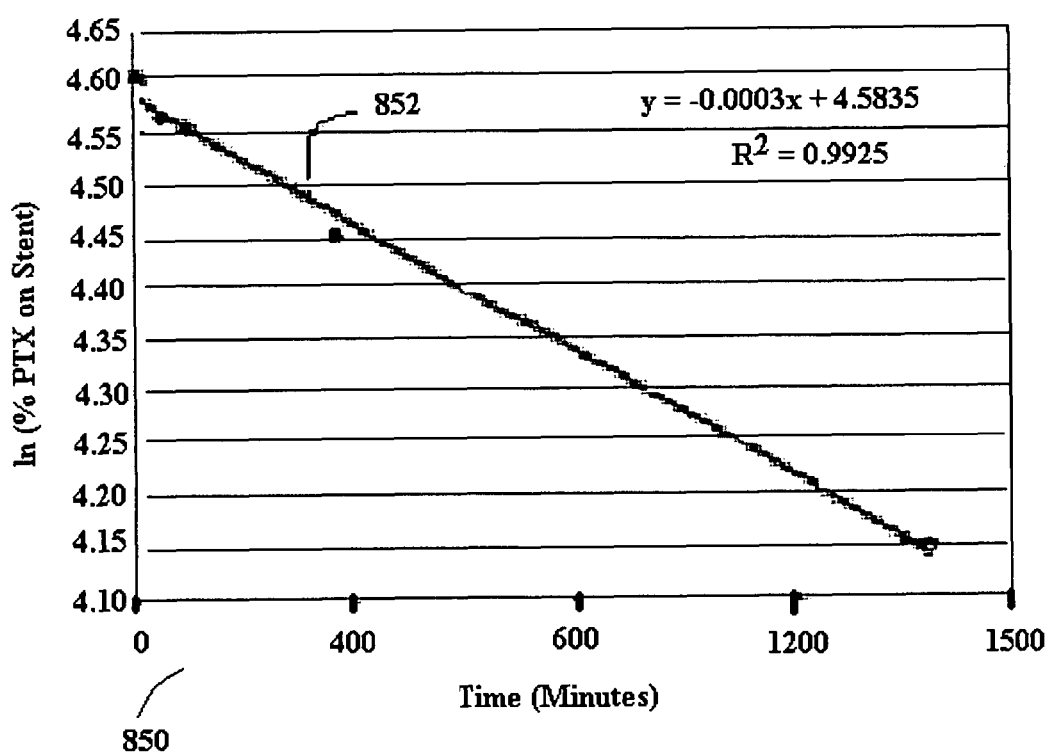
FIG. 8B is a kinetic plot for the dissolution of dihydrate paclitaxel in porcine serum.

Similarly, FIG. 8B shows a first-order kinetic plot 850 of the data from the second elution profile 720 in FIG. 6A. The kinetic plot 850 indicates the natural log of the percent of the dihydrate paclitaxel (720) coating remaining on the second vascular stent as a function of time (minutes). The data in the first kinetic plot 850 also closely fits to straight line 852 ($R^2$=0.9925), indicating that the elution of dihydrate paclitaxel in porcine serum at 25° C. also follows first order kinetics. Based on the slope of the line 852, the first order rate constant of dihydrate paclitaxel in porcine serum (25° C.) is about 0.0003 $min^{-1}$, with a half life of about 38.5 hours (2,310 minutes). Therefore, the rate of elution of the amorphous paclitaxel is about 100-times faster than dihydrate paclitaxel in porcine serum (25° C.).

Figure 9:
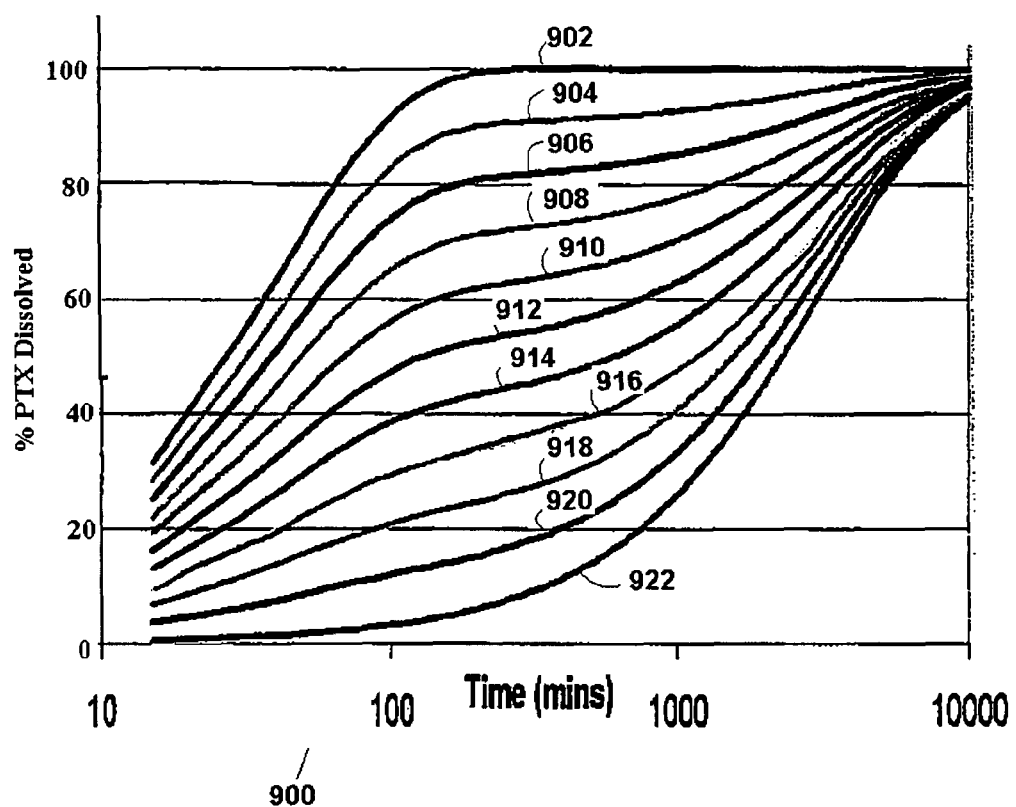
FIG. 9 is a graph of calculated (predicted) porcine serum solubility of a paclitaxel coating comprising varying amounts of the dihydrate paclitaxel and the amorphous paclitaxel.

Based on the first order rate constants obtained for amorphous paclitaxel ($k_1$=0.0244 $min^{-1}$) and for dihydrate paclitaxel ($k_2$=0.0003 $min^{-1}$) in porcine serum, the rate of dissolution of a coating comprising of a mixture of amorphous and dihydrate taxane therapeutic agents in porcine serum can be formulated as a function of the proportion of each solid form by the formulae: $f=1-(ae^{k_1t}+(1-a)e^{k_2t})$ and $a=(1-f-e^{k_2t})/e^{k_1t}-e^{k_2t}$, where f is the fraction dissolved, $k_1$ and $k_2$ are the rate constants for amorphous and dihydrate paclitaxel respectively, a is the proportion of amorphous taxane therapeutic agent in the coating layer, (1−a) is the amount of dihydrate taxane therapeutic agent in the coating layer and e is the natural logarithmic base. FIG. 9 shows a plot of the predicted dissolution rates of various mixtures of amorphous paclitaxel and dihydrate paclitaxel having the first order rate constants $k_1$ and $k_2$ (respectively) in porcine serum as a function of time. A first trace 904 corresponds to the predicted dissolution profile of a coating comprising 10% amorphous paclitaxel (aPTX) and 90% dihydrate paclitaxel (dPTX). The composition corresponding to the traces of FIG. 9 is provided in Table 5 below. The percentage of the paclitaxel dissolved as a function of time for about 1 week (10,000 minutes) is shown for each trace.

TABLE 5

Compositions of predicted elution profiles shown in FIG. 9

| Trace in FIG. 9 | Percentage aPTX | Percentage dPTX |
| --- | --- | --- |
| 902 | 100 | 0 |
| 904 | 90 | 10 |
| 906 | 80 | 20 |
| 908 | 70 | 30 |
| 910 | 60 | 40 |
| 912 | 50 | 50 |
| 914 | 40 | 60 |
| 916 | 30 | 70 |
| 918 | 20 | 80 |
| 920 | 10 | 90 |
| 922 | 0 | 100 |

Notably, varying the relative amounts of amorphous and dihydrate paclitaxel in the coating can result in wide variation of the rate of release of paclitaxel from the coating. Referring again to FIG. 9, after about 1-2 hours (100 minutes), less that 10% of the dihydrate paclitaxel coating (922) is predicted to be dissolved, while about 80% of the amorphous paclitaxel coating (902) is predicted to be dissolved. Mixtures of amorphous and dihydrate paclitaxel (904-920) can show intermediate amounts of elution. Similarly, after about 16 hours (1,000 minutes), less than 30% of the dihydrate paclitaxel coating (922) is predicted to be dissolved, about 100% of the amorphous paclitaxel coating (902) is predicted to be dissolved and mixtures of amorphous and dihydrate paclitaxel (904-920) can show intermediate amounts of elution. Finally, after about 1 week (10,000 minutes), about 90-95% of the dihydrate paclitaxel coating (922) is predicted to be dissolved, with mixtures of amorphouse and dihydrate paclitaxel (904-920) showing nearly 100% elution.

The elution profiles of coatings modeled by the traces of FIG. 9 correspond to coatings having a taxane therapeutic agent distributed in a mixture of multiple solid forms within the coating, most preferably a coating formed from a mixture of amorphous state paclitaxel and a solvated (e.g., dihydrate) solid form paclitaxel. A coating having a mixture of the amorphous and taxane therapeutic agent solid forms can be prepared as described above with respect to the third embodiment.

The dihydrate paclitaxel taxane therapeutic agent is typically less soluble than the amorphous taxane therapeutic agent or the anhydrous taxane therapeutic agent. In porcine serum at 25° C., samples of the dihydrate paclitaxel solid form were about 100-times less soluble than samples of the anhydrous paclitaxel solid form. Other studies have reported decreased solubility of dihydrate paclitaxel in water at 37° C. compared to anhydrous paclitaxel. Anhydrous paclitaxel is reported with a solubility of about 3.5 μg/mL after about 5 hours in 37° C. water, while dihydrate paclitaxel has a solubility of less than 1.0 μg/mL in 37° C. water over the same time period. R. T. Liggins et al., "Solid-State Characterization of Paclitaxel," *Journal of Pharmaceutical Sciences*, v. 86, No. 12, 1458-1463 (December 1997).

Coating Durability

The coating compositions preferably comprise a taxane therapeutic agent with a desired level of durability for an intended use. Coatings consisting of dihydrate taxane therapeutic agents demonstrated a low durability, and a high propensity for dissociation from the stent coating upon crimping. In contrast, the amorphous solid form of the taxane therapeutic agents demonstrated greater durability and substantially lower tendency to dissociate from a coated stent upon crimping of the stent. In aqueous media such as porcine serum and blood, the amorphous taxane therapeutic agent solid form is more soluble than the dihydrate taxane therapeutic agent. Therefore, the release rate and the durability of the coating can be altered by incorporating a desired amount of dihydrate or amorphous solid forms of the taxane therapeutic agent in one or more coating layers. Preferred coatings comprise one or more durable layers comprising a suitable amount of an amorphous taxane therapeutic agent solid form to impart a desired durability to the coating. For example, the outer layer can comprise at least about 5, 10, 15, 20, 25, 30, 35, 40, 45, 50, 60, 70, 80%, or more, of an amorphous taxane therapeutic agent to impart durability to a coating for sustained release coatings, durability may be balanced with the goal of extending the elution time by adding more of the slower-eluting dihydrate taxane therapeutic agent.

Coating durability describes the resistance of a coating to loss of integrity due to abrasion, bending or mechanical loading through mechanisms such as flaking, cracking, chipping and the like. The durability of a coating can be measured by weighing a coated medical device prior to physical agitation of the coating by a test process such as crimping, shaking, freezing or abrading the stent, weighing the coated stent a second time after the test process is performed, and comparing the second weight to the first weight. For a given physical test procedure, coating durability can be quantified by the amount of weight loss from the first weight to the second weight. Accordingly, the lower the amount of weight loss as a result of performing a physical test on the coated medical device, the more durable the coating is. One preferred physical test for implantable coated vascular stents is the process of crimping the stent from an expanded state (in which the stent is coated), to a radially compressed state for delivery within a body vessel. The durability of a radially expandable medical device can be quantified as the percentage weight loss of the coated medical device before and after crimping the medical device.

The difference in weight of a coated stent before and after crimping provides one indicator of the coating durability. Highly durable coatings typically have a lower weight loss during the crimping process. Taxane coatings with a higher proportion of dihydrate are typically less durable (i.e., higher weight loss during the crimping process). Preferred taxane coatings exhibit a coating weight loss of less than about 10%, more preferably less than about 8%, 6%, 4%, 3%, 2%, 1% or 0.5% and most preferably less than about 0.1% before and after crimping to a diameter of 6 French (6F). The coating weight loss can be measured by: (1) weighing an uncoated stent in the radially expanded state to obtain a first weight ("weight (1)"), (2) coating the stent in the expanded condition, (3) weighing the coated stent to obtain a second weight ("weight (2)"), (4) crimping the coated stent and (5) weighing the crimped, coated stent to obtain a third weight ("weight (3)"). The coating weight loss is: [weight (2)–weight (1)]–[weight (3)–weight (1)], or simply weight (2)-weight (3). Accordingly, one particularly preferred coating comprises a mixture of amorphous taxane therapeutic agent and dihydrate taxane therapeutic agent. Coatings comprising mixtures of dPTX with at least about 25-50% aPTX on the outside surface of the coating have shown desired durability characteristics. As discussed above with respect to FIG. 9, increasing the proportion of aPTX increases the elution rate of the coating in porcine serum. Particularly preferred coatings applied with a 4.68 mM paclitaxel solution comprise about 30% aPTX and 70% dPTX. These preferred ratios change as the concentration of paclitaxel in the spray coating solution changes, as discussed above. A stent comprising a 30:70 aPTX:dPTX was coated in a radially expanded state, crimped to fit a delivery catheter, and re-weighed. For example, a typical 30:70 aPTX:dPTX coated stent lost less than 5% weight as a result of crimping to a 6F size.

The durability of the coating may also be evaluated as the resistance to displacement of the coating in response to mechanical abrasion. For instance, scraping a non-durable coating may displace a portion of the coating from one area to another, resulting in a scratching or pitting of the surface without a net change in the weight of the coating. Preferably, coatings are sufficiently durable to resist displacement by mechanical abrasion as well as weight loss. Preferred coatings have a substantially uniform and smooth surface. Most preferably, coatings maintain a surface roughness (peak to valley) that is less than 50%, preferably 25%, of the total thickness of the coating. For instance, for a 10 micrometer thick coating, the surface is preferably not more than about 5 micrometers from its highest peak to its lowest valley. Also preferably, the coating roughness does not increase as a result of mechanical abrasion of a type encountered in crimping and loading the coated medical device into a delivery catheter.

FIGS. 10A-13B are optical micrographs of durable paclitaxel coatings on stents comprising various mixtures of dPTX and aPTX. The ratio of amorphous to dihydrate paclitaxel in each coating was subsequently determined by a monitoring a characteristic paclitaxel UV absorption peak (e.g., 227 nm) in an elution media in contact with the paclitaxel coated stents. This determination was performed by dissolving the coating in two different elution media separately contacted with the coating. First, paclitaxel was eluted from the coated stents using a first elution medium (the modified porcine serum) in which the dihydrate is substantially less soluble than the amorphous solid form of paclitaxel. Second, after elution of the dihydrate paclitaxel from the stents, the remaining paclitaxel was eluted from the coated stents using a second elution medium (0.3% Sodium Dodecyl Sulfate) effective to readily dissolve the remaining paclitaxel (presumed to be the more slowly soluble dihydrate) in the coating (without the first elution medium). Based on the comparative solubility of the dPTX and aPTX solid forms in the first and second elution media (see, e.g., FIG. 6A and FIGS. 7A-7B), the concentration of paclitaxel in the elution media was used to determine the ratio of solid forms present in the taxane coatings on the stents.

Figure 10A:
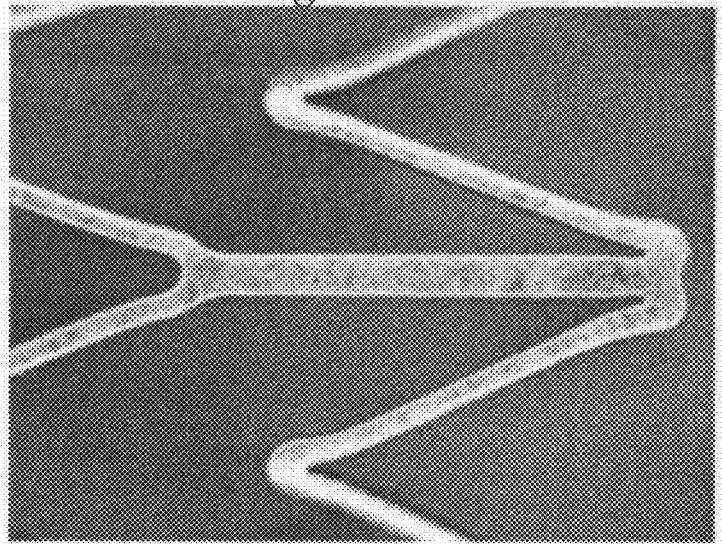
FIG. 10A and FIG. 10B are optical micrographs of a paclitaxel coated stent.
Figure 10B:
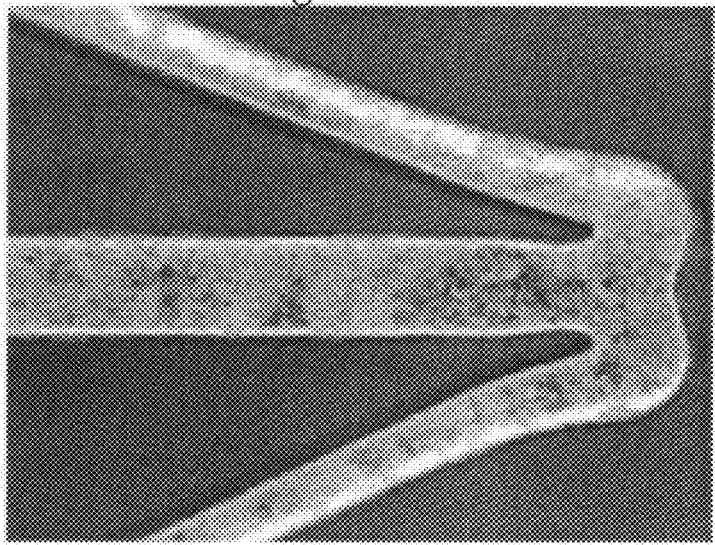

A mixture of amorphous and dihydrate taxane therapeutic agent coating has a cloudy or spotted appearance (clear coating with white opaque regions). FIG. 10A shows a 50× optical micrograph of a metal stent coated with about 65% dihydrate paclitaxel (35% amorphous paclitaxel) coating prepared by untrasonic spray coating a 4.68 mM paclitaxel solution in a 93% v methanol (7% water) solvent. FIG. 10B shows a 115× optical micrograph of the coating shown in FIG. 10A. The 65:35 w/w dPTX:aPTX coating has a largely cloudy and spotty appearance due to the presence of the dihydrate solid form of paclitaxel. Opaque white regions appear in the coating due to the mixture of the dihydrate (opaque, white) with lesser amounts of the amorphous (clear) solid form of paclitaxel.

Figure 11A:
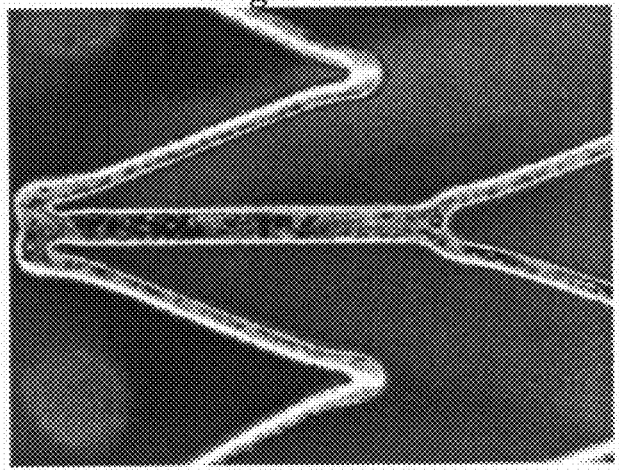
FIG. 11A and FIG. 11B are optical micrographs of a paclitaxel coated stent.
Figure 11B:
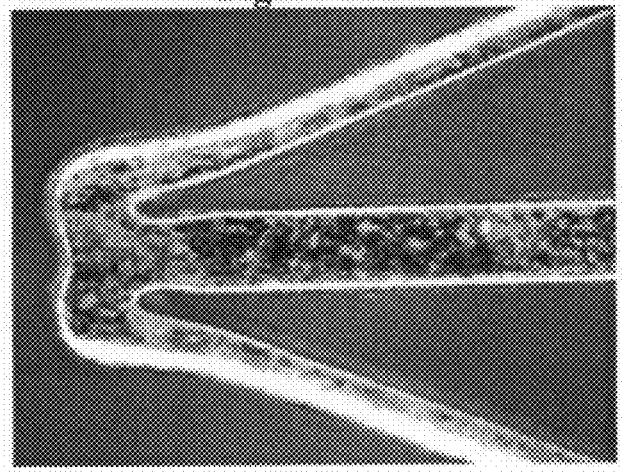

FIG. 11A shows a 50× optical micrograph of an metal stent coated with about 50% dihydrate paclitaxel (50% amorphous paclitaxel) coating prepared by untrasonic spray coating a 4.68 mM paclitaxel solution in a 94% v methanol (6% water) solvent. FIG. 11B shows a 115× optical micrograph of the coating shown in FIG. 11A. The 50:50 w/w dPTX:aPTX coating has a clearer and less spotty appearance compared to the coating in FIGS. 10A-10B due to the increased proportion of the amorphous solid form of paclitaxel. Regions of varying opacity in the coating result from the mixture of the amorphous (clear) solid form of paclitaxel with the dihydrate (opaque, white) solid form.

Figure 12A:
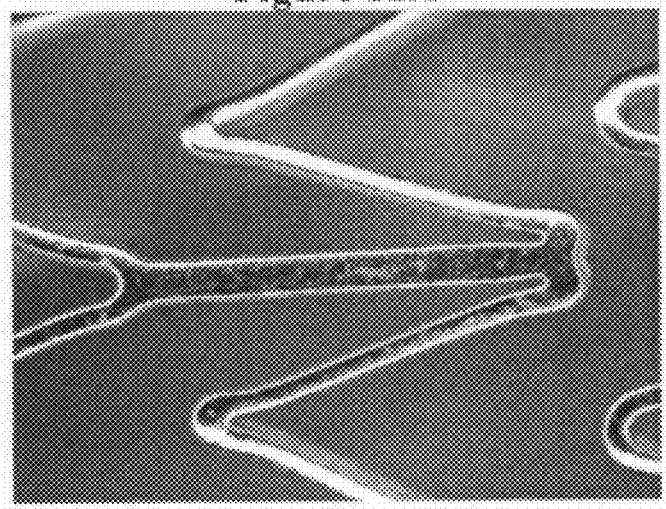
FIG. 12A and FIG. 12B are optical micrographs of a paclitaxel coated stent.
Figure 12B:
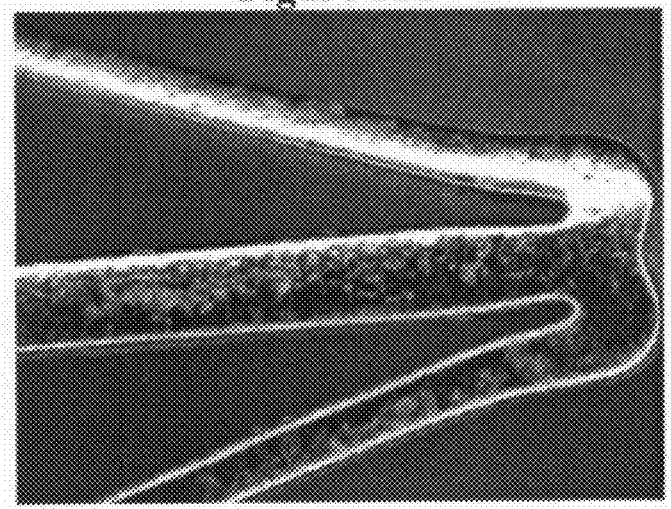

FIG. 12A shows a 50× optical micrograph of an metal stent coated with about 40% dihydrate paclitaxel (60% amorphous paclitaxel) coating prepared by untrasonic spray coating a 4.68 mM paclitaxel solution in a 95% v methanol (5% water) solvent. FIG. 12B shows a 115× optical micrograph of the coating shown in FIG. 12A. The 40:60 w/w dPTX:aPTX coating has a clearer and less spotty appearance than the coating in FIGS. 10A-10B due to the increased proportion of the amorphous solid form of paclitaxel. Regions of varying opacity in the coating result from the mixture of the amorphous (clear) solid form of paclitaxel with the dihydrate (opaque, white) solid form.

Figure 13A:
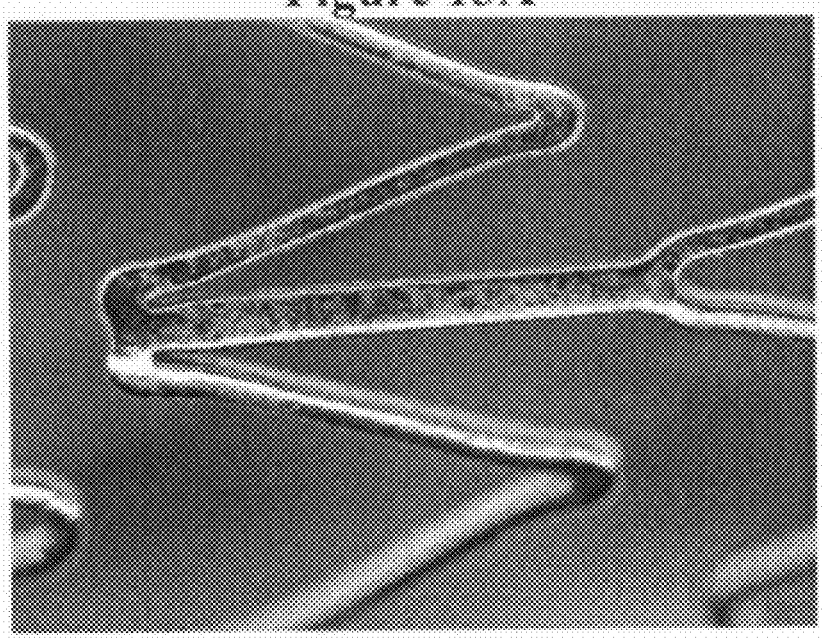
FIG. 13A and FIG. 13B are optical micrographs of a paclitaxel coated stent.
Figure 13B:
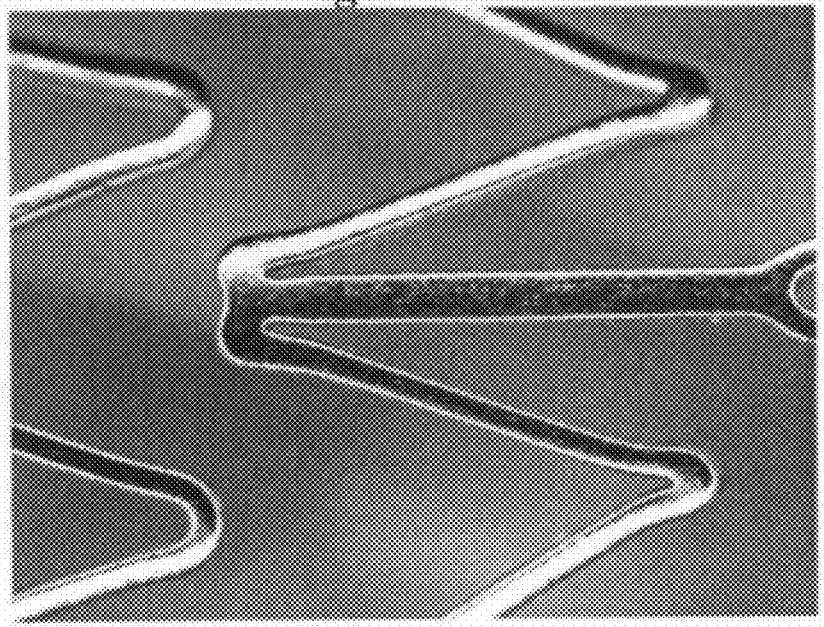

FIG. 13A shows a 50× optical micrograph of an metal stent coated with about 100% amorphous paclitaxel coating prepared by untrasonic spray coating a 4.68 mM paclitaxel solution in a 95% v methanol (5% water) solvent. FIG. 13B shows a 115× optical micrograph of the coating shown in FIG. 13A. The aPTX coating has a clearer appearance indicative of the amorphous (clear) solid form of paclitaxel.

Notably, as the dose of paclitaxel increases, more dihydrate solid form is typically needed to maintain a given level of durability. For example, a paclitaxel-only coating having a 50:50 ratio of the dihydrate:amorphous solid forms was durable at a dose of 3 µg/mm² but not for a dose of 1 µg/mm². That is, paclitaxel coatings with greater than 50% dihydrate solid form were typically required to maintain durability at the 1 µg/mm² coating that was comparable to the 3 µg/mm² coating.

Table 6 below provides examples of preferred abluminal paclitaxel coatings on a 6×20 radially expandable vascular stent, showing the relationship between the composition of the spray solution and the resulting coating composition. Each coating is deposited using ultrasonic deposition according to Table 4 above at a temperature of about 87 F. The spray solution included the concentration of paclitaxel in Table 6 with methanol and water in a ratio that provides a desired amount of the dihydrate solid form. As described by Table 3a and Table 3b, increasing the amount of methanol relative to water resulted in less dihydrate in the coating at any concentration of paclitaxel.

TABLE 6

Preferred Paclitaxel Coatings

| Paclitaxel Dose (µg/mm²) | Total Paclitaxel (µg) | Preferred dPTX:aPTX for durability (%:%) | Concentration Paclitaxel in Spray Solution (mM) |
| --- | --- | --- | --- |
| 0.06 | 5 | 80:20 | 0.70 |
| 0.30 | 24 | 75:25 | 1.17 |
| 1.00 | 74 | 70:30 | 2.34 |
| 3.00 | 219 | 50:50 | 4.68 |

Medical Devices

The coatings may be applied to one or more surfaces of any implantable medical device having any suitable shape or configuration.

The medical device may be adapted or selected for temporary or permanent placement in the body for the prophylaxis or treatment of a medical condition. For example, such medical devices may include, but are not limited to, stents, stent grafts, vascular grafts, balloon catheters, catheters, guide wires, balloons, filters (e.g. vena cava filters), cerebral aneurysm filler coils, intraluminal paving systems, sutures, staples, anastomosis devices, vertebral disks, bone pins, suture anchors, hemostatic barriers, clamps, screws, plates, clips, slings, vascular implants, tissue adhesives and sealants, tissue scaffolds, myocardial plugs, pacemaker leads, valves (e.g. venous valves), abdominal aortic aneurysm (AAA) grafts, embolic coils, various types of dressings, bone substitutes, intraluminal devices, vascular supports, or other known bio-compatible devices.

In general, intraluminal stents are preferred surfaces for use with the coatings described herein. Stents may typically comprise a plurality of apertures or open spaces between metallic filaments (including fibers and wires), segments or regions. Typical stent structures include: an open-mesh network comprising one or more knitted, woven or braided metallic filaments; an interconnected network of articulable segments; a coiled or helical structure comprising one or more metallic filaments; and, a patterned tubular metallic sheet (e.g., a laser cut tube). Examples of suitable intraluminal stents include endovascular, biliary, tracheal, gastrointestinal, urethral, ureteral, esophageal and coronary vascular stents. Although certain embodiments are described herein with reference to vascular stents, other embodiments relate to coatings on other types of stents.

The stent may be part of a stent graft, a bifurcated stent, a coronary vascular stent, a urethral stent, a ureteral stent, a biliary stent, a tracheal stent, a gastrointestinal stent, or an esophageal stent, for example. More specifically, the stent may be, for example, a Wallstent, Palmaz-Shatz, Wiktor, Strecker, Cordis, AVE Micro Stent, lgaki-Tamai, Millenium Stent (Sahajanand Medical Technologies), Steeplechaser stent (Johnson & Johnson), Cypher (Johnson & Johnson), Sonic (Johnson & Johnson), BX Velocity (Johnson & Johnson), Flexmaster (JOMED) JoStent (JOMED), S7 Driver (Medtronic), R-Stent (Orbus), Tecnic stent (Sorin Biomedica), BiodivYsio (Abbott), Trimaxx (Abbott), DuraFlex (Avantec Vascular), NIR stent (Boston Scientific), Express 2 stent (Boston Scientific), Liberte stent (Boston Scientific), Achieve (Cook/Guidant), S-Stent (Guidant), Vision (Guidant), Multi-Link Tetra (Guidant), Multi-Link Penta (Guidant), or Multi-Link Vision (Guidant). Some exemplary stents are also disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz, and U.S. Pat. No. 5,421,955 to Lau. Desirably, the stent is a vascular stent such as the commercially available Gianturco-Roubin FLEX-STENT®, GRII™, SUPRA-G, ZILVER or V FLEX coronary stents from Cook Incorporated (Bloomington, Ind.).

The stent or other medical device may be made of one or more suitable biocompatible materials such as stainless steel, nitinol, MP35N, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and/or composites or alloys, or as carbon or carbon fiber. Other materials for medical devices, such as drainage stents or shunts, include cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene teraphthalate, polyurethane, polyamide, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as, polylacetic acid, polyglycolic acid or copolymers thereof, a polyanhydride, polycaprolactone, polyhydroxybutyrate valerate or other biodegradable polymer, or mixtures or copolymers thereof; extracellular matrix components, proteins, collagen, fibrin or other therapeutic agent, or mixtures thereof. Desirably, the device is made of stainless steel, cobalt-chromium or a nickel-titanium alloy (e.g., Nitinol).

The stent may be deployed according to conventional methodology, such as by an inflatable balloon catheter, by a self-deployment mechanism (after release from a catheter), or by other appropriate means. The stent may be formed through various methods, such as welding, laser cutting, or molding, or it may consist of filaments or fibers that are wound or braided together to form a continuous structure. The stent may also be a grafted stent in which the therapeutic agent is incorporated into the graft material.

Methods of Treatment

Methods of treatment preferably include the step of inserting into a patient a coated medical device having any of the compositions and/or configurations described above. For example, when the medical device is a stent coated by the coating methods described above, the method of treatment involves implanting the stent into the vascular system of a patient and allowing the therapeutic agent(s) to be released from the stent in a controlled manner, as shown by the drug elution profile of the coated stent.

In one preferred embodiment, the coated medical devices are implanted to treat peripheral vascular disease, for example by implanting the coated medical device in a peripheral artery. In one aspect, methods of treating peripheral vascular disease (PVD) are provided. PVD is a disease of the lower extremities that may present various clinical indications ranging from asymptomatic patients, to patients with chronic critical limb ischemia (CLI) that might result in amputation and limb loss.

Methods of treating peripheral vascular disease, including critical limb ischemia, preferably comprise the endovascular implantation of one or more coated medical devices provided herein. Atherosclerosis underlies many cases of peripheral vascular disease, as narrowed vessels that cannot supply sufficient blood flow to exercising leg muscles may cause claudication, which is brought on by exercise and relieved by rest. As vessel narrowing increases, critical limb ischemia (CLI) can develop when the blood flow does not meet the metabolic demands of tissue at rest. While critical limb ischemia may be due to an acute condition such as an embolus or thrombosis, most cases are the progressive result of a chronic condition, most commonly atherosclerosis. The development of chronic critical limb ischemia usually requires multiple sites of arterial obstruction that severely reduce blood flow to the tissues. Critical tissue ischemia can be manifested clinically as rest pain, nonhealing wounds (because of the increased metabolic requirements of wound healing) or tissue necrosis (gangrene).

The coated medical device can be implanted in any suitable body vessel. Typical subjects (also referred to herein as "patients") are vertebrate subjects (i.e., members of the subphylum cordata), including, mammals such as cattle, sheep, pigs, goats, horses, dogs, cats and humans. Sites for placement of the medical devices include sites where local delivery of taxane therapeutic agents are desired. Common placement sites include the coronary and peripheral vasculature (collectively referred to herein as the vasculature). Other potential placement sites include the heart, esophagus, trachea, colon, gastrointestinal tract, biliary tract, urinary tract, bladder, prostate, brain and surgical sites, particularly for treatment proximate to tumors or cancer cells. Where the medical device is inserted into the vasculature, for example, the therapeutic agent is may be released to a blood vessel wall adjacent the device, and may also be released to downstream vascular tissue as well.

The configuration of the implantable frame can be selected based on the desired site of implantation. For example, for implantation in the superficial artery, popliteal artery or tibial artery, frame designs with increased resistance to crush may be desired. For implantation in the renal or iliac arteries, frame designs with suitable levels of radial force and flexibility may be desired. Preferably, a coated vascular stent is implanted in a non-coronary peripheral artery, such as the iliac or renal arteries.

In one embodiment, a medical device comprising a balloon-expandable frame portion coated with a taxane therapeutic agent can be endoluminally delivered to a point of treatment within an infrapopliteal artery, such as the tibial or peroneal artery or in the iliac artery, to treat CLI. For treating focal disease conditions, coated balloon-expandable medical devices can comprise an expandable frame attached to a coating. The frame can be also be formed from a bioabsorbable material, or comprise a coating of the therapeutic agent material over at least a portion of the frame. The frame can be configured to include a barb or other means of securing the medical device to the wall of a body vessel upon implantation.

In another aspect, a coated medical device can be a self-expanding device such as a coated NITINOL stent coated with the taxane therapeutic agent, and configured to provide a desirable amount of outward radial force to secure the medical device within the body vessel. The medical device can be preferably implanted within the tibial arteries for treatment of CLI. For instance, the coated medical device can be configured as a vascular stent having a self-expanding support frame formed from a superelastic self-expanding nickel-titanium alloy coated with a metallic bioabsorbable material and attached to a graft material. A self-expanding frame can be used when the body vessel to be stented extends into the distal popliteal segment. The selection of the type of implantable frame can also be informed by the possibility of external compression of an implant site within a body vessel during flexion of the leg.

A consensus document has been assembled by clinical, academic, and industrial investigators engaged in preclinical interventional device evaluation to set forth standards for evaluating drug-eluting stents such as those contemplated by the present invention. See "Drug-Eluting Stents in Preclinical Studies—Recommended Evaluation From a Consensus Group" by Schwartz and Edelman (available at "http://www.circulationaha.org" (incorporated herein by reference).

EXAMPLES

In the following examples, the equipment and reagents specified below were used:

TABLE 7

| Equipment Name | Manufacturer | Manufacturer ID | Vendor |
| --- | --- | --- | --- |
| 1 μg Balance | Mettler | AX 26 | VWR |
| 10 μg Balance | Mettler | AX 105 DR | VWR |
| Top Loading Balance | Ohaus | GT 4100 (not avail.) | VWR |
| Inline Spectrometer | Agilent | 8453 | Agilent |
| Chemstation | Agilent | Version A.10.01 | Agilent |
| Coating Spectrometer 1 | Perkin Elmer | Lambda 14 P | Perkin Elmer |
| Coating Spectrometer 2 | Perkin Elmer | Lambda 45 | Perkin Elmer |
| UV Winlab | Perkin Elmer | Version 5.1 | Perkin Elmer |
| Cuvettes | Perkin Elmer | B0631077 | VWR |
| Electrostatic Coater | Terronics | Custom | Terronics |
| MED Spray Gun/Badger | Badger | Model 200 | Ding-A-Ling |
| Cook Incorporated Spray Gun | EFD | 780S-SS | EFD |
| Cook Incorporated Spray Controller | EFD | Valvemate 7040 | EFD |
| Microscope | Leica | MZ-16 | Nuhsbaum Inc. |
| Image Pro Plus | MediaCybernetics | Version 5.1 | Media Cybernetics |
| Microsoft Office | Microsoft | Version 2003 | New Egg |
| Stopwatch | Private Label | n/a | VWR |
| Glassware | Kimball | Various | VWR |
| Ethanol | Aaper | E 200 PP | Aaper |
| Methanol | Sigma | M 3641 | Sigma |
| Dichloromethane | Sigma | 15,479-2 | Sigma |
| Water | Ricca Chemical | 9150-5 | VWR |

Example 1

Preparation of Amorphous, Anhydrous and Dihydrate Paclitaxel

Bulk samples of amorphous, anhydrous and dihydrate paclitaxel solid forms were prepared by the methods described below.

Samples of bulk amorphous paclitaxel were prepared as follows: 1.01 g of paclitaxel (Phytogen Life Sciences) was dissolved in 5 mL dichloromethane (Mallinckrodt) while agitating to form a paclitaxel solution; the paclitaxel solution was left open to air at about 23° C. for about 10 hours to permit evaporation of the dichloromethane and formation of amorphous paclitaxel. The melting temperature of the amorphous paclitaxel was 209-215° C.

Samples of bulk anhydrous paclitaxel were prepared as follows: 1.06 g of paclitaxel (Phytogen Life Sciences) were dissolved in 40 mL methanol (Sigma Aldrich, 99.93% HPLC Grade) while sonnicating the container and inversion of the container to form a paciatxel solution; about 2 mL of hexane (Sigma Aldrich) was added to the paclitaxel solution, and the solution was placed in a freezer at about −20° C. overnight (approximately 10 hours) to form anhydrous crystalline paclitaxel. The melting temperature of the anhydrous paclitaxel was 190-210° C.

Samples of dihydrate paclitaxel were prepared as follows: 1.09 g paclitaxel (Phytogen Life Sciences) were dissolved in 25 mL methanol while sonnicating the container to form a paclitaxel solution; about 5 mL of water was added to the paclitaxel solution; and the sample was placed in a freezer at about −20° C. overnight to form dihydrate crystals. The melting temperature of the dihydrate crystal was 209-215° C. Subsequently, the sample was sealed under vacuum to 0.025 torr for 2.5 hours to remove residual solvent. Dihydrate paclitaxel samples were also prepared as follows: 50.08 g paclitaxel (Phytogen Life Sciences) was dissolved in 1.1 L methanol to form a solution; 275 mL water was subsequently added to the methanol solution in a drop-wise fashion to form a precipitate that was refrigerated at about −20° C. overnight (about 10 hours); the resulting solid precipitate was filtered, dissolved in 1500 mL methanol and 375 mL water, and was subsequently added in a drop-wise fashion; the resulting crystals were recrystallized a third time using 1200 mL methanol with 300 mL water; and the resulting dihydrate crystals were collected.

Example 2

Ultraviolet (UV) Spectra of Bulk Paclitaxel Samples

The three solid samples prepared in Example 1 (amorphous, dihydrate and anhydrous paclitaxel) were dissolved in ethanol to form spray solutions. The ultraviolet spectra of each of the three samples were taken (Agilent In-Line UV Spectrophotometer), to obtain three spectra that were indistinguishable from the spectrum 100 shown in FIG. 2. The spectra all included a peak at 227 nm indicative of the taxane core structure in the paclitaxel, indicating that the paclitaxel solid forms of Example 1 were not distinguishable from each other based on UV spectra of the paclitaxel in solution.

Example 3

Infrared Spectra of Bulk Paclitaxel Samples

FTIR Infrared spectra each of the samples prepared in Example 1 were obtained following procedure: a pellet of KBr was made by grinding the paclitaxel crystal with KBr using a mortar and pestel at room temperature (about 23° C.); the resulting solid was placed under vacuum to remove residual methanol solvent (0.025 mmHg); and a spectra was recorded of the paclitaxel analyte. Representative spectra of each solid form of paclitaxel are provided in FIGS. 3A-3C, as discussed above. Infrared spectra may also be obtained using Attenuated Total Reflection Infrared (ATR-IR) from a coating or a small sample of a solid taxane sample from a coating. One suitable ATR-IR apparatus is the PerkinElmer Horizontal ATR model L1200361.

Example 4

Spray Gun Coating of Stents with Paclitaxel

Paclitaxel coatings comprising amorphous paclitaxel, dihydrate paclitaxel and mixtures thereof were deposited by spraying a solution of paclitaxel in ethanol from an EFD 780S-SS spray valve system (EFD, Inc., East Providence, R.I.) (hereinafter, "spray gun"). In spray coating with the EFD 780S-SS spray valve system, decreasing the atomization pressure (larger spray particle size), increasing the fluid pressure (increasing the flow rate) and/or humidity during the spraying process favor the increased formation of water solvated dihydrate solid forms over amorphous or anhydrous forms. Increased temperature is also believed to favor formation of the solvated dihydrate solid forms. Increasing the tank pressure can result in a higher flowrate from the spray gun nozzle, and favor the deposition of more of the dihydrate solid form. Increasing the atomization pressure can result in a finer mist being sprayed from the spray gun, favoring the deposition of more amorphous taxane therapeutic coatings, with less dihydrate solid form.

Overall, typical spray parameters for deposition of a taxane therapeutic agent with the EFD 780S-SS spray valve system include: (1) a relative humidity of between about 5% and about 80% (depending on the solid form of the coating desired) (2) an atomization pressure of between about 2.00 psi and 25.00 psi (depending on the type of solid form of coating desired); (3) an ambient temperature of about 65° F. to about 85° F.; and (4) a fluid pressure of between about 1.00 psi and 10.00 psi.

Spray coating process conducted under one or preferably more of the following conditions with the EFD 780S-SS spray valve system resulted in increased formation of a dihydrate taxane therapeutic agent solid form in a coating: (1) a relative humidity of greater than 40% and (2) an atomization pressure of less than 10 psi. A dihydrate taxane therapeutic agent coating has a white, cloudy or opaque appearance. The dihydrate taxane therapeutic agent coatings were made by: dissolving solid 4 g paclitaxel in 1 L ethanol to form a solution, and spraying the solution onto a medical device with an atomization pressure of 10 psi or less in an environment having a relative humidity of 40% or greater. The spraying step was performed at a temperature of about 75° F. or greater, and with a fluid pressure of between about 1.00 and 5.00 psi. Dihydrate paclitaxel (dPTX) coatings were deposited under the following conditions: (1) 4.0 g/L PTX (4.68 mM) in ethanol spray solution, 44% relative humidity, 12.00 psi atomization pressure, 2.50 psi fluid (tank) pressure and 80° F. ambient temperature; or (2) 4.0 g/L PTX in ethanol spray solution, 55% relative humidity, 5.00 psi atomization pressure, 1.00 psi fluid (tank) pressure and 70° F. ambient temperature.

Coatings comprising mixtures of amorphous paclitaxel (aPTX) and dihydrate paclitaxel (dPTX) were deposited under the following conditions: (1) 4.0 g/L PTX in ethanol spray solution, 30% relative humidity, 13 psi atomization pressure, 1.5 psi fluid (tank) pressure and 70° F. ambient temperature. The flow rate of the solution through the spray gun was about 8 mL/min. The spray gun was passed over the stents for multiple passes until a desired dose of paclitaxel was coated on the abluminal surface of the stents. The paclitaxel coatings contained between 0.2 and 4 µg of the taxane therapeutic agent per mm² of the abluminal surface area of the stent, depending on the number of passes of the spray gun. For example, a 6×20 mm stent may be coated was coated with a total of 219 µg of paclitaxel at an abluminal surface concentration of about 3 µg/mm² of paclitaxel. A 3×20 mm stent was coated with a total of about 120 µg of paclitaxel at the same abluminal surface concentration of about 3 µg/mm² of paclitaxel.

Example 5

Ultrasonic Spray Coating of Stents with Paclitaxel

Stents with coatings consisting of paclitaxel taxane therapeutic agent coatings including both the dihydrate solid form and in the amorphous solid forms of paclitaxel were prepared by spray coating a solution comprising paclitaxel, methanol and water. A paclitaxel solution in methanol and water was prepared. Specifically, a 1.74 mM paclitaxel solution was prepared in 68% methanol by dissolving 7.43 mg of paclitaxel in 5 mL of previously made solution of 68% methanol 32% water. The solution was sprayed from an ultrasonic spray gun (Sono-tek Model 06-04372) in a glove box. Before spraying, the glove box was purged with nitrogen at 20 psi for 15 minutes. The atmosphere in the glove box was adjusted until the oxygen meter reads a constant 200 ppm within the glove box. The heat in the glovebox was set to 31° C. (88° F.), the air shroud to 2.0 psi and the ultrasonic power to 1.0 W. The paclitaxel solution was loaded into a syringe and place on the syringe pump in the ultrasonic coating apparatus and a bare metal stent (6×20 ZILVER, Cook Inc., Bloomington, Ind.) was mounted on a mandrel aligned with the spray nozzle. The solution was sprayed onto a stent using a 60 kHz nozzle at a flow rate of 0.03 mL/min, a coating velocity of 0.025 in/sec, a nozzle power of 1.0 W, a process gas pressure of 2.0 psi, and a distance from the nozzle to the stent of about 12 mm, while rotating the stent with an axial rotation rate of 60 rpm. Only the abluminal surface of the stent was coated.

Example 6

Elution of Paclitaxel-Coated Stents in Porcine Serum

Stents with coatings consisting of paclitaxel taxane therapeutic agents in both the dihydrate solid form and in the amorphous form were prepared by spray coating a solution comprising various amounts of paclitaxel, methanol and water. A 2.34 mM paclitaxel solution in 88% methanol and 12% water (v) was made with a total volume of about 10 mL (20.04 mg paclitaxel). Twelve (12) 6×20 ZILVER (Cook Inc., Bloomington, Ind.) stents were spray coated using the ultrasonic coating procedure of Example 5 and the parameters in Table 8 below. Table 8 also shows the amount of paclitaxel coated on each stent.

TABLE 8

Coating Parameters for Stents Coated with 2.34 mM Paclitaxel

| Coating Solution | 2.34 mM PTX in 88% MeOH/H₂O | | | |
|---|---|---|---|---|
| Stents | 1-3 | 4-6 | 7-9 | 10-12 |
| Relative Humidity (%) | 8.7-13.3 | 7.3-8.5 | 7.1-8.3 | 7.4-8.2 |
| Temperature (degrees F.) | 82.4-83.1 | 83.1 | 83.3-83.4 | 83.7-84.0 |
| Target Dose (µg) | 74 | | | |
| Actual Dose (µg) | 84 ± 5.89 | | | |
| Flow Rate (mL/min) | 0.03 | | | |

TABLE 8-continued

Coating Parameters for Stents Coated with 2.34 mM Paclitaxel

| Coating Solution | 2.34 mM PTX in 88% MeOH/H₂O |
|---|---|
| Loops | 5 |
| Air Shroud (psi) | 1.0 |
| Linear Velocity (in/sec) | 0.025 |
| Rotational Velocity (rpm) | 60 |
| Oxygen Content (ppm) | 145-155 |
| Power (Watts) | 0.8 |
| Nozzle Distance from Stent (mm) | 8 |

Figure 14:
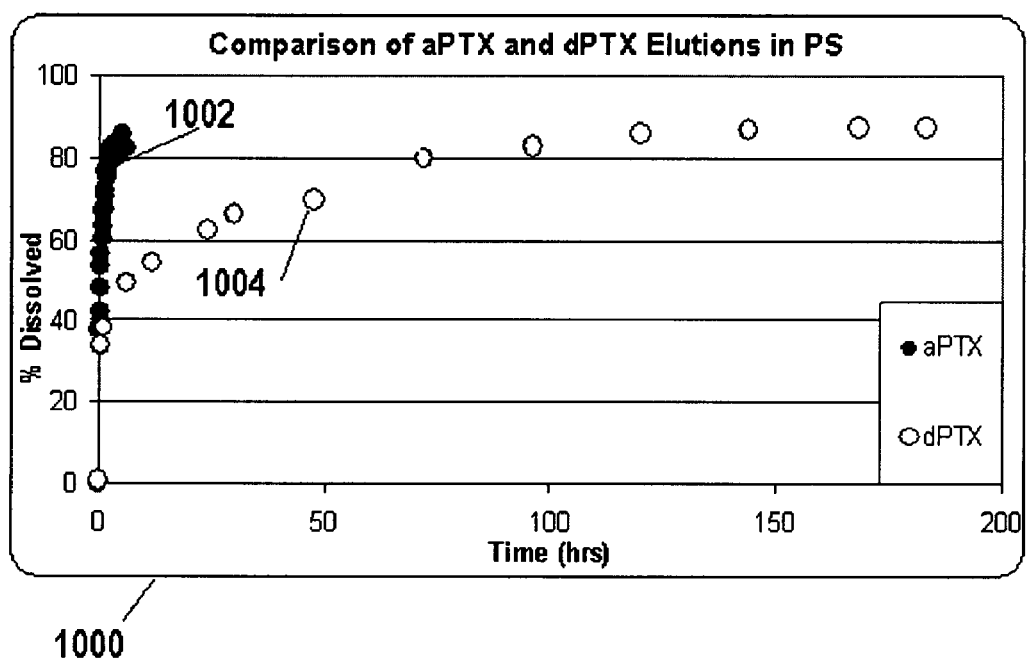
FIG. 14 is a graph showing the elution profiles of two different paclitaxel coated stents, described in Example 6.

FIG. 14 shows an elution graph 1000 comparing a first elution profile 1002 for a 100% amorphous paclitaxel coating (formed by spray coating an ethanol-paclitaxel according to Example 4) compared to a second elution profile 1004 obtained as the average of the 12 stent coatings according to Table 8 (containing about 50% dihydrate paclitaxel) (both in porcine serum). Increasing the amount of dihydrate resulted in sustained release of the paclitaxel in the second elution profile 1004 compared to the first elution profile 1002. FIG. 14 was obtained from a coated vascular stent having an amorphous paclitaxel (1002) or a 50% dihydrate:50% amorphous paclitaxel coating (1004) obtained in separate experiments during the continuous flow of a porcine serum elution medium. The coatings did not comprise a polymer. The amount of paclitaxel in the elution medium was measured by UV absorption at 227 nm. The first elution profile 1002 shows substantially all of the amorphous paclitaxel eluting within less than about 5 hours. The second elution profile 1004 in porcine serum elution medium showed about 60% of the paclitaxel coating eluted after about 25 hours and about 80% of the paclitaxel coating eluted from the coating after 75 hours.

Example 7

Elution of Paclitaxel-Coated Stents in HCD

Stents with coatings consisting of paclitaxel taxane therapeutic agents in both the dihydrate solid form and in the amorphous form were prepared by spray coating a solution comprising various amounts of paclitaxel, methanol and water. First, a first coating solution of 4.68 mM paclitaxel solution in 100% ethanol was prepared with 19.96 mg paclitaxel in 5 mL ethanol. Second, a second solution of 4.68 mM paclitaxel in 93% methanol and 7% water (v) was made with a total volume of about 5 mL (19.99 mg paclitaxel). Five (5) 6×20 ZILVER (Cook Inc., Bloomington, Ind.) stents were spray coated with the first spray solution and five (5) more 6×20 ZILVER (Cook Inc., Bloomington, Ind.) stents were spray coated with the second spray solution. All coating was performed on the abluminal surface only using the ultrasonic coating procedure of Example 5 and the parameters in Table 9 below. Table 9 also shows the amount of paclitaxel coated on each stent. Coatings formed from the first solution (ethanol) contained 93% amorphous paclitaxel, 7% dihydrate paclitaxel; coatings formed from the second solution (methanol/water) contained about 82% dihydrate and 18% amorphous paclitaxel.

TABLE 9

Coating Parameters for Stents Coated with 4.68 mM Paclitaxel

| Coating Solvent | EtOH | | 93% MeOH/H$_2$O | |
|---|---|---|---|---|
| Stents #s | 100-102 | 103-105 | 200-202 | 203-205 |
| Temperature (degrees F.) | 79.2 | 79.4-79.5 | 78.3-79.0 | 77.2-78.1 |
| Oxygen Content (ppm) | 135-165 | 125-145 | 135-145 | 135-180 |
| Relative Humidity (%) | 0.0 | | 0.0-0.8 | 0.0 |
| Power (Watts) | 1.1 | | 0.8 | |
| Actual Dose (μg) | 195 ± 17 | | 301 ± 10 | |
| Flow Rate (mL/min) | | 0.03 | | |
| Loops | | 7 | | |
| Air Shroud (psi) | | 1.0 | | |
| Linear Velocity (in/sec) | | 0.025 | | |
| Rotational Velocity (rpm) | | 60 | | |
| Nozzle Distance from Stent (mm) | | 8 | | |
| Target Dose (μg) | | 219 | | |

Figure 15:
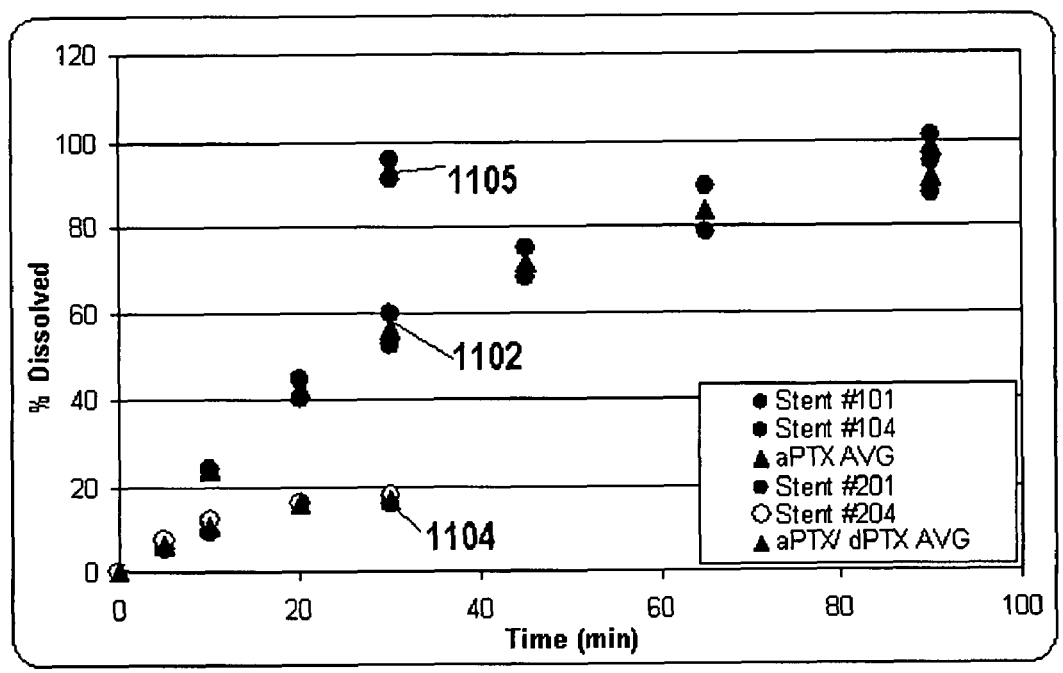
FIG. 15 is a graph showing the elution profiles from two different paclitaxel coated stents, described in Example 7.

FIG. 15 shows an elution graph 1100 obtained in a 0.5% aqueous HCD solution, comparing a first elution profile 1102 from the coatings formed from the 93% amorphous paclitaxel coating deposited from the first solution (formed by ultrasonic spray coating an according to Example 5, except as indicated in Example 7) compared to a second elution profile 1104 obtained from the stent coatings from the 82% dihydrate coating deposited from the second solution (formed by ultrasonic spray coating an according to Example 5, except as indicated in Example 7). The coatings did not comprise a polymer. The amount of paclitaxel in the elution medium was measured by UV absorption at 227 nm. The first elution profile 1102 shows a more rapid elution rate than the second elution profile 1104. Data points 1105 were obtained by contacting the coated stent formed from the second solution with 100% ethanol after obtaining the second elution profile 1104, resulting in rapid release of all remaining paclitaxel from the coating.

We claim:

1. A coated implantable medical device having at least one surface and comprising a coating on the at least one surface, the coating comprising:
   a taxane therapeutic agent including a taxane therapeutic agent in a first taxane solid form characterized by a vibrational spectrum comprising at least two peaks between 1735 and 1705 cm$^{-1}$ and a solubility of less than 20% wt. after 24 hours in porcine serum at 37° C., and
   a second taxane solid form of the taxane therapeutic agent characterized by a vibrational spectrum comprising one peak between 1735 and 1705 cm$^{-1}$ and a solubility of greater than 50% wt. after 24 hours in porcine serum at 37° C., wherein at least 10% of the taxane therapeutic agent is present in the first taxane solid form.

2. The medical device of claim 1, wherein the first solid form of the taxane therapeutic agent has a melting point of between about 210 and 215° C.

3. The medical device of claim 1, wherein the taxane therapeutic agent is paclitaxel.

4. The medical device of claim 1, wherein the implantable frame is a radially expandable vascular stent having a luminal surface and an abluminal surface, the at least one surface is the abluminal surface of the vascular stent, the coating comprises between 0.2 and 4 μg of the taxane therapeutic agent per mm$^2$ on the abluminal surface area of the stent, and the luminal surface has less than about 0.10 μg of the taxane therapeutic agent per mm$^2$ of luminal surface area.

5. The medical device of claim 1, wherein the coating is free of a polymer.

6. The medical device of claim 1, wherein the second taxane solid form is amorphous paclitaxel.

7. The medical device of claim 1, wherein the first taxane solid form is of dihydrate paclitaxel.

8. The medical device of claim 1, wherein the medical device comprises a radially expandable vascular stent, and crimping the stent to 6 French results in less than 10% weight loss in the weight of the coating.

9. A coated vascular stent having a luminal surface and an abluminal surface, the stent comprising: an implantable frame having at least one surface and a coating attached to the least one surface of the implantable frame, the coating comprising a first layer and a second layer, the first layer comprising a dihydrate taxane solid form characterized by a vibrational spectrum comprising at least two peaks between 1735 and 1705 cm$^{-1}$ and a solubility of less than 20% wt. after 24 hours in porcine serum at 37° C., and the second layer comprising an amorphous taxane solid form of the taxane therapeutic agent characterized by a vibrational spectrum comprising one peak between 1735 and 1705 cm$^{-1}$ and a solubility of greater than 50% wt. after 24 hours in porcine serum at 37° C.

10. The coated vascular stent of claim 9, wherein the taxane therapeutic agent is paclitaxel.

11. The coated vascular stent of claim 9, wherein the first layer further comprises at least 5% of the amorphous taxane solid form.

12. The coated vascular stent of claim 9, wherein second layer further comprises at least 5% of the dihydrate taxane solid form.

13. The coated vascular stent of claim 9, wherein the coating is a two-layer coating with the first layer positioned over the second layer, and the second layer is in contact with the at least one surface.

14. The coated vascular stent of claim 13, wherein the first layer is a mixture of the dihydrate taxane solid form and the amorphous taxane solid form comprising between about 35% to about 60% of the amorphous taxane solid form.

15. The coated vascular stent of claim 9, wherein the coating is a two-layer coating consisting of the second layer positioned over the first layer, and the first layer in contact with the at least one surface.

16. The coated vascular stent of claim 15, wherein the first layer is a mixture of the dihydrate taxane solid form and the amorphous taxane solid form comprising between about 35% to about 60% of the amorphous taxane solid form.

17. The coated vascular stent of claim 9, where the dose of taxane therapeutic agent on the abluminal surface is less than about 1.00 μg/mm$^2$.

18. The coated vascular stent of claim 9, wherein the coating further comprises a third layer comprising a first proportion of the amorphous taxane solid form and being positioned over the second layer, the second layer comprising a second proportion of the amorphous taxane solid form and being positioned between the third layer and the first layer and the first layer comprising a third proportion of the solid amorphous taxane solid form and being positioned between the second layer and the at least one surface; the first proportion being greater than the second proportion or the third proportion, and the second proportion being greater than the third proportion and the third proportion being no more than 5%.

19. A coated vascular stent having a luminal surface and an abluminal surface, the stent comprising: an implantable frame and a coating deposited on the abluminal surface, the coating comprising a. a first taxane solid form composition having a vibrational spectrum comprising at least two peaks between 1735 and 1705 cm$^{-1}$ and a solubility of less than 20% wt. after 24 hours in porcine serum; and
b. a second taxane therapeutic state solid form composition having a vibrational spectrum consisting of a single peak between 1735 and 1705 cm$^{1}$ and a solubility of greater than about 50% wt. after 24 hours in porcine serum;

wherein the dose of taxane therapeutic agent on the abluminal surface is less than about 1.00 μg/mm$^2$; and wherein the coating comprises about 5% to 25% of the second taxane solid form composition, as measured by dissolution of the second taxane solid form composition in porcine serum.

* * * * *